(12) United States Patent
Ochiai

(10) Patent No.: US 9,453,212 B2
(45) Date of Patent: Sep. 27, 2016

(54) PHOSPHATIDIC ACID PHOSPHATASE GENE AND USE THEREOF

(75) Inventor: Misa Ochiai, Osaka (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 0 days.

(21) Appl. No.: 13/518,087

(22) PCT Filed: Dec. 27, 2010

(86) PCT No.: PCT/JP2010/073565
§ 371 (c)(1),
(2), (4) Date: Jun. 21, 2012

(87) PCT Pub. No.: WO2011/081135
PCT Pub. Date: Jul. 7, 2011

(65) Prior Publication Data
US 2012/0309950 A1    Dec. 6, 2012

(30) Foreign Application Priority Data

Dec. 28, 2009  (JP) ................................ 2009-298551

(51) Int. Cl.
| C07H 21/04 | (2006.01) |
| C12P 21/02 | (2006.01) |
| C12P 7/64 | (2006.01) |
| C12N 9/16 | (2006.01) |
| C12N 15/63 | (2006.01) |
| C12N 5/10 | (2006.01) |
| C12N 1/15 | (2006.01) |
| C12N 1/19 | (2006.01) |
| C12N 1/21 | (2006.01) |
| C12N 15/82 | (2006.01) |

(52) U.S. Cl.
CPC ............. *C12N 9/16* (2013.01); *C12N 15/8247* (2013.01); *C12P 7/6463* (2013.01); *C12Y 301/03004* (2013.01); *Y02P 20/52* (2015.11)

(58) Field of Classification Search
None
See application file for complete search history.

(56) References Cited

U.S. PATENT DOCUMENTS

| 2009/0293150 A1 | 11/2009 | Meyer et al. | |
| 2010/0196579 A1* | 8/2010 | Ochiai et al. | ................. 426/601 |
| 2012/0058245 A1 | 3/2012 | Meyer et al. | |

FOREIGN PATENT DOCUMENTS

| WO | 2009/008466 A1 | 1/2009 |
| WO | WO 2009/008466 A1 * | 1/2009 |
| WO | 2009/143398 | 11/2009 |

OTHER PUBLICATIONS

Han et al., J. Biol. Chem., 2007, vol. 282:37026-37035.*
English language version of WO 2009/008466 (Ochiai et al., Int'l Pub. Date: Jan. 15, 2009).*
Eck, S. L. and Wilson, J. M.,1996, in: Goodman & Gilman's The Pharmacological Basis of Therapeutics, Ninth Edition, McGraw-Hill, New York. See Chapter 5, pp. 77-101.*
Carman, "Phosphatidate Phosphatases and Diacylglycerol Pyrophosphate Phosphatases in *Saccharomyces cereveisiae* and *Escherichia coli*" *Biochim. Biophys. Acta* 1348:45-55, 1997.
Carman et al., "Roles of Phosphatidate Phosphatase Enzymes in Lipid Metabolism" *Trends Biochem. Sci.* 31(12):694-99, 2006.
Santos-Rosa et al., "The Yeast Lipin Smp2 Couples Phospholipid Biosynthesis to Nuclear Membrane Growth" *EMBO J.* 24:1931-41, 2005.
Han et al., "The *Saccharomyces cereveisiae* Lipin Homolog Is a $Mg^{2+}$-dependent Phosphatidate Phosphatase Enzyme" *J. Biol. Chem.* 281(14):9210-18, 2006.
O'Hara et al., "Control of Phospholipid Synthesis by Phosphorylation of the Yeast Lipin Pah1p/Smp2p $Mg^{2+}$-dependent Phosphatidate Phosphatase" *J. Biol. Chem.* 281(45):34537-48, 2006.
Han et al., "The Cellular Functions of the Yeast Lipin Homolog Pah1p Are Dependent on Its Phosphatidate Phosphatase Activity" *J. Biol. Chem.* 282(51):37026-35, 2007.
Carman et al., "Phosphatidic Acid Phosphatase, a Key Enzyme in the Regulation of Lipid Synthesis" *J. Biol. Chem.* 284(5):2593-97, 2009.
International Search Report for PCT/JP2010/073565, dated Feb. 1, 2011.
Extended European Search Report issued with respect to patent family member EP Patent Application No. 10840991.3, dated Apr. 25, 2013.

* cited by examiner

*Primary Examiner* — Xiaozhen Xie
(74) *Attorney, Agent, or Firm* — Greenblum & Bernstein, P.L.C.

(57) ABSTRACT

The present invention provides phosphatidic acid phosphatase cDNAs and recombinant vectors comprising nucleic acids encoding proteins having phosphatidic acid phosphatase activity wherein 100 amino acids at the N-terminal region and DXDX(T/V) catalytic site motif are conserved in the protein.

5 Claims, 19 Drawing Sheets

Figure 1-1

```
                    1                                                                                                    100
PAH1.1-genome      ATGCAGTCCGTGGGAAGCTTCTTCTCCACTGTCTCAAGGTTCTACAATGAGCTCAATCCAGCCACGCTTTCGGGCGCCATTGACGTGGTCGTGGTCGAGC
PAH1.1-ORF         ATGCAGTCCGTGGGAAGCTTCTTCTCCACTGTCTCAAGGTTCTACAATGAGCTCAATCCAGCCACGCTTTCGGGCGCCATTGACGTGGTCGTGGTCGAGC 101                                                                                                  200
PAH1.1-genome      AAGCCGATGGTGAATTAGCATGCTCACCATTTCATGTCCGCTTTGGCAAACTGAGCATTCTCCGACCGCACGGAAAAAGTGGTAAGCTTTGCCTGTCCTCA
PAH1.1-ORF         AAGCCGATGGTGAATTAGCATGCTCACCATTTCATGTCCGCTTTGGCAAACTGAGCATTCTCCGACCGCACGGAAAAAGTGGT----------------

201                                                                                                  300
PAH1.1-genome      CCTCCAAGCATATCGGTACCCGAGACGACCCTTGCTATTGCCCCCTCTTCAAAACCTTGCCGACTGAAATGCGTTTCCTGGTCTAAAGTGACTCCGTCGC
PAH1.1-ORF         ----------------------------------------------------------------------------------------------------

301                                                                                                  400
PAH1.1-genome      GCATGTCCGCTCCACATCAATAAGCTCTGATACATGGTCAAAATAACTCCTCGACGGCCTTCTTTAGGTGGAGGTGACCGTCAACGGTCGCCGTCGTTGAT
PAH1.1-ORF         ----------------------------------------------------------------GGAGGTGACCGTCAACGGTCGCCGTCGTTGAT 401                                                                                                  500
PAH1.1-genome      TTTCCTATGAAGGTTGGCGATGCAGGCGAAGCCTTCTTTGTTTTTGAGACTGAGCAGGACGTGCCCGAAGAGTTTGCCACGTCTCCACTAGCGGGACCCA
PAH1.1-ORF         TTTCCTATGAAGGTTGGCGATGCAGGCGAAGCCTTCTTTGTTTTTGAGACTGAGCAGGACGTGCCCGAAGAGTTTGCCACGTCTCCACTAGCGGGACCCA 501                                                                                                  600
PAH1.1-genome      ACACAGACAAAGTTGAGGAGGACATTGACTATCTGGATCTAGCCGAAGGGCATAGCACCGTGACATATCCGCCTGACGATATAGGTAAATCACGACGTTG
PAH1.1-ORF         ACACAGACAAAGTTGAGGAGGACATTGACTATCTGGATCTAGCCGAAGGGCATAGCACCGTGACATATCCGCCTGACGATATAG---------------

601                                                                                                  700
PAH1.1-genome      TATCATGCTGCTGAGACATGCGGAACGCGGCGGAATCCCGTCCCTCGCAAGGTTGTCGCTACTTACATAATACTACGCGCCATCCACAGTCTTAGATGCG
PAH1.1-ORF         --------------------------------------------------------------------------------------TCTTAGATGCG 701                                                                                                  800
PAH1.1-genome      GGCTATGTCAGCGCCCACAGTGGGCATGGATCAGAGTTTGAAGAAGACGAGAGAGCAGACTTGTCGCCTGAATTTGACAAAAAGCCAGATTACGCATCCG
PAH1.1-ORF         GGCTATGTCAGCGCCCACAGTGGGCATGGATCAGAGTTTGAAGAAGACGAGAGAGCAGACTTGTCGCCTGAATTTGACAAAAAGCCAGATTACGCATCCG 801                                                                                                  900
PAH1.1-genome      CGGTCAAATACGGCGGTACAAATGGACAAGGGAGACACCTAGGCAGTGCTAATGAGGCAACAACGTCTGTACATGCTTTCATGGAGCGGCAAGTTCAACG
PAH1.1-ORF         CGGTCAAATACGGCGGTACAAATGGACAAGGGAGACACCTAGGCAGTGCTAATGAGGCAACAACGTCTGTACATGCTTTCATGGAGCGGCAAGTTCAACG 901                                                                                                  1000
PAH1.1-genome      ATGGTCGCTTACCATGTCCCTACCACCCTCTCCGGTGTTAAAGTCTCGCGACATTATGGAGAACTTTCAGCCTATTGACTCGGCGGGCCCTTTCGATAAT
PAH1.1-ORF         ATGGTCGCTTACCATGTCCCTACCACCCTCTCCGGTGTTAAAGTCTCGCGACATTATGGAGAACTTTCAGCCTATTGACTCGGCGGGCCCTTTCGATAAT 1001                                                                                                 1100
PAH1.1-genome      AGTCGAGAGGATTCTGGACGCCTGCTCGCGCCAGAGACTATCGCCGTTAGCAATGGAGGCAGCAGTGGATCTCTGTTTCATCCTAAGGAGGGCATGATAA
PAH1.1-ORF         AGTCGAGAGGATTCTGGACGCCTGCTCGCGCCAGAGACTATCGCCGTTAGCAATGGAGGCAGCAGTGGATCTCTGTTTCATCCTAAGGAGGGCATGATAA 1101                                                                                                 1200
PAH1.1-genome      TGGACATGACTGGCTACAAGACCGAGGACTCTGACCTGAATTCCGATGCGTCTGATGAACATGATGTAGGCATGGCTGGCGCTTTGAATGGTCGCCATCG
PAH1.1-ORF         TGGACATGACTGGCTACAAGACCGAGGACTCTGACCTGAATTCCGATGCCGTCTGATGAACATGATGTAGGCATGCCTGGCCGCTTTGAATGGTCGCCATCG 1201                                                                                                 1300
PAH1.1-genome      GCGCAAAAGGGCTGCTCGGCCGGAAAAGGAGACGGGCCGGTGCATGGCGTCAACTCTCAAGACAACCTGGCCCACTGAAACTCCCTCAATTACAGCGCATGTC
PAH1.1-ORF         GCGCAAAAGGGCTGCTCGGCCGGAAAAGGAGACGGGCCGGTGCATGGCGTCAACTCTCAAGACAACCTGGCCCACTGAAACTCCCTCAATTACAGCGCATGTC 1301                                                                                                 1400
PAH1.1-genome      CTCAGCAGTCTCGACCCTCGCTTGCCGTTGCGACCTACTGCGCGACCTGCTCTACGCCCCAAAGCTAACAACGGGTTGGGCACTCTACCGAATCGCCGTT
PAH1.1-ORF         CTCAGCAGTCTCGACCCTCGCTTGCCGTTGCGACCTACTGCGCGACCTGCTCTACGCCCCAAAGCTAACAACGGGTTGGGCACTCTACCGAATCGCCGTT
```

Figure 1-2

```
              1401                                                                                1500
PAH1.1-genome CGTCATCGATGCCGAATCTTAAAGATTTCGTAGGTAAGAGGTCCACAATGGACTGTCAAACAACAAGGTGGGTAATGATGAGCAAGTCCAGGCAGTAGGC
PAH1.1-ORF    CGTCATCGATGCCGAATCTTAAAGATTTCGTAGGT---------------------------------------------------------------

1501                                                                                1600
PAH1.1-genome TGACTCGAGGCAACCCATAACGTCGCGTTATAGGTGAGAATAACAGTTTGTCGCCAAGCGTGCCGGCGATAATGCGACGCTTTCCTTCGAAGACGTTAAA
PAH1.1-ORF    ---------------------------------GAGAATAACAGTTTGTCGCCAAGCGTGCCGGCGATAATGCGACGCTTTCCTTCGAAGACGTTAAA 1601                                                                                1700
PAH1.1-genome CTCAAAGTTTTCCGCAAGAAGCGACATCAAAGATGGGACCAGTTCAAGCAGCTCCGTAGCCTCCTCGCCTCCACCGTCAGTTGCCAACCAGCAGAGCCCT
PAH1.1-ORF    CTCAAAGTTTTCCGCAAGAAGCGACATCAAAGATGGGACCAGTTCAAGCAGCTCCGTAGCCTCCTCGCCTCCACCGTCAGTTGCCAACCAGCAGAGCCCT 1701                                                                                1800
PAH1.1-genome AAAAACCGCCACCATCACCATCATCACCACAAAGAGCACACCGAAGGAAGCCATCCCCGTCGCCACTCGCACAAACCTTCACAGCAAGTGCAAGTGAAAA
PAH1.1-ORF    AAAAACCGCCACCATCACCATCATCACCACAAAGAGCACACCGAAGGAAGCCATCCCCGTCGCCACTCGCACAAACCTTCACAGCAAGTGCAAGTGAAAA 1801                                                                                1900
PAH1.1-genome AACCCCCGCCCAGATCCAATCCAGCTGTTAATGCGCTGAGCGATACGGAGCTCGAGGTTAGTGTCCCATTCATCAATAGTTCGTTCTTAAAGTGACAATG
PAH1.1-ORF    AACCCCCGCCCAGATCCAATCCAGCTGTTAATGCGCTGAGCGATACGGAGCTCGAG-------------------------------------------

1901                                                                                2000
PAH1.1-genome CCCATATCTCATGCCTGTCAGTACCGTCTTCATGATTGAGAATAGTATCAAACGCCGCGAACAACAGCAGCTACTCAAGAATCAGAGTGGTCCTCGGGAT
PAH1.1-ORF    ----------------------------------------------TATCAAACGCCGCGAACAACAGCAGCTACTCAAGAATCAGAGTGGTCCTCGGGAT 2001                                                                                2100
PAH1.1-genome GGGGCAGCTTACCGGTTAAAAATGACGGTCTAGGCACAGGGGAAGCAGATCACAAGGAGCATCACTCTAGTCATCCATCAATCGACATTCCAGCCCCACG
PAH1.1-ORF    GGGGCAGCTTACCGGTTAAAAATGACGGTCTAGGCACAGGGGAAGCAGATCACAAGGAGCATCACTCTAGTCATCCATCAATCGACATTCCAGCCCCACG 2101                                                                                2200
PAH1.1-genome GAAACCTGTGTTGAACGAGATGGAGATTGACGGGACTGTGTACAGACTCGCCATCAGCTTGTGTCCGGGTGATGAATTCGGAAAAGATTTGGTACGTCTG
PAH1.1-ORF    GAAACCTGTGTTGAACGAGATGGAGATTGACGGGACTGTGTACAGACTCGCCATCAGCTTGTGTCCGGGTGATGAATTCGGAAAAGATTTGG--------

2201                                                                                2300
PAH1.1-genome CTTGAAGTAACGAAATAATGGTTACGGCCATGGAACAAAATATGAAACAGCAAGCCGCTAACCTGTTCTACTTTGGTGAGGGGTCCGCAGGAAGCCAGCG
PAH1.1-ORF    -----------------------------------------------------------------------------------------AAGCCAGCG 2301                                                                                2400
PAH1.1-genome AAGCATTGTTTGCCACCAATCAGGTTTCGTTCGATGAGTTCGCGAAAGACCCACTCAAGACTCTCAATAACAAGAATTTGGTCTGCCTGATCAATGACCG
PAH1.1-ORF    AAGCATTGTTTGCCACCAATCAGGTTTCGTTCGATGAGTTCGCGAAAGACCCACTCAAGACTCTCAATAACAAGAATTTGGTCTGCCTGATCAATGACCG 2401                                                                                2500
PAH1.1-genome GTACAGAAGTCTACTGGCATTCATGCATGGGACTCAAAGGCGTGCATCCCATTAAGCGACTGTGTCAATTGATTTGTTTCCGCTAGGTATTTTACTTGGA
PAH1.1-ORF    GTA------------------------------------------------------------------------------------TTTTACTTGGA 2501                                                                                2600
PAH1.1-genome CAGCTGCGGGACCATATCTTTCCTCACTGATGCTCTTCCGGAAGCCTCTCTCTGACGAAACGCTCCATCAGCTTTCAGCCAAGGACTCGCGGCATCTATC
PAH1.1-ORF    CAGCTGCGGGACCATATCTTTCCTCACTGATGCTCTTCCGGAAGCCTCTCTCTGACGAAACGCTCCATCAGCTTTCAGCCAAGGACTCGCGGCATCTATC 2601                                                                                2700
PAH1.1-genome AGATCGACTCGCTGTGCAAGATGAGCCCCCAACCCGTTTCGGCGCTCTCTCCAGATGGCTAAGGGGATCACAAACCTCGTCCCAATTGAGCGCGATGGAG
PAH1.1-ORF    AGATCGACTCGCTGTGCAAGATGAGCCCCCAACCCGTTTCGGCGCTCTCTCCAGATGGCTAAGGGGATCACAAACCTCGTCCCAATTGAGCGCGATGGAG 2701                                                                                2800
PAH1.1-genome CAAGGGCAAAGACAACGTACTCCCAGTACCAACGATGCCTTGCAGCCTGCTCAGTTAGAGGAGGTACATGAAATCCTCTTTTATTCAAAAAGCCCCGAGA
PAH1.1-ORF    CAAGGGCAAAGACAACGTACTCCCAGTACCAACGATGCCTTGCAGCCTGCTCAGTTAGAGGAG-------------------------------------
```

Figure 1-3

```
                      2801                                                                                            2900
PAH1.1-genome  TGCAATAGTACAACCAGTTACTGACAACACCTCGGTATCGCTGTAGAGTCAAGCTTTACAGAGCGTGAAAGTCGAATCGATTAAGCACACTTCCGGATCA
PAH1.1-ORF     ---------------------------------------------AGTCAAGCTTTACAGAGCGTGAAAGTCGAATCGATTAAGCACACTTCCGGATCA 2901                                                                                            3000
PAH1.1-genome  CATTCATCACTTCTACGCGCTCCTAAACCAATGACTCGTAGCACCTCTCTGCCGATCGACGAAGGGATCGCCGGGTCTATATCAGACGAGTACGCTGGAA
PAH1.1-ORF     CATTCATCACTTCTACGCGCTCCTAAACCAATGACTCGTAGCACCTCTCTGCCGATCGACGAAGGGATCGCCGGGTCTATATCAGACGAGTACGCTGGAA 3001                                                                                            3100
PAH1.1-genome  GCTCGCCTCCGACACATTCTGCGCTCAAGAGCAGTAGACGGTATGCGAAAACGCTTCGCTTGACATCTGAACAGTTGGTACGTGCCTACAACCGGATAGC
PAH1.1-ORF     GCTCGCCTCCGACACATTCTGCGCCTCAAGAGCAGTAGACGGTATGCGAAAACGCTTCGCTTGACATCTGAACAGTTG---------------------

3101                                                                                            3200
PAH1.1-genome  GTATTGAATTGCGCGTGTACCAGCAGCATTGAAATCTCACACGGCATTGTCCGCTTCTGAAATAGAAATCACTAAATTTGAAAAAAGGCGCCAATACATT
PAH1.1-ORF     -------------------------------------------------------------AAATCACTAAATTTGAAAAAAGGCGCCAATACATT 3201                                                                                            3300
PAH1.1-genome  GACGTTTTCAGTAACGTCAAGTTATCAAGGCAAAGCAGTTTGTTCCGCCAAATTGTTTCTGTGGGACCATGACTACCAAGTCGTCATATCGGACATTGAT
PAH1.1-ORF     GACGTTTTCAGTAACGTCAAGTTATCAAGGCAAAGCAGTTTGTTCCGCCAAATTGTTTCTGTGGGACCATGACTACCAAGTCGTCATATCGGACATTGAT 3301                                                                                            3400
PAH1.1-genome  GGCACGATTACAAAGTCGGACGCTCTCGGACACATCTTTACCATGGCAGGAAAGGATTGGACCCATTCGGGTGTCGCCAAACTTTACACGGACATCGTCA
PAH1.1-ORF     GGCACGATTACAAAGTCGGACGCTCTCGGACACATCTTTACCATGGCAGGAAAGGATTGGACCCATTCGGGTGTCGCCAAACTTTACACGGACATCGTCA 3401                                                                                            3500
PAH1.1-genome  ACAATGGGTATCATATTTTGTACTTGACCTCAAGGGCCATTGGACAGGCAGACTACACACGAAAGTACCTCAAGAACGTGGAGCAAAATAACTACCAGTT
PAH1.1-ORF     ACAATGGGTATCATATTTTGTACTTGACCTCAAGGGCCATTGGACAGGCAGACTACACACGAAAGTACCTCAAGAACGTGGAGCAAAATAACTACCAGTT 3501                                                                                            3600
PAH1.1-genome  ACCGGATGGACCGGTGATCATGAGCCCTGATCGCTTGATGACCGCCTTCCACAGGTCAGCAGTGTTCACTGTGGCGCATAGGCTTCGTAGGGATGGGACA
PAH1.1-ORF     ACCGGATGGACCGGTGATCATGAGCCCTGATCGCTTGATGACCGCCTTCCACAGG-----------------------------------------

3601                                                                                            3700
PAH1.1-genome  TCTTGCTTTGAATGCTTACTAACAACCATTTGCGTTAACGTTTTAGGGAGGTGATTATGAGGAAGCCAGAAGAATTCAAGATGGCATGTCTGCCGTGACAT
PAH1.1-ORF     -------------------------------------------GAGGTGATTATGAGGAAGCCAGAAGAATTCAAGATGGCATGTCTGCCGTGACAT 3701                                                                                            3800
PAH1.1-genome  TCGGAGGCTGTTTGGAGATCGCAACCCCTTCTATGCCGGGTTTGGAAACAGAATCACGGACGCACTGTCCTACAGGAGCGTTAATGTCCCCTCATCTCGG
PAH1.1-ORF     TCGGAGGCTGTTTGGAGATCGCAACCCCTTCTATGCCGGGTTTGGAAACAGAATCACGGACGCACTGTCCTACAGGAGCGTTAATGTCCCCTCATCTCGG 3801                                                                                            3900
PAH1.1-genome  ATATTTACAATTGATTCGGGAGGTGAAGTCAAGCTGGAGCTCCTCAGCAGCTACAAATCATCGTGAGTACCCTTCACTGCACTTGCTTTTCCACTGGTGG
PAH1.1-ORF     ATATTTACAATTGATTCGGGAGGTGAAGTCAAGCTGGAGCTCCTCAGCAGCTACAAATCATC------------------------------------

3901                                                                                            4000
PAH1.1-genome  CGTCCATCCAGTCTTTGTTGGCGAAACATGGATTTAGGACCTGACCATTTTTGTCTCTTTGCTGATCTACTTGACACAAGATATCTCGCGTTGAACGATC
PAH1.1-ORF     -----------------------------------------------------------------------------ATATCTCGCGTTGAACGATC 4001                                                                                            4100
PAH1.1-genome  TCGTGAATGAGATCTTTCCAGGAAAAAGACAGGCACCCGAGTTCAATGACTGGAACTTTTGGCGGGGCGCCCTTGCCAGATATCGAGCTTCCAGTTGCGCC
PAH1.1-ORF     TCGTGAATGAGATCTTTCCAGGAAAAAGACAGGCACCCGAGTTCAATGACTGGAACTTTTGGCGGGGCGCCCTTGCCAGATATCGAGCTTCCAGTTGCGCC 4101                                                                                            4200
PAH1.1-genome  GTCTCATCAATACGCCCCTACAGCGGTGCCGGGCGAGTACAATGCACAAGGATATTCTGCAGGTCCTGCCCGGTTGGGAGTGATACGGAGCCTTACCAGT
PAH1.1-ORF     GTCTCATCAATACGCCCCTACAGCGGTGCCGGGCGAGTACAATGCACAAGGATATTCTGCAGGTCCTGCCCGGTTGGGAGTGATACGGAGCCTTACCAGT
```

Figure 1-4

```
                4201                                                                                          4300
PAH1.1-genome   TCCCTCACCTCAGCAGGACCGCTCAAGACGAGGACCGCTATCCCAATTTTTACCTCAAATTCGCCCCCTCCTCCGAATTCCTACCCATCGGCGATGAAGC
PAH1.1-ORF      TCCCTCACCTCAGCAGGACCGCTCAAGACGAGGACCGCTATCCCAATTTTTACCTCAAATTCGCCCCCTCCTCCGAATTCCTACCCATCGGCGATGAAGC 4301                                                                                          4400
PAH1.1-genome   CCGATGCACCGCATCAGTCCCAACCAGCCTCCTCCTCGCCTCAACCCCCCGCATCAGCGGCCGTCAGGACTGCAGATCGCTGATAGGAGCCGTCGACTCTC
PAH1.1-ORF      CCCATGCACCGCATCAGTCCCAACCAGCCTCCTCCTCGCCTCAACCCCCCGCATCAGCGGCCGTCAGGACTGCAGATCGCTGATAGGACCCGTCGACTCTC 4401                                                                                          4500
PAH1.1-genome   GCTGTCGTTGATGCGATATAGCAGCCATTCAGCTCCCACGTCCGCGCCAGTTTTGAGAACTTTGACCGACAGTTCCGAGCCCAATGTCGGCATTGACAGC
PAH1.1-ORF      GCTGTCGTTGATGCGATATAGCAGCCATTCAGCTCCCACGTCCGCGCCAGTTTTGAGAACTTTGACCGACAGTTCCGAGCCCAATGTCGGCATTGACAGC 4501                                                                                          4600
PAH1.1-genome   GGTGATGCAGGCGCTCTCTCTGAGGGGAATCAGGCAGGTTTAGAGCCAAATCGCTCACCTCACTTGGGATCCAACACTGATGGCGTTTTCCCACTGGACG
PAH1.1-ORF      GGTGATGCAGGCGCTCTCTCTGAGGGGAATCAGGCAGGTTTAGAGCCAAATCGCTCACCTCACTTGGGATCCAACACTGATGGCGTTTTCCCACTGGACG 4601                                                                                          4700
PAH1.1-genome   TTCCTCTTGTGAAGAGAAAGGCATCTGGTTTCTCGGTCTCACCGCCCCAGCTTGCCAGTCGACTAAGTGAGACTGTAATGCCTTTTCTTCGCCGACGAGC
PAH1.1-ORF      TTCCTCTTGTGAAGAGAAAGGCATCTGGTTTCTCGGTCTCACCGCCCCAGCTTGCCAGTCGACTAAGTGAGACTGTAATGCCTTTTCTTCGCCGACGAGC 4701                                                                                          4800
PAH1.1-genome   ATCCAAGTTGGAGCAGGGGCAGGAGCAGCAGCAGGAACAGCAGCAGGAACAGGAACAGGAACGAGAGGCATGATGTCCAGCTGGGTGCAGCAGCTGAAGGG
PAH1.1-ORF      ATCCAAGTTGGAGCAGGGGCAGGAGCAGCAGCAGGAACAGCAGCAGGAACAGGAACAGGAACGAGAGCATGATGTCCAGCTGGGTGCAGCAGCTGAAGGG 4801                                                                                          4900
PAH1.1-genome   GAGCAGCTTGCTTACACTCGAGAGTACGGGGAAGAAGAAGCCGCTGCTGGATATCTGGCGGAGGACCATGAACTCGGAGAGGATGAAGAGGATGAAGGAG
PAH1.1-ORF      GAGCAGCTTGCTTACACTCGAGAGTACGGGGAAGAAGAAGCCGCTGCTGGATATCTGGCGGAGGACCATGAACTCGGAGAGGATGAAGAGGATGAAGGAG 4901                                                                                          5000
PAH1.1-genome   AAGGAGCAGATGGATATGTTGGTTATTCTGGAGAAGAGGATGAAGGTCTGGAAGAAGATCAGCTCGAGGGTGAGGAAGACGAGGATGAGGATGACGATGA
PAH1.1-ORF      AAGGAGCAGATGGATATGTTGGTTATTCTGGAGAAGAGGATGAAGGTCTGGAAGAAGATCAGCTCGAGGGTGAGGAAGACGAGGATGAGGATGACGATGA 5001                      5034
PAH1.1-genome   TGTAGAGCTCAACATTGACGCTCCGTTCCTATGA
PAH1.1-ORF      TGTAGAGCTCAACATTGACGCTCCGTTCCTA---
```

Figure 2-1

```
                    1                                                                                                100
PAH1.2genome        ATGTATTCTGTCGGGAACTTCTTCTCGACCGTTACGAAATTCTACAATGAGATCAACCCGGCCACCCTCTCCGGCGCAATCGACATCATCGTCGTCCAGC
PAH11.2-ORF         ATGTATTCTGTCGGGAACTTCTTCTCGACCGTTACGAAATTCTACAATGAGATCAACCCCGCCACCCTCTCCGGCGCAATCGACATCATCGTCGTCCAGC 101                                                                                              200
PAH1.2genome        ACGGCCAACGGCGACCTTGCATGCTCTCCCTTCCACGTGCGTTTCGGCAAACTCAGCGTCCTCCGGCCGCAGGAGAAGGTCGTCGAGGTTCGGGTCAATGG
PAH11.2-ORF         AGGCCAACGGCGACCTTGCATGCTCTCCCTTCCACGTGCGTTTCGGCAAACTCAGCGTCCTCCGGCCGCAGGAGAAGGTCGTCGAGGTTCGGGTCAATGG 201                                                                                              300
PAH1.2genome        CGAAGTCATCGCCTTCCCCATGAAGGTCGGCGACGCAGGAGAGGCCTTCTTTGTGCTCGAGACCGACGACTATGTGCCGGATGAGTTTGCCACATCGCCT
PAH11.2-ORF         CGAAGTCATCGCCTTCCCCATGAAGGTCGGCGACGCAGGAGAGGCCTTCTTTGTGCTCGAGACCGACGACTATGTGCCGGATGAGTTTGCCACATCGCCT 301                                                                                              400
PAH1.2genome        ATCGCTGGTCCGAGTGACGAAGCCGACCTCGCCCCTGTTGACTACTTTGACCTGAACGGCCATCCCCACGGGTCTCAGGACCAGAAACGGAGGCAGCATC
PAH11.2-ORF         ATCGCTGGTCCGAGTGACGAAGCCGACCTCGCCCCTGTTGACTACTTTGACCTGAACGGCCATCCCCACGGGTCTCAGGACCAGAAACGGAGGCAGCATC 401                                                                                              500
PAH1.2genome        AGCAGCAACAGGTGCTGGAGGGCATGAGCGGACAGTATCCTCAAGGAACAGAAGGTAGAGATCGATATGAACACTATGAACGCACGATGGCGTCTTTAGC
PAH11.2-ORF         AGCAGCAACAGGTGCTGGAGGGCATGAGCGGACAGTATCCTCAAGGAACAGAAG-------------------------------------------

501                                                                                              600
PAH1.2genome        CCACTGTCAGTGTCAGTGCAGCACAGCTGTGTTGTAAAAGCGTTGACATATGTCAGAGCGCATTTTTTCTTCAATATTTCAGACGCAGCGGTCAGGACAA
PAH11.2-ORF         --------------------------------------------------------------------------------------------------

601                                                                                              700
PAH1.2genome        ACACATGGGATTATATATGAATATACTCAATCGATCGCACTCTTTCTTTTTGTTCTCCCGCGGCTATCAATAGACGATGCTGCTCTTGACAACGGCTATG
PAH11.2-ORF         ---------------------------------------------------------------------ACGATGCTCCTCTTGACAACGGCTATG 701                                                                                              800
PAH1.2genome        TGAGCGCTGCTAGTGGCCATGGCTCTGCTTTTGAAGAGAGCTTGAAGGACGACAGCGATCACGAGTCGGTCTTCTCGGCCACATCCCCAGGATCAGCAGA
PAH11.2-ORF         TGAGCGCTGCTAGTGGCCATGGCTCTGCTTTTGAAGAGAGCTTGAAGGACGACAGCGATCACGAGTCGGTCTTCTCGGCCACATCCCCAGGATCAGCAGA 801                                                                                              900
PAH1.2genome        ACGGATCGCCGCCGATTCTAATACTAAGGACACAGCACTCGACTTGCCTGGATCCTTTGGCCCAACGGTAGTGACTAATACCATCAAAAACAAGGACAGC
PAH11.2-ORF         ACGGATCGCCGCCGATTCTAATACTAAGGACACAGCACTCGACTTGCCTGGATCCTTTGGCCCAACGGTAGTGACTAATACCATCAAAAACAAGGACAGC 901                                                                                              1000
PAH1.2genome        ATCAACTTTCCAGTTGATGCCATCTTTCCTACAGTTGCACACGAGGAACAGGACATGGCTCTGATCAAAGATCAACAGGGCTCTCGATCCAGCCGTCGCA
PAH11.2-ORF         ATCAACTTTCCAGTTGATGCCATCTTTCCTACAGTTGCACACGAGGAACAGGACATGGCTCTGATCAAAGATCAACAGGGCTCTCGATCCAGCCGTCGCA 1001                                                                                             1100
PAH1.2genome        GAAGTGGTACGATGTTCTTACTGAACTTTATATACCATGATCTCTGCTGCATATGATTCCGCTTCCCGTACTATGCTCTGCTGTCGGCATTCCTAACCAT
PAH11.2-ORF         GAAGTG--------------------------------------------------------------------------------------------

1101                                                                                             1200
PAH1.2genome        ATTTTATCCGTTAATGTTTGTTTTGGGCGTTCGAATTGATGCAGAGGTCCTATTCGATATGACAGGATACAAGACCGACTCATGCTCGGACTCGTCGGAT
PAH11.2-ORF         ----------------------------------------------AGGTCCTATTCGATATGACAGGATACAAGACCGACTCATGCTCGGACTCGTCGGAT 1201                                                                                             1300
PAH1.2genome        GATGAGGATGGCTTGCCTCGTGGCATTCTATCGGATAGTGAGCGTCACGGTCGGTAGCACGCGTAAGAAGTTCAGGAGGAGCAAGTCGCCACCTTTCAATGG
PAH11.2-ORF         GATGAGGATGGCTTGCCTCGTGGCATTCTATCGGATAGTGAGCGTCACGGTCGGTAGCACGCGTAAGAAGTTCAGGAGGAGCAAGTCGCCACCTTTCAATGG 1301                                                                                             1400
PAH1.2genome        AGCAGAGGCACCAATTGCTGGAGGACATTAAACAAGGAGCGCGTTCCTGAAGCCCGAGGAAAGCCTTGCAAACACACAGATTGAACGTCAAAGTAGGCACAC
PAH11.2-ORF         AGCAGAGGCACCAATTGCTGGAGGACATTAAACAAGGAGCGCGTTCCTGAAGCCCGAGGAAAGCCTTGCAAACACACAGATTGAACGTCAAA---------
```

Figure 2-2

```
                1401                                                                                1500
PAH1.2genome    TAGTTTATCGCACCTTGATGATCATCTCAGCGACGTCTCTGCCCCAACTCACTCTTGATATTTTTTTTTATCTTCAGCATCCCGGGCAAGTAGGAAAAC
PAH11.2-ORF     ------------------------------------------------------------------------CATCCCGGGCAAGTAGGAAAAC 1501                                                                                1600
PAH1.2genome    AAAGAGGGCAAGCATTCCAAGTGCATGGCAAGGACGAAGGAACAGGAAGAGAGCCAACAGCATGCCTGCTATCGGTGAACCAGGTAGCGATCATGTACCA
PAH11.2-ORF     AAAGAGGGCAAGCATTCCAAGTGCATGGCAAGGACGAAGGAACAGGAAGAGAGCCAACAGCATGCCTGCTATCGGTGAACCAG----------------

1601                                                                                1700
PAH1.2genome    TATGGAAGGAGTAACTGTTAGAAATTGCAGTCAGCTAATATGTTTTATAACTCTTGTACAGACTTGGCATTTCCTGCCTATGTGGCTCGCCGAGCTAACC
PAH11.2-ORF     -----------------------------------------------------ACTTGGCATTTCCTGCCTATGTGGCTCGCCGACCTAACC 1701                                                                                1800
PAH1.2genome    ATCGTCGCGATGCTCAAGCAAACCAGACGGATGTTGCAATGGACGACAAGCCCAAGCCCAAGCGCACTGCTCGGCCCAGCGTTATGAGCGATACGGAGAT
PAH11.2-ORF     ATCGTCGCGATGCTCAAGCAAACCAGACGGATGTTGCAATGGACGACAAGCCCAAGCCCAAGCGCACTGCTCCGCCCAGCGTTATGAGCGATACGGAGAT 1801                                                                                1900
PAH1.2genome    GGAGGTAAGAATCGCAACTTGACATAAATTACAGTGTATCGATCGACCTGTGGCCTCAGTGACTACTGTTACTCATCTGCTTTTCGCAAACGTTCTGCAA
PAH11.2-ORF     GGAG--------------------------------------------------------------------

1901                                                                                2000
PAH1.2genome    CTAGTATGAATCCAACAATGTCCCTGCATCTACCCAGGGTAAAGAGTGGACCTGGGGATGGGGAACGCTGCCTGTCAAACAGGATAACCCTGATGAAGAG
PAH11.2-ORF     ----TATGAATCCAACAATGTCCCTGCATCTACCCAGGGTAAAGAGTGGACCTGGGGATGGGGAACGCTGCCTGTCAAACAGGATAACCCTGATGAAGAG 2001                                                                                2100
PAH1.2genome    GATGAGATCAAGGAACAAATTACGGAAGAAAAGGCGCCCGAAGTTCCTGTGGAGATTGAGGCAAAGGAGTTTCAGATGGGATCAACAAAATGCCGCGTAG
PAH11.2-ORF     GATGAGATCAAGGAACAAATTACGGAAGAAAAGGCGCCCGAAGTTCCTGTGGAGATTGAGGCAAAGGAGTTTCAGATGGGATCAACAAAATGCCGCGTAG 2101                                                                                2200
PAH1.2genome    CGGTCAGTCTCTGCGGAGAGGATGACTTTGGAAAGGACATTGTAGGTTACCATCGCAGTCCTTACTCCCTTTACTCAGTCATCAGTACGTCGTTGGTATT
PAH11.2-ORF     CGGTCAGTCTCTGCGGAGAGGATGACTTTGGAAAGGACATTGT--------------------------------

2201                                                                                2300
PAH1.2genome    TGAATTGCAGTTTAACATGTGGCCTCTGCTTGTGATATAGGTTGCTAGCCACAAGGCTTTTCAAAGAGCCCAGTTGACCTTTGAGGCATTCTCCAAAGAT
PAH11.2-ORF     ----------------------------------TGCTAGCCACAAGGCTTTTCAAAGAGCCCAGTTGACCTTTGAGGCATTCTCCAAAGAT 2301                                                                                2400
PAH1.2genome    CCCGCGGCAATTCTGGCCGACAAGAGACTTGTGTGTTACATGGATGGGCGGTTTTATTCGTGGAGTAATGCCGTTCCTCAGCTCGCAGCCCTTCTCTTCT
PAH11.2-ORF     CCCGCGGCAATTCTGGCCGACAAGAGACTTGTGTGTTACATGGATGGGCGGTTTTATTCGTGGAGTAATGCCGTTCCTCAGCTCGCAGCCCTTCTCTTCT 2401                                                                                2500
PAH1.2genome    TCCACCAGCCTCTTTCAGACGCGGCCTCTGCTCTCGACCTCAAGGACCAAAAGGCACATGCGGCCGAGGACAGACCGAGCGCCACGCGTTTTGGCACAAT
PAH11.2-ORF     TCCACCAGCCTCTTTCAGACGCGGCCTCTGCTCTCGACCTCAAGGACCAAAAGGCACATGCGGCCGAGGACAGACCGAGCGCCACGCGTTTTGGCACAAT 2501                                                                                2600
PAH1.2genome    CTCCAGATGGTTCAGGAAGGCGCCTGCAGGCAGCGCGTCCCCCTCTATTGCAGATATGGCCTCAGCATCCTCGACAACCCTTGCAGGTGGTGAGACCGCC
PAH11.2-ORF     CTCCAGATGGTTCAGGAAGGCGCCTGCAGGCAGCGCGTCCCCCTCTATTGCAGATATGGCCTCAGCATCCTCGACAACCCTTGCAGGTGGTGAGACCGCC 2601                                                                                2700
PAH1.2genome    GCTGTCGCTGTGGGATCAGATGACGACGAGCCCTTGCACAACAAGGCCCTGCGTAGCAAATCCCTGCCCCCACTGGAGACTGGCCGGACCGACGACCACA
PAH11.2-ORF     GCTGTCGCTGTGGGATCAGATGACGACGAGCCCTTGCACAACAAGGCCCTGCGTAGCAAATCCCTGCCCCCACTGGAGACTGGCCGGACCGACGACCACA 2701                                                                                2800
PAH1.2genome    GTCAGAGCCATGTCGCTGTACCTGCGCTTTCGGAGAAAGCAGCGGACGGTGTCCCAGATCAGAAGCGCTATGCCAAGACGCTGCGGCTCACCTCGGAACA
PAH11.2-ORF     GTCAGAGCCATGTCGCTGTACCTGCGCTTTCGGAGAAAGCAGCGGACGGTGTCCCAGATCAGAAGCGCTATGCCAAGACGCTGCGGCTCACCTCGGAACA
```

Figure 2-3

```
                2801                                                                                              2900
PAH1.2genome    GCTTCAATCCTTGGGTTTGAAAAAGGGCGCCAACACGGTCTCGTTCTCAGTGACATCGTCCTACCAGGGAACTGCAACTTGTGTAGCCAAGATCTTTTTG
PAH11.2-ORF     GCTTCAATCCTTGGGTTTGAAAAAGGGCGCCAACACGGTCTCGTTCTCAGTGACATCGTCCTACCAGGGAACTGCAACTTGTGTAGCCAAGATCTTTTTG 2901                                                                                              3000
PAH1.2genome    TGGGATTACGACTCCCAGGTGGTGATCTCGGATATTGATGGTACAATCACAAAGTCAGATGCCCTCGGCCACATTTTTGCCATGGCCGGTCGGCGACTGGA
PAH11.2-ORF     TGGGATTACGACTCCCAGGTGGTGATCTCGGATATTGATGGTACAATCACAAAGTCAGATGCCCTCGGCCACATTTTTGCCATGGCCGGTCGGCGACTGGA 3001                                                                                              3100
PAH1.2genome    CGCATCTCGGTGTCGGCCAAGCTGTTCACAGATATTCGCAGCAACGGATATCACATCCTGTACCTGACCTCCCGAGCCATTGGCCAGGCAGACTACACACG
PAH11.2-ORF     CGCATCTCGGTGTCGGCCAAGCTGTTCACAGATATTCGCAGCAACGGATATCACATCCTGTACCTGACCTCCCGAGCCATTGGCCAGGCAGACTACACACG 3101                                                                                              3200
PAH1.2genome    CAAGTATCTTCAGAAGGTCGAGCAAAACAGTTACCAGCTCCCGGATGGCCCTGTCATCATGAGTCCAGACCGTCTGTTCTCTGCCTTCCATCGTGAGGTG
PAH11.2-ORF     CAAGTATCTTCAGAAGGTCGAGCAAAACAGTTACCAGCTCCCGGATGGCCCTGTCATCATGAGTCCAGACCGTCTGTTCTCTGCCTTCCATCGTGAGGTG 3201                                                                                              3300
PAH1.2genome    ATTATCCGGAAACCAGAGGTGTTCAAGATGGCGTGTCTGCCGTGATGTGAAGAAGCTGTTTGGGGACAGGAACCCGTTCTATGCTGGATTTGGAAACCGGA
PAH11.2-ORF     ATTATCCGGAAACCAGAGGTGTTCAAGATGGCGTGTCTGCCGTGATGTGAAGAAGCTGTTTGGGGACAGGAACCCGTTCTATGCTGGATTTGGAAACCGGA 3301                                                                                              3400
PAH1.2genome    TCACGGACGCCCTCTCCTACCGCAGTGTCAACGTTCCACCCTCCCGAATCTTCACCATTGACTCTTATGGTGAGGTGAAGTTGGAGCTGCTCAGTGCTTT
PAH11.2-ORF     TCACGGACGCCCTCTCCTACCGCAGTGTCAACGTTCCACCCTCCCGAATCTTCACCATTGACTCTTATGGTGAGGTGAAGTTGGAGCTGCTCAGTGCTTT 3401                                                                                              3500
PAH1.2genome    CAAGTCTTCGTAAGTGTCTCTGCTTTCCACGGCAATCAGAAGTGTGAAAGAAGGAATCAAAGTGGCGTTTTTATTATCTCTCCTTCATTACTTATCCTCG
PAH11.2-ORF     CAAGTCTTC----------------------------------------------------------------------------------------

3501                                                                                              3600
PAH1.2genome    TTACAACTTTGTACGGTAGATACTTGGCTTTGAATGACCTCGTCAATGAGATCTTCCCAGGACAACGAGTTGCACCCGAGTTCAACGACTGGAACTTTTG
PAH11.2-ORF     --------------------ATACTTGGCTTTGAATGACCTCGTCAATGAGATCTTCCCAGGACAACGAGTTGCACCCGAGTTCAACGACTGGAACTTTTG 3601                                                                                              3700
PAH1.2genome    GAAATCGGATTTACCACGGATTGATCTCCCTGATCTCCCCATCCCCAACAATAATTATACATCAGGATCTTCGACATCGCTCCTCTCATCCACCACTAGC
PAH11.2-ORF     GAAATCGGATTTACCACGGATTGATCTCCCTGATCTCCCCATCCCCAACAATAATTATACATCAGGATCTTCGACATCGCTCCTCTCATCCACCACTAGC 3701                                                                                              3800
PAH1.2genome    GTGGCCAAGAAGGTGGCGTCTTTGACCAGCTCTTCATCGAGCTCGAACCTTCTCCAGCCAACGTCGCCCACTAGCCCTACGGGAGATTTCAAGAACAAGC
PAH11.2-ORF     GTGGCCAAGAAGGTGGCGTCTTTGACCAGCTCTTCATCGAGCTCGAACCTTCTCCAGCCAACGTCGCCCACTAGCCCTACGGGAGATTTCAAGAACAAGC 3801                                                                                              3900
PAH1.2genome    GCCTGTCTAATGACAGAAACACGTATGCGGGCGTCCTTTCAGGACGTCAGGACACATGGACCAGCGATGATGAATATCAGGATCAACAGCAGCGACTGAT
PAH11.2-ORF     GCCTGTCTAATGACAGAAACACGTATGCGGGCGTCCTTTCAGGACGTCAGGACACATGGACCAGCGATGATGAATATCAGGATCAACAGCAGCGACTGAT 3901                                                                                              4000
PAH1.2genome    CGCGGGGTCACTCTGCGCCCGTCAACGCCCAGGATCAGAGTTGAAGGCAGGACAGGAGCTGAAGGAGGATGCAAGGAAGGCACGATCTGGCTCGCCATCGATG
PAH11.2-ORF     CGCGGGGTCACTCTGCGCCCGTCAACGCCCAGGATCAGAGTTGAAGGCAGGACAGGAGCTGAAGGAGGATGCAAGGAAGGCACGATCTGCTCCCCATCGATG 4001                                                                                              4100
PAH1.2genome    CTCTCTGCTCTTGTTCCATCGCCGGTTAATCCGCGCAGTGAGGAGTGGCAGCATCAGCAGTCAGACCAACCCTGTGCCCTCGTCGATGCCGGAGTTCGGTTA
PAH11.2-ORF     CTCTCTGCTCTTGTTCCATCGCCGGTTAATCCGCGCAGTGAGGAGTGGCAGCATCAGCAGTCAGACCAACCCTGTGCCCTCGTCGATGCCGGAGTTCGGTTA 4101                                                                                              4200
PAH1.2genome    CACCGCATTCGCCCGAGATGAAAGGGATCATCGGGTCGCTGCCGTCACCAGTGTCTTCGTTTGAGAGCGGTGCGGATGTGGTGCGTCGGATGTCCATTCC
PAH11.2-ORF     CACCGCATTCGCCCGAGATGAAAGGGATCATCGGGTCGCTGCCGTCACCAGTGTCTTCGTTTGAGAGCGGTGCGGATGTGGTGCGTCGGATGTCCATTCC
```

Figure 2-4

```
                4201                                                                                                4300
PAH1.2genome    CTCGCCTCCACCGTTGGAGGGGCTGCTCCAGACGGATGAGGAGGTGGCTCAGGCATCGAGCAAGGCGCTGGCGCTTCAGGGATCGGACACAGCAGATTTG
PAH11.2-ORF     CTCGCCTCCACCGTTGGAGGGGCTGCTCCAGACGGATGAGGAGGTGGCTCAGGCATCGAGCAAGGCGCTGGCGCTTCAGGGATCGGACACAGCAGATTTG 4301                                                                                                4400
PAH1.2genome    AGCAGAGAGAGGCAGTGTTCAGGCCAAGAGTGATGTGATGGACGACCTTGTGGCGGTCAAGGAGGAAGAGGAGGACGAGACCGATCAGCAGCGGTTGCTGG
PAH11.2-ORF     AGCAGAGAGAGGCAGTGTTCAGGCCAAGAGTGATGTGATGGACGACCTTGTGGCGGTCAAGGAGGAAGAGGAGGACGAGACCGATCAGCAGCGGTTGCTGG 4401                                                                                                4500
PAH1.2genome    ATGCAGCGTATGTGGATGAGTATCTGGATGAGGAGGATGAGGAGGGATATGATGGATATGACGAGCAGGGTGAGGATGAGATGGACGAGGAGGATGAGGA
PAH11.2-ORF     ATGCAGCGTATGTGGATGAGTATCTGGATGAGGAGGATGAGGAGGGATATGATGGATATGACGAGCAGGGTGAGGATGAGATGGACGAGGAGGATGAGGA 4501                            4552
PAH1.2genome    GGACGAGTATCTGGATGAGATTGAGGAGACTCTGGAGGAGCCGTTCCTGTAG
PAH11.2-ORF     GGACGAGTATCTGGATGAGATTGAGGAGACTCTGGAGGAGCCGTTCCTG---
```

Figure 3-1

```
   1 ATGCAGTCCGTGGGAAGCTTCTTCTCCACTGTCTCAAGGTTCTACAATGAGCTCAATCCAGCCACGCTTTCGGGCGCCATTGACGTGGTCGTGGTCGAGC
     M  Q  S  V  G  S  F  F  S  T  V  S  R  F  Y  N  E  L  N  P  A  T  L  S  G  A  I  D  V  V  V  E  Q  ·

101 AAGCCGATGGTGAATTAGCATGCTCACCATTTCATGTCCGCTTTGGCAAACTGAGCATTCTCCGACCGCAGGAAAAAGTGGTGGAGGTGACCGTCAACGG
     · A  D  G  E  L  A  C  S  P  F  H  V  R  F  G  K  L  S  I  L  R  P  Q  E  K  V  V  E  V  T  V  N  G  ·

201 TCGCGTCGTTGATTTTCCTATGAAGGTTGGCGATGCAGGCGAAGCCTTCTTTGTTTTTGAGACTGAGCAGGACGTGCCCGAAGAGTTTGCCACGTCTCCA
     · R  V  V  D  F  P  M  K  V  G  D  A  G  E  A  F  F  V  F  E  T  E  Q  D  V  P  E  E  F  A  T  S  P

301 CTAGCGGGACCCAACACAGACAAAGTTGAGGAGGACATTGACTATCTGGATCTAGCCGAAGGGCATAGCACCGTGACATATCCGCCTGACGATATAGTCT
     L  A  G  P  N  T  D  K  V  E  E  D  I  D  Y  L  D  L  A  E  G  H  S  T  V  T  Y  P  P  D  D  I  V  L  ·

401 TAGATGCGGGCTATGTCAGCGCCCACAGTGGGCATGGATCAGAGTTTGAAGAAGACGAGAGAGCAGACTTGTCGCCTGAATTTGACAAAAAGCCAGATTA
     · D  A  G  Y  V  S  A  H  S  G  H  G  S  E  F  E  E  D  E  R  A  D  L  S  P  E  F  D  K  K  P  D  Y  ·

501 CGCATCCGCGGTCAAATACGGCGGTACAAATGGACAAGGGAGACACCTAGGCAGTGCTAATGAGGCAACAACGTCTGTACATGCTTTCATGGAGCGGCAA
     · A  S  A  V  K  Y  G  G  T  N  G  Q  Q  G  R  H  L  G  S  A  N  E  A  T  T  S  V  H  A  F  M  E  R  Q

601 GTTCAACGATGGTCGCTTACCATGTCCCTACCACCCTCTCCGGTGTTAAAGTCTCGCGACATTATGGAGAACTTTCAGCCTATTGACTCGGCGGGCCCTT
     V  Q  R  W  S  L  T  M  S  L  P  P  S  P  V  L  K  S  R  D  I  M  E  N  F  Q  P  I  D  S  A  G  P  F  ·

701 TCGATAATAGTCGAGAGGATTCTGGACGCCTGCTCGCGCCAGAGACTATCGCCGTTAGCAATGGAGGCAGCAGTGGATCTCTGTTTCATCCTAAGGAGGG
     · D  N  S  R  E  D  S  G  R  L  L  A  P  E  T  I  A  V  S  N  G  G  S  S  G  S  L  F  H  P  K  E  G  ·

801 CATGATAATGGACATGACTGGCTACAAGACCGAGGACTCTGACCTGAATTCCGATGCGTCTGATGAACATGATGTAGGCATGGCTGGCGCTTTGAATGGT
     · M  I  M  D  M  T  G  Y  K  T  E  D  S  D  L  N  S  D  A  S  D  E  H  D  V  G  M  A  G  A  L  N  G

901 CGCCATCGGCGCAAAAGGGCTGCTCGGCGGAAAAGGAGAGGGCCGGTGCATGGCGTCAACTCTCAAGACAACCTGGCCACTGAAACTCCCTCAATTACAG
     R  H  R  R  K  R  A  A  R  R  K  R  R  G  P  V  H  G  V  N  S  Q  D  N  L  A  T  E  T  P  S  I  T  A  ·

1001 CGCATGTCCTCAGCAGTCTCGACCCTCGCTTGCCGTTGCGACCTACTGCGCGACCTGCTCTACGCCCCAAAGCTAACAACGGGTTGGGCACTCTACCGAA
     · H  V  L  S  S  L  D  P  R  L  P  L  R  P  T  A  R  P  A  L  R  P  K  A  N  N  G  L  G  T  L  P  N  ·

1101 TCGCCGTTCGTCATCGATGCCGAATCTTAAAGATTTCGTAGGTGAGAATAACAGTTTGTCGCCAAGCGTGCCGGCGATAATGCGACGCTTTCCTTCGAAG
     · R  R  S  S  S  M  P  N  L  K  D  F  V  G  E  N  N  S  L  S  P  S  V  P  A  I  M  R  R  F  P  S  K

1201 ACGTTAAACTCAAAGTTTTCCGCAAGAAGCGACATCAAAGATGGGACCAGTTCAAGCAGCTCCGTAGCCTCCTCGCCTCCACCGTCAGTTGCCAACCAGC
     T  L  N  S  K  F  S  A  R  S  D  I  K  D  G  T  S  S  S  S  S  V  A  S  S  P  P  P  S  V  A  N  Q  Q  ·

1301 AGAGCCCTAAAAACCGCCACCATCACCATCATCACCACAAAGAGCACACCGAAGGAAGCCATCCCCGTCGCCACTCGCACAAACCTTCACAGCAAGTGCA
     · S  P  K  N  R  H  H  H  H  H  H  H  K  E  H  T  E  G  S  H  P  R  R  H  S  H  K  P  S  Q  Q  V  Q  ·

1401 AGTGAAAAAACCCCCGCCCAGATCCAATCCAGCTGTTAATGCGCTGAGCGATACGGAGCTCGAGTATCAAACGCCGCGAACAACAGCAGCTACTCAAGAA
     · V  K  K  P  P  P  R  S  N  P  A  V  N  A  L  S  D  T  E  L  E  Y  Q  T  P  R  T  T  A  A  T  Q  E

1501 TCAGAGTGGTCCTGGGGATGGGGCAGCTTACCGGTTAAAAATGACGGTCTAGGCACAGGGGAAGCAGATCACAAGGAGCATCACTCTAGTCATCCATCAA
     S  E  W  S  W  G  W  G  S  L  P  V  K  N  D  G  L  G  T  G  E  A  D  H  K  E  H  H  S  S  H  P  S  I  ·

1601 TCGACATTCCAGCCCCACGGAAACCTGTGTTGAACGAGATGGAGATTGACGGGACTGTGTACAGACTCGCCATCAGCTTGTGTCCGGGTGATGAATTCGG
     · D  I  P  A  P  R  K  P  V  L  N  E  M  E  I  D  G  T  V  Y  R  L  A  I  S  L  C  P  G  D  E  F  G  ·

1701 AAAAGATTTGGAAGCCAGCGAAGCATTGTTTGCCACCAATCAGGTTTCGTTCGATGAGTTCGCGAAAGACCCACTCAAGACTCTCAATAACAAGAATTTG
     · K  D  L  E  A  S  E  A  L  F  A  T  N  Q  V  S  F  D  E  F  A  K  D  P  L  K  T  L  N  N  K  N  L

1801 GTCTGCCTGATCAATGACCGGTATTTTACTTGGACAGCTGCGGGACCATATCTTTCCTCACTGATGCTCTTCCGGAAGCCTCTCTCTGACGAAACGCTCC
     V  C  L  I  N  D  R  Y  F  T  W  T  A  A  G  P  Y  L  S  S  L  M  L  F  R  K  P  L  S  D  E  T  L  H  ·
```

Figure 3-2

```
1901  ATCAGCTTTCAGCCAAGGACTCGCGGCATCTATCAGATCGACTCGCTGTGCAAGATGAGCCCCCAACCCGTTTCGGCGCTCTCTCCAGATGGCTAAGGGG
       . Q  L  S  A  K  D  S  R  H  L  S  D  R  L  A  V  Q  D  E  P  P  T  R  F  G  A  L  S  R  W  L  R  G .

2001  ATCACAAACCTCGTCCCAATTGAGCGCGATGGAGCAAGGGCAAAGACAACGTACTCCCAGTACCAACGATGCCTTGCAGCCTGCTCAGTTAGAGGAGAGT
       . S  Q  T  S  S  Q  L  S  A  M  E  Q  G  Q  R  Q  R  T  P  S  T  N  D  A  L  Q  P  A  Q  L  E  E  S

2101  CAAGCTTTACAGAGCGTGAAAGTCGAATCGATTAAGCACACTTCCGGATCACATTCATCACTTCTACGCGCTCCTAAACCAATGACTCGTAGCACCTCTC
         Q  A  L  Q  S  V  K  V  E  S  I  K  H  T  S  G  S  H  S  S  L  L  R  A  P  K  P  M  T  R  S  T  S  L .

2201  TGCCGATCGACGAAGGGATCGCCGGGTCTATATCAGACGAGTACGCTGGAAGCTCGCCTCCGACACATTCTGCGCTCAAGAGCAGTAGACGGTATGCGAA
       . P  I  D  E  G  I  A  G  S  I  S  D  E  Y  A  G  S  S  P  P  T  H  S  A  L  K  S  S  R  R  Y  A  K .

2301  AACGCTTCGCTTGACATCTGAACAGTTGAAATCACTAAATTTGAAAAAAGGCGCCAATACATTGACGTTTTCAGTAACGTCAAGTTATCAAGGCAAAGCA
       . T  L  R  L  T  S  E  Q  L  K  S  L  N  L  K  K  G  A  N  T  L  T  F  S  V  T  S  S  Y  Q  G  K  A

2401  GTTTGTTCCGCCAAATTGTTTCTGTGGGACCATGACTACCAAGTCGTCATATCGGACATTGATGGCACGATTACAAAGTCGGACGCTCTCGGACACATCT
         V  C  S  A  K  L  F  L  W  D  H  D  Y  Q  V  V  I  S  D  I  D  G  T  I  T  K  S  D  A  L  G  H  I  F .

2501  TTACCATGGCAGGAAAGGATTGGACCCATTCGGGTGTCGCCAAACTTTACACGGACATCGTCAACAATGGGTATCATATTTTGTACTTGACCTCAAGGGC
       . T  M  A  G  K  D  W  T  H  S  G  V  A  K  L  Y  T  D  I  V  N  N  G  Y  H  I  L  Y  L  T  S  R  A .

2601  CATTGGACAGGCAGACTACACACGAAAGTACCTCAAGAACGTGGAGCAAAATAACTACCAGTTACCGGATGGACCGGTGATCATGAGCCCTGATCGCTTG
       . I  G  Q  A  D  Y  T  R  K  Y  L  K  N  V  E  Q  N  N  Y  Q  L  P  D  G  P  V  I  M  S  P  D  R  L

2701  ATGACCGCCTTCCACAGGGAGGTGATTATGAGGAAGCCAGAAGAATTCAAGATGGCATGTCTGCGTGACATTCGGAGGCTGTTTGGAGATCGCAACCCCT
         M  T  A  F  H  R  E  V  I  M  R  K  P  E  E  F  K  M  A  C  L  R  D  I  R  R  L  F  G  D  R  N  P  F .

2801  TCTATGCCGGGTTTGGAAACAGAATCACGGACGCACTGTCCTACAGGAGCGTTAATGTCCCCTCATCTCGGATATTTACAATTGATTCGGGAGGTGAAGT
       . Y  A  G  F  G  N  R  I  T  D  A  L  S  Y  R  S  V  N  V  P  S  S  R  I  F  T  I  D  S  G  G  E  V .

2901  CAAGCTGGAGCTCCTCAGCAGCTACAAATCATCATATCTCGCGTTGAACGATCTCGTGAATGAGATCTTTCCAGGAAAAAGACAGGCACCCGAGTTCAAT
       . K  L  E  L  L  S  S  Y  K  S  S  Y  L  A  L  N  D  L  V  N  E  I  F  P  G  K  R  Q  A  P  E  F  N

3001  GACTGGAACTTTTGGCGGGCGCCCTTGCCAGATATCGAGCTTCCAGTTGCGCCGTCTCATCAATACGCCCCTACAGCGGTGCCGGGCGAGTACAATGCAC
         D  W  N  F  W  R  A  P  L  P  D  I  E  L  P  V  A  P  S  H  Q  Y  A  P  T  A  V  P  G  E  Y  N  A  Q .

3101  AAGGATATTCTGCAGGTCCTGGCCGGTTGGGAGTGATACGGAGCCTTACCAGTTCCCTCACCTCAGCAGGACCGCTCAAGACGAGGACCGCTATCCCAAT
       . G  Y  S  A  G  P  G  R  L  G  V  I  R  S  L  T  S  S  L  T  S  A  G  P  L  K  T  R  T  A  I  P  I .

3201  TTTTACCTCAAATTCGCCCCCTCCTCCGAATTCCTACCCATCGGCGATGAAGCCCCATGCACCGCATCAGTCCCAACCAGCCTCCTCCTCGCCTCAACCC
       . F  T  S  N  S  P  P  P  P  N  S  Y  P  S  A  M  K  P  H  A  P  H  Q  S  Q  P  A  S  S  S  P  Q  P

3301  CCCGCATCAGCGCCGTCAGGACTGCAGATCGCTGATAGGACCCGTCGACTCTCGCTGTCGTTGATGCGATATAGCAGCCATTCAGCTCCCACGTCCGCGC
         P  A  S  A  P  S  G  L  Q  I  A  D  R  T  R  R  L  S  L  S  L  M  R  Y  S  S  H  S  A  P  T  S  A  P .

3401  CAGTTTTGAGAACTTTGACCGACAGTTCCGAGCCCAATGTCGGCATTGACAGCGGTGATGCAGGCGCTCTCTCTGAGGGGAATCAGGCAGGTTTAGAGCC
       . V  L  R  T  L  T  D  S  S  E  P  N  V  G  I  D  S  G  D  A  G  A  L  S  E  G  N  Q  A  G  L  E  P .

3501  AAATCGCTCACCTCACTTGGGATCCAACACTGATGGCGTTTTCCCACTGGACGTTCCTGTTGTGAAGAGAAAGGCATCTGGTTTCTCGGTCTCACCGCCC
       . N  R  S  P  H  L  G  S  N  T  D  G  V  F  P  L  D  V  P  V  V  K  R  K  A  S  G  F  S  V  S  P  P

3601  CAGCTTGCCAGTCGACTAAGTGAGACTGTAATGCCTTTTCTTCGCCGACGAGCATCCAAGTTGGAGCAGGGGCAGGAGCAGCAGCAGGAACAGCAGCAGG
         Q  L  A  S  R  L  S  E  T  V  M  P  F  L  R  R  R  A  S  K  L  E  Q  G  Q  E  Q  Q  Q  E  Q  Q  Q  E .

3701  AACAGGAACAGGAACGAGAGCATGATGTCCAGCTGGGTGCAGCAGCTGAAGGGGAGCAGCTTGCTTACACTCGAGAGTACGGGGAAGAAGAAGCCGCTGC
       . Q  E  Q  E  R  E  H  D  V  Q  L  G  A  A  A  E  G  E  Q  L  A  Y  T  R  E  Y  G  E  E  E  A  A  A .
```

Figure 3-3

```
3801  TGGATATCTGGCGGAGGACCATGAACTCGGAGAGGATGAAGAGGATGAAGGAGAAGGAGCAGATGGATATGTTGGTTATTCTGGAGAAGAGGATGAAGGT
       ·G Y L A E D H E L G E D E E D E G E G A D G Y V G Y S G E E D E G

3901  CTGGAAGAAGATCAGCTCGAGGGTGAGGAAGACGAGGATGAGGATGACGATGATGTAGAGCTCAACATTGACGCTCCGTTCCTATGAACATCCTTGTACA
       L E E D Q L E G E E D E D E D D D D V E L N I D A P F L

4001  TCAATGCGACAGATCACAGGGGTTGCAAGTCGTCTGATGCTATGAGCCTTCCAAGTTTTTGGCTGGATAAATGGGTGTTGTTGAGGATTTATTGTTGTTA
4101  CAAGGCGATGCCGATTCAAAAATGTGGATAGCCGCACTGGTGCAAGAGGTGGGAAATGGCAAAGAGGACGAGCAAGAAAGAAGAAGGAGAAAAAAAGACA
4201  TAAACTACCAACGAGAAAAGTCTATAACAGAAAAAAAAAAAAAAAAAA
```

Figure 4-1

```
   1  CCTTCGCATCACCAGCCCTTCTCGTCCTTCTCGTCCTTCTCTCCCACCCGCCTCTCTTCCCACGCCACACCATGTATTCTGTCGGGAACTTCTTCTCGAC
                                                                                     M  Y  S  V  G  N  F  F  S  T ·

101  CGTTACGAAATTCTACAATGAGATCAACCCCGCCACCCTCTCCGGCGCAATCGACATCATCGTCGTCCAGCAGGCCAACGGCGACCTTGCATGCTCTCCC
       · V  T  K  F  Y  N  E  I  N  P  A  T  L  S  G  A  I  D  I  I  V  V  Q  Q  A  N  G  D  L  A  C  S  P

201  TTCCACGTGCGTTTCGGCAAACTCAGCGTCCTCCGGCCGCAGGAGAAGGTCGTCGAGGTTCGGGTCAATGGCGAAGTCATCGCCTTCCCCATGAAGGTCG
        F  H  V  R  F  G  K  L  S  V  L  R  P  Q  E  K  V  V  E  V  R  V  N  G  E  V  I  A  F  P  M  K  V  G ·

301  GCGACGCAGGAGAGGCCTTCTTTGTGCTCGAGACCGACGACTATGTGCCGGATGAGTTTGCCACATCGCCTATCGCTGGTCCGAGTGACGAAGCCGACCT
       · D  A  G  E  A  F  F  V  L  E  T  D  D  Y  V  P  D  E  F  A  T  S  P  I  A  G  P  S  D  E  A  D  L ·

401  CGCCCCTGTTGACTACTTTGACCTGAACGGCCATCCCCACGGGTCTCAGGACCAGAAACGGAGGCAGCATCAGCAGCAACAGGTGCTGGAGGGCATGAGC
       · A  P  V  D  Y  F  D  L  N  G  H  P  H  G  S  Q  D  Q  K  R  R  Q  H  Q  Q  Q  Q  V  L  E  G  M  S

501  GGACAGTATCCTCAAGGAACAGAAGACGATGCTCCTCTTGACAACGGCTATGTGAGCGCTGCTAGTGGCCATGGCTCTGCTTTTGAAGAGAGCTTGAAGG
         G  Q  Y  P  Q  G  T  E  D  D  A  P  L  D  N  G  Y  V  S  A  A  S  G  H  G  S  A  F  E  E  S  L  K  D ·

601  ACGACAGCGATCACGAGTCGGTCTTCTCGGCCACATCCCCAGGATCAGCAGAACGGATCGCCGCCGATTCTAATACTAAGGACACAGCACTCGACTTGCC
       · D  S  D  H  E  S  V  F  S  A  T  S  P  G  S  A  E  R  I  A  A  D  S  N  T  K  D  T  A  L  D  L  P ·

701  TGGATCCTTTGGCCCAACGGTAGTGACTAATACCATCAAAAACAAGGACAGCATCAACTTTCCAGTTGATGCCATCTTTCCTACAGTTGCACACGAGGAA
       · G  S  F  G  P  T  V  V  T  N  T  I  K  N  K  D  S  I  N  F  P  V  D  A  I  F  P  T  V  A  H  E  E

801  CAGGACATGGCTCTGATCAAAGATCAACAGGGCTCTCGATCCAGCCGTCGCAGAAGTGAGGTCCTATTCGATATGACAGGATACAAGACCGACTCATGCT
         Q  D  M  A  L  I  K  D  Q  Q  G  S  R  S  S  R  R  R  S  E  V  L  F  D  M  T  G  Y  K  T  D  S  C  S ·

901  CGGACTCGTCGGATGATGAGGATGGCTTGCCTCGTGGCATTCTATCGGATAGTGAGCGTCACGGTCGTAGCACGCGTAAGAAGTTCAGGAGGAGCAAGTC
       · D  S  S  D  D  E  D  G  L  P  R  G  I  L  S  D  S  E  R  H  G  R  S  T  R  K  K  F  R  R  S  K  S ·

1001  GCACCTTTCAATGGAGCAGAGGCACCAATTGCTGGAGGACATTAAACAAGGAGCGTTCCTGAAGCCCGAGGAAAGCCTTGCAAACACACAGATTGAACGT
       · H  L  S  M  E  Q  R  H  Q  L  L  E  D  I  K  Q  G  A  F  L  K  P  E  E  S  L  A  N  T  Q  I  E  R

1101  CAAACATCCCGGGCAAGTAGGAAAACAAAGAGGGCAAGCATTCCAAGTGCATGGCAAGGACGAAGGAACAGGAAGAGAGCCAACAGCATGCCTGCTATCG
         Q  T  S  R  A  S  R  K  T  K  R  A  S  I  P  S  A  W  Q  G  R  R  N  R  K  R  A  N  S  M  P  A  I  G ·

1201  GTGAACCAGACTTGGCATTTCCTGCCTATGTGGCTCGCCGACCTAACCATCGTCGCGATGCTCAAGCAACCAGACGGATGTTGCAATGGACGACAAGCC
       · E  P  D  L  A  F  P  A  Y  V  A  R  R  P  N  H  R  R  D  A  Q  A  N  Q  T  D  V  A  M  D  D  K  P ·

1301  CAAGCCCAAGCGCACTGCTCGGCCCAGCGTTATGAGCGATACGGAGATGGAGTATGAATCCAACAATGTCCCTGCATCTACCCAGGGTAAAGAGTGGACC
       · K  P  K  R  T  A  R  P  S  V  M  S  D  T  E  M  E  Y  E  S  N  N  V  P  A  S  T  Q  G  K  E  W  T

1401  TGGGGATGGGGAACGCTGCCTGTCAAACAGGATAACCCTGATGAAGAGGATGAGATCAAGGAACAAATTACGGAAGAAAAGGCGCCCGAAGTTCCTGTGG
        W  G  W  G  T  L  P  V  K  Q  D  N  P  D  E  E  D  E  I  K  E  Q  I  T  E  E  K  A  P  E  V  P  V  E ·

1501  AGATTGAGGCAAAGGAGTTTCAGATGGGATCAACAAAATGCCGCGTAGCGCTCAGTCTCTGCGGAGAGGATGACTTTGGAAAGGACATTGTTGCTAGCCA
       · I  E  A  K  E  F  Q  M  G  S  T  K  C  R  V  A  L  S  L  C  G  E  D  D  F  G  K  D  I  V  A  S  H ·

1601  CAAGGCTTTTCAAAGAGCCCAGTTGACCTTTGAGGCATTCTCCAAAGATCCCGCGGCAATTCTGGCCGACAAGAGACTTGTGTGTTACATGGATGGGCGG
       · K  A  F  Q  R  A  Q  L  T  F  E  A  F  S  K  D  P  A  A  I  L  A  D  K  R  L  V  C  Y  M  D  G  R

1701  TTTTATTCGTGGAGTAATGCCGTTCCTCAGCTCGCAGCCCTTCTCTTCTTCCACCAGCCTCTTTCAGACGCGGCCTCTGCTCTCGACCTCAAGGACCAAA
         F  Y  S  W  S  N  A  V  P  Q  L  A  A  L  L  F  F  H  Q  P  L  S  D  A  A  S  A  L  D  L  K  D  Q  K ·

1801  AGGCACATGCGGCCGAGGACAGACCGAGCGCCACGCGTTTTGGCACAATCTCCAGATGGTTCAGGAAGGCGCCTGCAGGCAGCGCGTCCCCCTCTATTGC
       · A  H  A  A  E  D  R  P  S  A  T  R  F  G  T  I  S  R  W  F  R  K  A  P  A  G  S  A  S  P  S  I  A ·
```

Figure 4-2

```
1901  AGATATGGCCTCAGCATCCTCGACAACCCTTGCAGGTGGTGAGACCGCCGCTGTCGCTGTGGGATCAGATGACGACGAGCCCTTGCACAACAAGGCCCTG
       · D  M  A  S  A  S  S  T  T  L  A  G  G  E  T  A  A  V  A  V  G  S  D  D  D  E  P  L  H  N  K  A  L

2001  CGTAGCAAATCCCTGCCCCCACTGGAGACTGGCCGGACCGACGACCACAGTCAGAGCCATGTCGCTGTACCTGCGCTTTCGGAGAAAGCAGCGGACGGTG
        R  S  K  S  L  P  P  L  E  T  G  R  T  D  D  H  S  Q  S  H  V  A  V  P  A  L  S  E  K  A  A  D  G  V ·

2101  TCCCAGATCAGAAGCGCTATGCCAAGACGCTGCGGCTCACCTCGGAACAGCTTCAATCCTTGGGTTTGAAAAAGGGCGCCAACACGGTCTCGTTCTCAGT
       · P  D  Q  K  R  Y  A  K  T  L  R  L  T  S  E  Q  L  Q  S  L  G  L  K  K  G  A  N  T  V  S  F  S  V ·

2201  GACATCGTCCTACCAGGGAACTGCAACTTGTGTAGCCAAGATCTTTTTGTGGGATTACGACTCCCAGGTGGTGATCTCGGATATTGATGGTACAATCACA
       · T  S  S  Y  Q  G  T  A  T  C  V  A  K  I  F  L  W  D  Y  D  S  Q  V  V  I  S  D  I  D  G  T  I  T

2301  AAGTCAGATGCCCTCGGCCACATTTTTGCCATGGCCGGTCGCGACTGGACGCATCTCGGTGTCGCCAAGCTGTTCACAGATATTCGCAGCAACGGATATC
         K  S  D  A  L  G  H  I  F  A  M  A  G  R  D  W  T  H  L  G  V  A  K  L  F  T  D  I  R  S  N  G  Y  H ·

2401  ACATCCTGTACCTGACCTCCCGAGCCATTGGCCAGGCAGACTACACACGCAAGTATCTTCAGAAGGTCGAGCAAAACAGTTACCAGCTCCCGGATGGCCC
       · I  L  Y  L  T  S  R  A  I  G  Q  A  D  Y  T  R  K  Y  L  Q  K  V  E  Q  N  S  Y  Q  L  P  D  G  P ·

2501  TGTCATCATGAGTCCAGACCGTCTGTTCTCTGCCTTCCATCGTGAGGTGATTATCCGGAAACCAGAGGTGTTCAAGATGGCGTGTCTGCGTGATGTGAAG
       · V  I  M  S  P  D  R  L  F  S  A  F  H  R  E  V  I  I  R  K  P  E  V  F  K  M  A  C  L  R  D  V  K

2601  AAGCTGTTTGGGGACAGGAACCCGTTCTATGCTGGATTTGGAAACCGGATCACGGACGCCCTCTCCTACCGCAGTGTCAACGTTCCACCCTCCCGAATCT
         K  L  F  G  D  R  N  P  F  Y  A  G  F  G  N  R  I  T  D  A  L  S  Y  R  S  V  N  V  P  P  S  R  I  F ·

2701  TCACCATTGACTCTTATGGTGAGGTGAAGTTGGAGCTGCTCAGTGCTTTCAAGTCTTCATACTTGGCTTTGAATGACCTCGTCAATGAGATCTTCCCAGG
       · T  I  D  S  Y  G  E  V  K  L  E  L  L  S  A  F  K  S  S  Y  L  A  L  N  D  L  V  N  E  I  F  P  G ·

2801  ACAACGAGTTGCACCCGAGTTCAACGACTGGAACTTTTGGAAATCGGATTTACCACGGATTGATCTCCCTGATCTCCCCATCCCCAACAATAATTATACA
       · Q  R  V  A  P  E  F  N  D  W  N  F  W  K  S  D  L  P  R  I  D  L  P  D  L  P  I  P  N  N  N  Y  T

2901  TCAGGATCTTCGACATCGCTCCTCTCATCCACCACTAGCGTGGCCAAGAAGGTGGCCGTCTTTGACCAGCTCTTCATCGAGCTCGAACCTTCTCCAGCCAA
         S  G  S  S  T  S  L  L  S  S  T  T  S  V  A  K  K  V  A  S  L  T  S  S  S  S  S  N  L  L  Q  P  T ·

3001  CGTCGCCCACTAGCCCTACGGGAGATTTCAAGAACAAGCGCCTGTCTAATGACAGAAACACGTATGCGGGCGTCCTTTCAGGACGTCAGGACACATGGAC
       · S  P  T  S  P  T  G  D  F  K  N  K  R  L  S  N  D  R  N  T  Y  A  G  V  L  S  G  R  Q  D  T  W  T ·

3101  CAGCGATGATGAATATCAGGATCAACAGCAGCGACTGATCGCGGGTGACTCTGCGCCGTCAACGCCAGGATCAGAGTTGAAGGCAGGACAGGAGCTGAAG
       · S  D  D  E  Y  Q  D  Q  Q  Q  R  L  I  A  G  D  S  A  P  S  T  P  G  S  E  L  K  A  G  Q  E  L  K

3201  GAGGATGCAAGGAAGGCACGATCTGGCTCGCCATCGATGCTCTCTGCTCTTGTTCCATCGCCGGTTAATCCGCGCAGTGAGGAGTGGCAGCATCAGCAGTC
         E  D  A  R  K  A  R  S  G  S  P  S  M  L  S  A  L  V  P  S  R  L  I  R  A  V  R  S  G  S  I  S  S  Q ·

3301  AGACCAACCCTGTGCCCTCGTCGATGCGGAGTTCGGTTACACCGCATTCGCCCGAGATGAAAGGGATCATCGGGTCGCTGCCGTCACCAGTGTCTTCGTT
       · T  N  P  V  P  S  S  M  R  S  S  V  T  P  H  S  P  E  M  K  G  I  I  G  S  L  P  S  P  V  S  S  F ·

3401  TGAGAGCGGTGCGGATGTGGTGCGTCGGATGTCCATTCCCTCGCCTCCACCGTTGGAGGGGCTGCTCCAGACGGATGAGGAGGTGGCTCAGGCATCGAGC
       · E  S  G  A  D  V  V  R  R  M  S  I  P  S  P  P  P  L  E  G  L  L  Q  T  D  E  E  V  A  Q  A  S  S

3501  AAGGCGCTGGCGCTTCAGGGATCGGACACAGCAGATTTGAGCAGAGAGAGCAGTGTTCAGGCCAAGAGTGATGTGATGGACGACCTTGTGGCGGTCAAGG
         K  A  L  A  L  Q  G  S  D  T  A  D  L  S  R  E  S  S  V  Q  A  K  S  D  V  M  D  D  L  V  A  V  K  E ·

3601  AGGAAGAGGAGGACGAGACCGATCAGCAGCGGTTGCTGGATGCAGCGTATGTGGATGAGTATGTGGATGAGGAGGATGAGGAGGGATATGATGGATATGA
       · E  E  E  D  E  T  D  Q  Q  R  L  L  D  A  A  Y  V  D  E  Y  V  D  E  E  D  E  E  G  Y  D  G  Y  D ·

3701  CGAGCAGGGTGAGGATGAGATGGACGAGGAGGATGAGGAGGACGAGTATCTGGATGAGATTGAGGAGACTCTGGAGGAGCCCGTTCCTGTAGACGCGTTTT
       · E  Q  G  E  D  E  M  D  E  E  D  E  E  D  E  Y  L  D  E  I  E  E  T  L  E  E  P  F  L

3801  ATAATTTTTGTAAAAGTTCCCTTGTTGTAAAAAAAAAAAAAAAAAA
```

Figure 5-1

```
              1                                                                                                    100
MaPAH1.1      ----MQSVGSFFSTVSRFYNELNPATLSGAIDVVVVEQADGELACSPFHVRFGKLSILRPQEKVVVEVTVNGRVVDFPMKVGDAGEAFFVFET----EQDVP
MaPAH1.2      ----MYSVGNFFSTVTKFYNEINPATLSGAIDIIVVQRANGDLACSPFHVRFGKLSVLRPQEKVVEVRVNGEVIAFPMKVGDAGEAFFVLET----DDYVP
ScPAH1        ----MQYVGRALGSVSKTWSSINPATLSGAIDVIVVEHPDGRLSCSPFHVRFGKFQILKPSQKKVQVFINEKLSNMPMKLSDSGEAYFVFEMGDQVTDVP
mouse-Lipin1  MNYVGQLAGQVFVTVKELYKGLNPATLSGCIDIIYIRQPNGSLQCSPFHVRFGKMGVLRSREKVVDIEINGESVDLHMKLGDNGEAFFVQETDNDQEIIP
                                                                                                         *

101                                                                                                  200
MaPAH1.1      EEFATSPLAGPNTDKVEEDIDYLDLAEGHSTVTYPPDDIVLDAGYVSAHSGHGSEFEEDERADLSPEFDKKPDYASAVKYGGTNGQGRHLGSANEATTSV
MaPAH1.2      DEFATSPIAGPSDEADLAPVDYFDLNGHPHGSQDDQKRRQHQQQQVLEGMSGQYPQGTEDDAPLDNGYVSAASCHGSAFEESLKDDS----DHESVFSATS
ScPAH1        DELLVSPVMSATS--------------------------------------------SPPQSPE----TSILEGGTEGE--------------
mouse-Lipin1  MYLATSPILSEGAARMESQLK---------------RNSVDRIRCLDPTTAAQGLPPSDTPSTGSLGKKRKRRRKAQLDNLKRDDNVN----------

201                                                                                                  300
MaPAH1.1      HAFMERQVQRWSLTMSLPPSPVLKSRDIMENFQPIDSAGPFDNSREDSGRLLAPETIAVSNGGSSG-SLFHPKEGMIMDMTGYKTEDSDLNSDASDEHDV
MaPAH1.2      PGSAERIAADSNTKDTALDLPGSFGPTVVTNTIKNKDSINFPVDAIFPTVAHEEQDMALIKDQQGS-RSSRRRSEVLFDMTGYKTDSCSDSSDDEDGLPR
ScPAH1        --------------------------------------------------GEGENENK-------KKEKKVLEEPDFLDINDTGDSGSKNSETT
mouse-Lipin1  -SSEDEDMFPIEMSSDEDTAPMDGSRTLPNDVPPFQDDIPKENFPSISTHPQSASYPSSDREWSPSPSGSRPSTPKSDSELVSKSADRLTPKNNLEML 301                                                                                                  400
MaPAH1.1      GMAGALNGRHRRKRAARRKRRGPVHGVNSQDNLATETPSITAHVLSSLDPRLPLRPTARPALRPKANNGLGTLPNRRSSSMPNLKDFVGENNSLPSVPA
MaPAH1.2      GILSDSERHGRSTRKKFRRSKSHLSMEQRRHQLLEDIKQGAFLKPEESLANTQIERQTSRASRKTKRASIPSAWQGRRNRKRANSMPAIGEPDLAFPAYVA
ScPAH1        GSLSPTESSTTTPPDSVEERK-----------------------------CVEQRTKNFQQKLNKKLTEIHIPSKLDNNGDLLLDTEGYK---------
mouse-Lipin1  WLWGELPQAAKSSSPHKMKESSPLGSRKTPDKMNFQAIHSESSDTFSDQSPTMARGLLIHQSKAQTEMQFVNEEDLESLGAAAPPSPVAEELKAPYPNTA 401                                                                                                  500
MaPAH1.1      IMRRFPSKTLNSKFSARSDIKDGTSSSSSVASSPPPSVANQQSPKNRHHHHHHHKEHTEGSHPRRHSHKPSQQVQVKKPPPRSNPAVNALSDTELEYQTP
MaPAH1.2      RRP---------------------------------------------NHRRDAQANQTDVAMDDKPKPKRTARPSVMSDTEMEYESN
ScPAH1        -----------------------------------------------PN-----------------KNMMHDTDIQLK--
mouse-Lipin1  Q----------------------------------------------SSSKTDSPSRKKDKRSRHLGADGVYLDDLTDMDP 501                                                                                                  600
MaPAH1.1      RTTAATQESEWSNCNGSLPVKNDGLGTGEADHKEHHSSHPSIDIPAPRKPVLNEMEIDGTVYRLAISLCPGDEFGKDLEASEALFATNQVSFDEFAKDPL
MaPAH1.2      NVPASTQGKENTWGNGTLPVKQDNP----DEEDEIKEQITEEKAPEVPVEIEAKEFQMGSTKCRVALSLCGEDDFGKDIVASHKAFQRAQLTFEAFSKDPA
ScPAH1        --------Q-----------------------------------LI-----------------KDEFGNDSDISSFIKEDKNG---------
mouse-Lipin1  EVAALYFPKN----G-------DPGGLPKQASDNVARSANQSPQSVGGSGIDSGVESTSDSLRDLPSIAISLCGGLSDHREITKDAFLEQAVSYQQFADNP- 601                                                                                                  700
MaPAH1.1      KTENNKNLVCLINDRYFTWTAAGPYLSSLMLFRKPLSDETLHQLSAKDSRHLSDRLAVQDEPPTRFGALSRWLRGSQTSSQLSAMEQGQRQRTPSTNDAL
MaPAH1.2      AILADKRLVGYMDGRFYSWSNAVPQLAALLFFEHQPLSDAAS----ALDLKDQKAHAAEDRPSATRFGTISRWFR---------------KAPAGSASP
ScPAH1        ----NIKIVN----------------------------------------PYEHLTDLSPPG------------------TPPTMATSG
mouse-Lipin1  AIIDDPNLVKVGNKYYNWTTAAPLLLAMQAFQKPLP----------KAT---VESIMRDKMPKKGGR---------------WWFSWRGRNA 701                                                                                                  800
MaPAH1.1      QPAQLEESQALQSVKVESIKHTSGSHSSLLRAPKPMTRSTSLPIDEGIAGSISDEYAGSSPPTHSALK----SSRRYAKTLRLTSEQLKSLNLKKGANTLT
MaPAH1.2      SIADMASASSTTLAGGETAAVAVGSDDDEPLHNKALRSKSLPPLETGRTDDHSQSHVAVPALSEKAADGVPDQKRYAKTLRLTSEQLQSLGLKGANTVS
ScPAH1        SVLGLDAMESGSTLNSLSSSPSGSDTEDETSFSKEQSSKSEKTSKKGTAGSG----E--------------TEKRYIRTIRLTNDQLKCLNLTYGENDLK
mouse-Lipin1  TIKEESKPEQCLTGKGHNTGEQPAQLGLATRIKHESSSSDEEHAAAKPSGSS---------------HLSLLSNVSYKKTLRLTSEQLKSLKLKNGPNDVV 801                                                                                                  900
MaPAH1.1      FSVTSSYQGKAVCSAKLFLWDHDYQVVISDIDGTITKSDALGHIFTMAGKDWIHSGVAKLYTDIVNNGYHILYLTSRAIGQADYTRKYLKNYEQNNYQLP
MaPAH1.2      FSVTSSYQGTATCVAKIFLWDYDSQVVISDIDGTITKSDALGHIFAMAGRDWIHLGVAKLFTDIRSNGYHILYLTSRAIGQADYTRKYLQKVEQNSYQLP
ScPAH1        FSVD--H-GKAIVTSKLFVWRWDVPIVISDIDGTITKSDALGHVLAMIGKDWIHLGVAKLFSEISRNGYNILYLTARSAGQADTRSYLRSIEQNGSKLP
mouse-Lipin1  FSVYTTQYQGTCRCEGTIYLWNWDDKVIISDIDGTITRSDTLGHILPTLGKDWIHQGIAKLYHKVSQNGYKFLYCSARAIGMADWTRGYLHWVNERGTVLP
                                                        + + +

901                                                                                                 1000
MaPAH1.1      DGPVIMSPDRLMTAFHREVIMRKPEEFKMACLRDIRRLFCDR-----------NPFYAGFGNRITDALSYRSVNVPSSRIFTIDSGGEVKLELLS--SYK
MaPAH1.2      DGPVIMSPDRLFSAFHREVIIRKPEVFKMACLRDVKKLFGDR-----------NPFYAGFGNRITDALSYRSVNVPPSRIFTIDSYGEVKLELLS--AFK
ScPAH1        NGPVILSPDRTMAALRREVILKKPEVFKIACLNDIRSLYFEDSSDNEVDTEEKSTPFFAGFGNRITDALSYRTVGIPSSRIFTINTEGEVHMELLELAGYR
mouse-Lipin1  QGPLLLSPSSLFSALHREVIEKKPEKFKVQCLTDIKNLFFPN-----------TEPFYAAFGNRPADVYSYKQVGVSLNRIFTVNPKGELVQEHAK-TNI
```

Figure 5-2

```
              1001                                                                                    1100
MaPAH1.1     SSYLALNDLVNEIFPGKRQAPEFNDWNFWRAPLPDIELPVAPSHQYAPTAVPGEYNAQGYSAGPGRLGVIRSLTSSLTSAGPLKTRTAIPIFTSN-SPPP
MaPAH1.2     SSYLALNDLVNEIFPGQRVAPEFNDWNFWKSDLPRIDLPDLPIPNNNYTSGSSTSLLSSTTSVAKKVASLTSSSSSSNLLQPTSPTSPTGDFKNKRLSND
ScPAH1       SSYIHINELVDHFFP--PYS--LDSVDLRTN------TSMVPGSPPNRTLDNFDSEITSGRKTLFRGNQEEKFTDVNFWRDPLVDIDNLSDISNDDSDNI
mouse-Lipin1 SSYVRLCEVVDHVFPLLKRS---------------HSCDFP--------------CS-----------DTFSNFTFWREPLPPFENQDMHSASA----

1101                                                                                    1200
MaPAH1.1     PNSYPSAMKPHAPHQSQPASSSPQPP-ASAPSGLQIADRTRRLSLSLMRYSSHSAPTSAPVLRTLTDSSEPNVGIDSGDAGALSEGNQ-AGLEPNRSPHL
MaPAH1.2     RNTYAGVLSGRQDTWTSDDEYQDQQQRLIAGDSAPSTPGSELKAGQELKEDARKARSGSPSMLSALVPSRLIRAVRSGSISSQTNPVP-SSMRSSVIPHS
ScPAH1       DEDTDVSQQSNISRNRANSVKTAKVTKAPQRNVSGSTNNNEVLAASSDVENASDLVSSHSSSGSTPNKS----TMSKGDIGKQIYLELGSPLASPKLRYL
mouse-Lipin1 ----------------------------------------------------------------------------------------------

1201                                                                                    1300
MaPAH1.1     GSNTDGVFPLDVPVVKRKASGFSVSPPQLASRLSETVMPFLRRRASKLEQGQEQQQEQQQEQEQEREHDVQLGAAAEGEQLAYTREYGEFEAAAGYLAED
MaPAH1.2     PEMKGIIGSLPSPVSSFESGADVVRRMSIPSPPPLEGLLQTDEEVAQASSKALALQGSDTADLS-RESSVQAKSDVMDDLVAVKEEEEDETQQQRLLDAA
ScPAH1       DDMDDEDSNYNRTKSRRASSAAATSIDKEFKKLSVSKAGAPTRIVSKINVSNDVHSLGNSDTESRREQSVNETGRNQ-----LPHNSMDDKDLDSRVSDE
mouse-Lipin1 ----------------------------------------------------------------------------------------------

1301                        1355
MaPAH1.1     HELGEDEEDEGEGADGYVGYSGEEDEGLEEDQLEGEEDEDEDDDDVELNIDAPFL
MaPAH1.2     YVDEYVDEEDEEGYDGYDEQG--------EDEMDEEDEEDEYLDEIEETLEEPFL
ScPAH1       FDDDEFDEDEFED-----------------------------------------
mouse-Lipin1 ----------------------------------------------------
```

|      | 1601 | 1700 |
| ---- | ---- | ---- |
| MaPAH1.1 | TCATCCATCAATCGACATTCCAGCCCCACGGAAACCTGTGTTGAACGAGATGGAGATTGACGGGACTGTGTACAGACTCGCCATCAGCTTGTGTCCGGGT | |
| MaPAH1.2 | AGAAAAGGCGCCCGAAGTTCCTGT-----GGAGAT-TGAGGCAAAGGAGTTTCAGATGGGATCAACAAAATGCCGCGTAGCGCTCAGTCTCTGCGGAGAG | |

|      | 1701 | 1800 |
| ---- | ---- | ---- |
| MaPAH1.1 | GATGAATTCGGAAAAGATTTGGAAGCCAGCGAAGCATTGTTTGCCACCAATCAGGTTTCGTTCGATGAGTTCGCGAAAGACCCACTCAAGACTCTCAATA | |
| MaPAH1.2 | GATGACTTTGGAAAGGACATTGTTGCTAGCCACAAGGCTTTTCAAAGAGCCCAGTTGACCTTTGAGGCATTCTCCAAAGATCCCGCGGCAATTCTGGCCG | |

|      | 1801 | 1900 |
| ---- | ---- | ---- |
| MaPAH1.1 | ACAAGAATTTCGTCTGCCTGATCAATGACCGGTATTTTACTTGGACAGCTGCCGGACCATATCTTTCCTCACTGATGCTCTTCGGGAAGCCTCTCTCTGA | |
| MaPAH1.2 | ACAAGAGACTTGTGTGTTACATGGATGGGCGGTTTTATTGGTGGAGTAATGCCGTTCCTCACCTCGCAGGCCTTCTCTTCTTCCACCAGCCTCTTTCAGA | |

|      | 1901 | 2000 |
| ---- | ---- | ---- |
| MaPAH1.1 | CGAAACGGTCCATCAGCTTTGACCG--AAGGACTCGCCGGCATCTATCAGATCGACTCGCTGTGCAAGATGAGCCCGCAAGCCGTTTCGGCGGTCTCTCCA | |
| MaPAH1.2 | CG-----CGGGCTCTGCTCTGGACCTCAAGGACCAAAAGGCAC-ATGCGGCCGA------GGA-CAGACCGAGCGCC-AGCGGTTTTGGCACAATCTCCA | |

|      | 2001 | 2100 |
| ---- | ---- | ---- |
| MaPAH1.1 | GATGGCTAAGGGGATCACAAACGTCGTCCCAATTGAGCGCGATGGAG-CAAGGGCAAAGACAACGTACTCCCAGTACCAACGATGCCTTGCAGCCTGCTC | |
| MaPAH1.2 | GATGGTTCAGG-------AAGGCGCCTGC--AGGCAGGCGCGTCCCCCTGTATTGCAGATATGGC-----CTCAGCATCCTCGA--C-----AACCCTTGC | |

|      | 2101 | 2200 |
| ---- | ---- | ---- |
| MaPAH1.1 | AGTTAGAGGAGAGTCAAGCTTTACAGAGCGTGAAAGTCGAATCGATTAAGCACACTTCCGGATCACATTCATCACTT-CTACGCGCT-CCTAAACCAATG | |
| MaPAH1.2 | AGGTCGTG-AGACCCGCCGCTGT-CGCTGTGGGA----TCAGAT-GACGACGAGCCCTTGCACAACAAGGCCCTGCGTAGCAAATCCCTGCCCCCACTGGAG | |

|      | 2201 | 2300 |
| ---- | ---- | ---- |
| MaPAH1.1 | ACTCGTAGCACGCTCTCTGCCGATCGACGAAGGGATCGCGGGTCTATATCAGACGAGTACGCTGGAAGCTCGGCTCCGACACATTCTGCGCTCAAGAGCA | |
| MaPAH1.2 | ACTCGCCGGACC-----GAGGACC-AC--AGTCAGAGCCATGTCGCTCT---ACCTGCGCTTTCGGACAAAGCAGGCGACG------GTGTCGCAGATCA | |

|      | 2301 | 2400 |
| ---- | ---- | ---- |
| MaPAH1.1 | GTAGACGGTATGCGAAAACGGCTTCGCTTGACATCTGAACAGTTGAAATCACTAAATTTGAAAAAAGGCGCCAATAGATTGACGTTTCAGTAACGTCAAG | |
| MaPAH1.2 | GAAG-CGCTATGCCAAGACGCTGCCGGCTCACCTCGGAACAGCTTCAATCCTTGGGTTTGAAAAAGGGCGCCAACAGGGTCTCGTTCTCAGTGACATCGTC | |

|      | 2401 | 2500 |
| ---- | ---- | ---- |
| MaPAH1.1 | TTATCAAGGCAAAGCAGTTTGTTCCGCCAAATTGTTTCTGTGGGACCATGACTACCAAGTCGTCATATCGGACATTGATGGCACGATTACAAAGTCGGAC | |
| MaPAH1.2 | CTACCAGGGAACTGCAACTTGTGTAGCCAAGATCTTTTGTGGGATTACGACTCCCAGGTGGTGATCTCGGATATTGATGGTACAATCACAAAGTCAGAT | |

|      | 2501 | 2600 |
| ---- | ---- | ---- |
| MaPAH1.1 | GCTCTCGGACACATCTTTACCATGGCAGGAAAGGATTGGACCCATTCGGGTGTCGCCAAACTTTACACGGACATCGTCAACAATGGGTATCATATTTTGT | |
| MaPAH1.2 | GCCCTCGGCCACATTTTTGCCATGGCCGGTCGCGACTGGACGCATCTCGGTGTCGCCAAGCTGTTCACAGATATTCGCAGCAACGGATATCACATCCTGT | |

|      | 2601 | 2700 |
| ---- | ---- | ---- |
| MaPAH1.1 | ACTTGACCTCAAGGGCCATTGGACAGGGAGACTACACACGAAAGTACCTCAAGAACGTGGAGCAAAATAACTACCAGTTACCGGATGGACCCGTGATCAT | |
| MaPAH1.2 | ACCTGACCTCCCGAGCCATTGGCCAGGCAGACTACACACGCAAGTATCTTCAGAAGGTCGAGCAAAACAGTTACCAGCTCCCGGATGGCCGTGTCATCAT | |

|      | 2701 | 2800 |
| ---- | ---- | ---- |
| MaPAH1.1 | GAGCCCTGATCGCTTGATGACCGCCTTCCACAGGGAGGTGATTATGAGGAAGCCAGAAGAATTCAAGATGGCATGTCTGCCGTGACATTCGGAGGCTGTTT | |
| MaPAH1.2 | GAGTCCAGACCGTCTGTTCTCTGCCTTCCATCGTGAGGTGATTATCCGGAAAACCAGAGGTGTTCAAGATGGCCTGTCTGCGTGATCGTGAAGAAGCTGTTT | |

|      | 2801 | 2900 |
| ---- | ---- | ---- |
| MaPAH1.1 | GGAGATCGCAACCCCTTCTATGCGCGGGTTTGGAAACAGAATCACGGACGGACTGTCCTACAGGAGCGTTAATGTCCCCTCATCTCGGATATTTACAATTG | |
| MaPAH1.2 | GGGGACAGGAACCCGGTTCTATGCTGGATTTGGAAAGCCGGATCACGGACGGCCTCTCCTACCGCAGTGTCAACGTTCCACCCTCCCGAATCTTCACCATTG | |

|      | 2901 | 3000 |
| ---- | ---- | ---- |
| MaPAH1.1 | ATTCGGGAGGTGAAGTCAAGCTGGAGCTCCTCAGCAGCTACAAATCATCATATCTCCGGTTGAACGATCTCGTGAATGAGATCTTTCCAGGAAAAAGACA | |
| MaPAH1.2 | ACTCTTATGGTGAGGTGAAGTTGGAGCTGCTCAGTGCTTTCAAGTCTTCATACTTGGCTTTGAATGACCTCGTCAATGAGATCTTCCCAGGACAACGAGT | |

|      | 3001 | 3100 |
| ---- | ---- | ---- |
| MaPAH1.1 | GGCACGCGAGTTCAATGACTGGAACTTTTGGCGGGCGCCCCTTGCCAGATATCGAGCTTCCAGTTG-CGCCGTCTC-ATCAATACGCCCCTACAGG-GGTG | |
| MaPAH1.2 | TGCACGCGAGTTCAACGACTGGAACTTTTGGAAAATCGGATTTACGACGGATTGATCTCCGTGACTCTGCCGATCCGCAAGCAATAATTA-TACATGAGGAT | |

|      | 3101 | 3200 |
| ---- | ---- | ---- |
| MaPAH1.1 | CCGGGCGAGTACAATGCACAAGGATATTCTGCAGGTCCTGCCGGTTGGGAGTGATACGGAGCCTTACCAGTTCCCTCACCT----CAGC-AGGACCGGCT | |
| MaPAH1.2 | CTTCGACATCGCTCCTGTCATCCACCACTAGCGTTGGCCAAGAAGGTCGCGTCTTTGACCAGCTCTTCATCGACGTCGAACCTTCTCCAGCCAACGTCGCC | |

Figure 6-3

```
            3201                                                                                    3300
MaPAH1.1    CAAGACGAGGACCGCT-ATCCCAATTTTTACC-----TCAAATT-CGCCCCCTCCTCCGAATTCCTACCCATCGGCGATGAAGCCCATGCACC-GCATC
MaPAH1.2    CACTAGCCCTACGGAGATTTCAAGAACAACCGCCTGTCTAATGACAGAAACACGTATGCGGGCCTCCTTTCAGGACGTCAGGACACATGGACCAGCGAT 3301                                                                                    3400
MaPAH1.1    AGTCCCAACCAGCCTGCTCCTC----GCCTCAACCCCCGCA-TCAGCGCCGTCAGGACTGCAGATCGCTGATAGGACCCGTCGACTCTCGCTGTCGTTG-
MaPAH1.2    GATGAATATCAGGATCAACAGCAGCGACTGATCGCGGGTGACTCTGCGCCGTCA--ACGCCAGGAT-CAGAGTTGAAGGCAGGACAGGAGCTGAAGGAGC 3401                                                                                    3500
MaPAH1.1    ATGCGATATAGCAGCCATTCAGCTCCC------ACGTCCGGCCAGTTTTGAGAACTTTGACCGACAGTTCCGAGCCCAATGTCGGCATTGACAGCGGTGA
MaPAH1.2    ATGCAAGGAAGGCACGATCTGGCTCGCCATCGATGCTCTGTGCTCTTGTTCCATCGGCGGTTAATCCGCGCAGTGAGGACTGCCAGCAT----CAGCAGTCA 3501                                                                                    3600
MaPAH1.1    TGCAGGCGCTCTCTCTGAGGGGAATCAG-GCAGGTTTAGAGCCAAATCGCTCACCTCACTTGGGATCCAACACTGATGGCGTTTTCCCACTGGACGTTCC
MaPAH1.2    GAGCAACCCTGTGCCCTCGTCGATGCGGAGTTCGGTTACACCGCATTCGCCCGAGATGAAAGGGATCAT---CGGGTCGC----TGCCGTCACCAGTGTCT 3601                                                                                    3700
MaPAH1.1    TGTTGTGA-AGAGAAAGGCATCTGGTTTCTCGGTCTCACCGCCCCAGCTTGCCAGTCGACTAAGTGAGACTGTAATGCCTTTTCTTCGCCGACCAGCATC
MaPAH1.2    TCGTTTGAGAGCGGTGCGGATCTGCTGCGTCGGA-TGTCCATTCC--CTCGCC--TCCACC--GT-----TGCAGGGGCTGCTCCAGACGGATCAGG----

3701                                                                                    3800
MaPAH1.1    CAAGTTGGAGCAGGGGCAGGAGCACAGCAGGAACAGCAGCAGGAAGAGGAACAGGA-ACGAGAGCATGATGTCCAGCTGGGTGCAGCAGCTGAAGGGGA
MaPAH1.2    --AGGTGGCTCAGGCATCGAGCAAGGCCGCTGGCGCTTCAG--GGATCGGACACAGCAGATTTGAGCAGAGAG---AGCAGTGTTCAG-GCCAACAGTGA 3801                                                                                    3900
MaPAH1.1    GCAGCTTGCTTACACTCGAGAGTACGGGGAAGAAGAAGCCGCTGCTGGATATCTGGCGGAGGACCATGAACTCGGAG-AGGATGAACAGGATGAAGGAGA
MaPAH1.2    TGTGATGGACGACCTTGTGGCGGTCAAGGAGGAAGAGGAGGACGAGACCGATCAG-CAGCGGTTGCTGGATGCAGCGTATGTGGATGAGTATGT-GGATG 3901                                                                                    4000
MaPAH1.1    AGGAGCAGATGCGATATGTTGGTTATTCTGGACAAGAGGATGAAGGTCTGGAAGAAGATCAGCTCGACGGTGAGGAAGACGAGGATGAGGATGACGATGAT
MaPAH1.2    AGGAG--GATG---AGGACGGATATGATGGATATGACGAGCAGGGT------GAGGATGAGATGGACGAGGAGGATGAGGAGGACGAGTATCTCGATGAG 4001           4033
MaPAH1.1    GTAGAGCTCAACATTGACGCTCCGTTCCTATGA
MaPAH1.2    ATTGACGAGACTCTGGACGAGCCCGTTCCTGTAG
```

Figure 7

```
         1                                                                                                  100
PAH1-1   MQSVGSFFSTVSRFYNELNPATLSGAIDVVVVEQADGELACSPFHVRFGKLSILRPQEKVVEVTVNGRVVDFPMKVGDAGEAFFVFETEQDVPEEFATSP
PAH1-2   MYSVGNFFSTVTKFYNEINPATLSGAIDIIVVQQANGDLACSPFHVRFGKLSVLRPQEKVVEVRVNGEVIAFPMKVGDAGEAFFVLETDDYVPDEFATSP 101                                                                                                200
PAH1-1   LAGPNTDKVEEDIDYLDLAEGHSTVTYPPDDIVLDAGYVSAHSGHGSEFEEDERADLSPEFDKKPDYASAVKYGGTNGQGRHLGSANEATTSVHAFMERQ
PAH1-2   IAGPSDEADLAPVDYFDLNGHPHCSQDQKRRQHQQQQVLEGMSGQYPQGTEDDAPLDNGYVSAASGHGSAFEESLKDDS----DHESVFSATSPGSAERI 201                                                                                                300
PAH1-1   VQRWSLTMSLPPSPVLKSRDIMENFQPIDSAGPFDNSREDSGRLLAPETIAVSNGGSSGSLFHPKEGMIMDMTGYKTEDSDLNSDASDEHDVGMAGALNG
PAH1-2   AADSNTKDTALDLPGSFGPTVYTNTIKNKDSINFPVDAIFPTVAHEEQDMALIKDQQGSRSSRRRSEVLFDMTGYKTDSCSDSSDDEDGLPRGILSDSER 301                                                                                                400
PAH1-1   RHRRKRAARRKRRGPVHGVNSQDNLATETPSITAHVLSSLDPRLPLRPTARPALRPKANNGLGTLPNRRSSSMPNLKDFVGENNSLSPSVPAIMRRFPSK
PAH1-2   HGRSTRKKFRRSKSHLSMEQRHQLLEDIKQGAFLKPEESLANTQIERQTSRASRKTKRASIPSAWQGRRNRKRANSMPAIGEPDLAFPAYVARRP-----

401                                                                                                500
PAH1-1   TLNSKFSARSDIKDGTSSSSSVASSPPPSVANQQSPKNRHHHHHHHKEHTEGSHPRRHSHKPSQQVQVKKPPPRSNPAVNALSDTELEYQTPRTTAATQE
PAH1-2   -----------------------------------------------NHRRDAQANQTDVAMDDKPKPKRTARPSVMSDTEMEYESNNVPASTQG 501                                                                                                600
PAH1-1   SEWSWGWGSLPVKNDGLGTGEADHKEHHSSHPSIDIPAPRKPVLNEMEIDGTVYRLAISLCPGDEFGKDLEASEALFATNQVSFDEFAKDPLKTLNNKNL
PAH1-2   KEWTWGWGTLPVKQDNP---DEEDEIKEQITEEKAPEVPVEIEAKEFQMGSTKCRVALSLCGEDDFGKDIVASHKAFQRAQLTFEAFSKDPAAILADKRL 601                                                                                                700
PAH1-1   VCLINDRYFTWTAAGPYLSSLMLFRKPLSDETLHQLSAKDSRHLSDRLAVQDEPPTREGALSRWLRGSQTSSQLSAMEQGQRQRTPSTNDALQPAQLEES
PAH1-2   VCYMDGRFYSWSNAVPQLAALLFFHQPLSDAAS----ALDLKDQKAHAAEDRPSATRFCGTISRWFR-----------------KAPAGSASPSIADMASA 701                                                                                                800
PAH1-1   QALQSVKVESIKHTSGSHSSLLRAPKPMTRSTSLPIDEGIAGSISDEYAGSSPPTHSALK---SSRRYAKTLRLTSEQLKSLNLKKGANTLTFSVTSSYQ
PAH1-2   SSTTLAGGETAAVAVGSDDDEPLHNKALRSKSLPPLETGRTDDHSQSHVAVPALSEKAADGVPDQKRYAKTLRLTSEQLQSLGLKKGANTVSFSVTSSYQ 801                                                                                                900
PAH1-1   GKAVCSAKLFLWDHDYQVVISDIDGTITKSDALGHIFTMAGKDWTHSGVAKLYTDIVNNGYHILYLTSRAIGQADYTRKYLKNVEQNNYQLPDGPVIMSP
PAH1-2   GTATCVAKIFLWDYDSQVVISDIDGTITKSDALGHIFAMAGRDWTHLGVAKLFTDIRSNGYHILYLTSRAIGQADYTRKYLQKVEQNSYQLPDGPVIMSP 901                                                                                               1000
PAH1-1   DRLMTAFHREVIMRKPEEFKMACLRDIRRLFGDRNPFYAGFGNRITDALSYRSVNVPSSRIFTIDSGGEVKLELLSSYKSSYLALNDLVNEIFPGKRQAP
PAH1-2   DRLFSAFHREVIIRKPEVFKMACLRDVKKLFGDRNPFYAGFGNRITDALSYRSVNVPPSRIFTIDSYGEVKLELLSAFKSSYLALNDLVNEIFPGQRVAP 1001                                                                                              1100
PAH1-1   EFNDWNFWRAPLPDIELPVAPSHQYAPTAVPGEYNAQGYSAGPGRLGVIRSLTSSLTSAGPLKTRTAIPIFTSN-SPPPPNSYPSAMKPHAPHQSQPASS
PAH1-2   EFNDWNFWKSDLPRIDLPDLPIPNNNYTSGSSTSLLSSTTSVAKKVASLTSSSSSNLLQPTSPTSPTGDFKNKRLSNDRNTYAGVLSGRQDTWTSDDEY 1101                                                                                              1200
PAH1-1   SPQPP-ASAPSGLQIADRTRRLSLSLMRYSSHSAPTSAPVLRTLTDSSEPNVGIDSGDAGALSEGNQAGLEPNRSPHLGSNTDGVFPLDVPVVKRKASGF
PAH1-2   QDQQQRLIAGDSAPSTPGSELKAGQELKEDARKARSGSPSMLSALVPSRLIRAVRSGSISSQTNPVPSSMRSSVTPHSPEMKGIIGSLPSPVSSFESGAD 1201                                                                                              1300
PAH1-1   SVSPPQLASRLSETVMPFLRRRASKLEQGQEQQQEQQQEQEQEREHDVQLGAAAEGEQLAYTREYGEEEAAAGYLAEDHELGEDEEDEGEGADGYVGYSG
PAH1-2   VVRRMSIPSPPPLEGLLQTDEEVAQASSKALALQGSDTADLS-RESSVQAKSDVMDDLVAVKEEEEDETDQQRLLDAAYVDEYVDEEDEEGYDGYDEQG- 1301          1333
PAH1-1   EEDEGLEEDQLEGEEDEDEDDDDVELNIDAPFL
PAH1-2   -------EDEMDEEDEEDEYLDEIEETLEEPFL
```

PHOSPHATIDIC ACID PHOSPHATASE GENE AND USE THEREOF

TECHNICAL FIELD

The present invention relates to a novel phosphatidic acid phosphatase gene and use thereof.

BACKGROUND ART

Fatty acids containing two or more unsaturated bonds are collectively referred to as polyunsaturated fatty acids (PUFAs) and are known to include arachidonic acid, dihomo-γ-linolenic acid, eicosapentaenoic acid, docosahexaenoic acid, etc. Some of these polyunsaturated fatty acids cannot be synthesized in the animal body, and such polyunsaturated fatty acids need to be ingested from foods as essential fatty acids. The polyunsaturated fatty acids are widely distributed. For example, arachidonic acid is isolated from lipids extracted from suprarenal gland and liver of animals. However, the amounts of these polyunsaturated fatty acids contained in animal organs are small, and the polyunsaturated fatty acids extracted and isolated from animal organs only are insufficient for a large amount of supply thereof. Thus, microbial techniques have been developed for obtaining polyunsaturated fatty acids by culturing various microorganisms. In particular, microorganisms in the genera *Mortierella* are known to produce lipids containing polyunsaturated fatty acids such as arachidonic acid.

Other attempts have also been made to produce polyunsaturated fatty acids in plants. Polyunsaturated fatty acids are known to constitute reserve lipids such as triacylglycerol (also referred to as triglyceride or TG) and accumulate within microorganism cells or plant seeds.

Triacylglycerol as a reserve lipid is generated in the body as follows: An acyl group is introduced into glycerol-3-phosphate by glycerol-3-phosphate acyltransferase to generate lysophosphatidic acid. An acyl group is introduced into the lysophosphatidic acid by lysophosphate acyltransferase to generate phosphatidic acid. The phosphatidic acid is dephosphorylated by phosphatidic acid phosphatase to generate diacylglycerol. An acyl group is introduced into the diacylglycerol by diacylglycerol acyltransferase to generate triacylglycerol.

In this pathway, phosphatidic acid (hereinafter, also referred to as "PA" or 1,2-diacyl-sn-glycerol-3-phosphate) is a precursor of triacylglycerol and is also a biosynthetic precursor of diacyl glycerophospholipid. In yeast cells, CDP diacylglycerol (CDP-DG) is synthesized from PA and cytidine 5'-triphosphate (CTP), by phosphatidate cytidyltransferase, and is biosynthesized into various phospholipids.

As described above, the reaction of biosynthesizing diacylglycerol (hereinafter, also referred to as "DG") through dephosphorylation of PA is known to be catalyzed by phosphatidic acid phosphatase (E.C. 3.1.3.4, hereinafter, also referred to as "PAP"). This PAP is known to be present in all organisms from bacteria to vertebrates.

Yeast (*Saccharomyces cerevisiae*), which is a fungus, has two types of PAPs (Non-Patent Literatures 1, 2, and 7). One is a $Mg^{2+}$-dependent PAP (PAP1), and the other is a $Mg^{2+}$-independent PAP (PAP2). A PAH1 gene is known as a gene encoding PAP1 (Non-Patent Literatures 3 to 5). A pah1Δ variant also shows a PAP1 activity, which suggests there are other genes exhibiting the PAP1 activity. In the pah1Δ variant, the nuclear membrane and the ER membrane are abnormally dilated, and expression of important genes for biosynthesis of phospholipids is abnormally enhanced (Non-Patent Literature 6).

As genes encoding PAP2, a DPP1 gene and a LPP1 gene are known and exhibit most PAP2 activities in yeast. The enzymes encoded by these genes have broad substrate specificity and act also on, for example, diacylglycerol pyrophosphate (DGPP), lysophosphatidic acid, sphingoid base phosphate, and isoprenoid phosphate to dephosphorylate them.

A lipid-producing fungus, *Mortierella alpina*, is known to have a MaPAP1 gene, which is a $Mg^{2+}$-independent PAP2 homolog (Patent Literature 1).

Existance of gene homologs that probably encode PAP1 family enzymes or PAP2 family enzymes in other bacteria is known in the art, but their functions have not been elucidated.

CITATION LIST

Patent Literature

Patent Literature 1: International Publication No. WO2009/008466

Non-Patent Literature

Non-Patent Literature 1: Biochem. Biophys. Acta, 1348, 45-55, 1997
Non-Patent Literature 2: Trends Biochem. Sci., 31(12), 694-699, 2006
Non-Patent Literature 3: EMBO J., 24, 1931-1941, 2005
Non-Patent Literature 4: J. Biol. Chem., 281(14), 9210-9218, 2006
Non-Patent Literature 5: J. Biol. Chem., 281(45), 34537-34548, 2006
Non-Patent Literature 6: J. Biol. Chem., 282(51), 37026-37035, 2007
Non-Patent Literature 7: J. Biol. Chem., 284(5), 2593-2597, 2009

SUMMARY OF INVENTION

Technical Problem

Most of the PAP genes previously reported, however, have not been investigated for that these genes introduced into host cells and expressed therein can vary the proportion of fatty acids in the fatty acid composition produced by the host cells. There is a demand for identification of a novel gene that can produce fat having an intended composition of fatty acids or an increase in content of an intended fatty acid by introducing the gene into a host cell or expressing the gene.

It is an object of the present invention to provide a protein or a nucleic acid that allows host cells to produce fat having an intended composition of fatty acids or an increase in content of an intended fatty acid by expressing the protein in the host cells or introducing the nucleic acid into the host cells.

Solution to Problem

The present inventors have diligently studied to solve the above-mentioned problems. That is, the inventors have analyzed the genome of lipid-producing fungus, *Mortierella alpina*, and extracted sequences having homology to known Mg²⁺-dependent phosphatidic acid phosphatase (PAP1) genes from the genome. Further, cloning of the full-length cDNA through cDNA library screening or PCR were conducted to obtain the entire open reading frame (ORF) encoding PAP, and the gene were introduced into host cells having high proliferative ability, such as yeast. As a result, the inventors have found that the protein encoded by the cloned cDNA has a phosphatidic acid phosphatase activity and that introduction of the cDNA to yeast enhances the production of reserve lipids, triacylglycerol, in the yeast. Thus, cloning of a gene related to a novel phosphatidic acid phosphatase (PAP) has been successfully achieved, and the present invention has been accomplished. That is, the present invention is as follows.

(1) A nucleic acid according to any one of (a) to (g) below:

(a) a nucleic acid comprising a nucleotide sequence encoding a protein that consists of an amino acid sequence having deletion, substitution, or addition of one or more amino acids in the amino acid sequence set forth in SEQ ID NO: 2 or SEQ ID NO: 7 and has a phosphatidic acid phosphatase activity;

(b) a nucleic acid comprising a nucleotide sequence that is hybridizable with a nucleic acid consisting of a nucleotide sequence complementary to the nucleotide sequence set forth in SEQ ID NO: 1 or SEQ ID NO: 6 under stringent conditions and encodes a protein having a phosphatidic acid phosphatase activity;

(c) a nucleic acid comprising a nucleotide sequence which consists of a nucleotide sequence having an identity of 70% or more with the nucleotide sequence set forth in SEQ ID NO: 1 or SEQ ID NO: 6 and encodes a protein having a phosphatidic acid phosphatase activity;

(d) a nucleic acid comprising a nucleotide sequence encoding a protein that consists of an amino acid sequence having an identity of 70% or more with the amino acid sequence set forth in SEQ ID NO: 2 or SEQ ID NO: 7 and has a phosphatidic acid phosphatase activity;

(e) a nucleic acid comprising a nucleotide sequence that is hybridizable with a nucleic acid consisting of a nucleotide sequence complementary to a nucleotide sequence encoding a protein consisting of the amino acid sequence set forth in SEQ ID NO: 2 or SEQ ID NO: 7 under stringent conditions and encodes a protein having a phosphatidic acid phosphatase activity;

(f) a nucleic acid comprising a nucleotide sequence that is hybridizable with a nucleic acid consisting of a nucleotide sequence complementary to the nucleotide sequence set forth in SEQ ID NO: 5 or SEQ ID NO: 10 under stringent conditions and includes an exon encoding a protein having a phosphatidic acid phosphatase activity; and (g) a nucleic acid comprising a nucleotide sequence which consists of a nucleotide sequence having an identity of 70% or more with the nucleotide sequence set forth in SEQ ID NO: 5 or SEQ ID NO: 10 and includes an exon encoding a protein having a phosphatidic acid phosphatase activity.

(2) The nucleic acid according to aspect (1), wherein the nucleic acid is any one of (a) to (g) below:

(a) a nucleic acid comprising a nucleotide sequence encoding a protein that consists of an amino acid sequence having deletion, substitution, or addition of 1 to 130 amino acids in the amino acid sequence set forth in SEQ ID NO: 2 or SEQ ID NO: 7 and has a phosphatidic acid phosphatase activity;

(b) a nucleic acid comprising a nucleotide sequence that is hybridizable with a nucleic acid consisting of a nucleotide sequence complementary to the nucleotide sequence set forth in SEQ ID NO: 1 or SEQ ID NO: 6 under conditions of 2×SSC at 50° C. and encodes a protein having a phosphatidic acid phosphatase activity;

(c) a nucleic acid comprising a nucleotide sequence which consists of a nucleotide sequence having an identity of 90% or more with the nucleotide sequence set forth in SEQ ID NO: 1 or SEQ ID NO: 6 and encodes a protein having a phosphatidic acid phosphatase activity;

(d) a nucleic acid comprising a nucleotide sequence encoding a protein that consists of an amino acid sequence having an identity of 90% or more with the amino acid sequence set forth in SEQ ID NO: 2 or SEQ ID NO: 7 and has a phosphatidic acid phosphatase activity;

(e) a nucleic acid comprising a nucleotide sequence that is hybridizable with a nucleic acid consisting of a nucleotide sequence complementary to a nucleotide sequence encoding a protein consisting of the amino acid sequence set forth in SEQ ID NO: 2 or SEQ ID NO: 7 under conditions of 2×SSC at 50° C. and encodes a protein having a phosphatidic acid phosphatase activity;

(f) a nucleic acid comprising a nucleotide sequence that is hybridizable with a nucleic acid consisting of a nucleotide sequence complementary to the nucleotide sequence set forth in SEQ ID NO: 5 or SEQ ID NO: 10 under conditions of 2×SSC at 50° C. and includes an exon encoding a protein having a phosphatidic acid phosphatase activity; and (g) a nucleic acid comprising a nucleotide sequence which consists of a nucleotide sequence having an identity of 90% or more with the nucleotide sequence set forth in SEQ ID NO: 5 or SEQ ID NO: 10 and includes an exon encoding a protein having a phosphatidic acid phosphatase activity.

(3) A nucleic acid according to any one of (a) to (d) below:

(a) a nucleic acid comprising the nucleotide sequence set forth in SEQ ID NO: 1 or SEQ ID NO: 6 or a fragment thereof;

(b) a nucleic acid comprising a nucleotide sequence encoding a protein consisting of the amino acid sequence set forth in SEQ ID NO: 2 or SEQ ID NO: 7 or a fragment thereof;

(c) a nucleic acid comprising the nucleotide sequence set forth in SEQ ID NO: 4 or SEQ ID NO: 9 or a fragment thereof; and (d) a nucleic acid comprising the nucleotide sequence set forth in SEQ ID NO: 5 or SEQ ID NO: 10 or a fragment thereof.

(4) A nucleic acid according to any one of (a) to (g) below:

(a) a nucleic acid comprising a nucleotide sequence encoding a protein that consists of an amino acid sequence having deletion, substitution, or addition of one or more amino acids in the amino acid sequence set forth in SEQ ID NO: 2 or SEQ ID NO: 7 and has an activity that enhances generation of diacylglycerol (DG) and/or triglyceride (TG) from phosphatidic acid (PA) in a PAH1-deficient yeast strain;

(b) a nucleic acid comprising a nucleotide sequence that is hybridizable with a nucleic acid consisting of a nucleotide sequence complementary to the nucleotide sequence set forth in SEQ ID NO: 1 or SEQ ID NO: 6 under stringent conditions and encodes a protein having an activity that enhances generation of DG and/or TG from PA in a PAH1-deficient yeast strain;

(c) a nucleic acid comprising a nucleotide sequence which consists of a nucleotide sequence having an identity of 70% or more with the nucleotide sequence set forth in SEQ ID NO: 1 or SEQ ID NO: 6 and encodes a protein having an activity that enhances generation of DG and/or TG from PA in a PAH1-deficient yeast strain;

(d) a nucleic acid comprising a nucleotide sequence encoding a protein that consists of an amino acid sequence having an identity of 70% or more with the amino acid sequence set forth in SEQ ID NO: 2 or SEQ ID NO: 7 and has an activity that enhances generation of DG and/or TG from PA in a PAH1-deficient yeast strain;

(e) a nucleic acid comprising a nucleotide sequence that is hybridizable with a nucleic acid consisting of a nucleotide sequence complementary to a nucleotide sequence encoding a protein consisting of the amino acid sequence set forth in SEQ ID NO: 2 or SEQ ID NO: 7 under stringent conditions and encodes a protein having an activity that enhances generation of DG and/or TG from PA in a PAH1-deficient yeast strain;

(f) a nucleic acid comprising a nucleotide sequence that is hybridizable with a nucleic acid consisting of a nucleotide sequence complementary to the nucleotide sequence set forth in SEQ ID NO: 5 or SEQ ID NO: 10 under stringent conditions and includes an exon encoding a protein having an activity that enhances generation of DG and/or TG from PA in a PAH1-deficient yeast strain; and (g) a nucleic acid comprising a nucleotide sequence which consists of a nucleotide sequence having an identity of 70% or more with the nucleotide sequence set forth in SEQ ID NO: 5 or SEQ ID NO: 10 and includes an exon encoding a protein having an activity that enhances generation of DG and/or TG from PA in a PAH1-deficient yeast strain.

(5) The nucleic acid according to aspect (4), wherein the nucleic acid is any one of (a) to (g) below:

(a) a nucleic acid comprising a nucleotide sequence that encoding a protein that consists of an amino acid sequence having deletion, substitution, or addition of 1 to 130 amino acids in the amino acid sequence set forth in SEQ ID NO: 2 or SEQ ID NO: 7 and has an activity that enhances generation of diacylglycerol (DG) and/or triglyceride (TG) from phosphatidic acid (PA) in a PAH1-deficient yeast strain;

(b) a nucleic acid comprising a nucleotide sequence that is hybridizable with a nucleic acid consisting of a nucleotide sequence complementary to the nucleotide sequence set forth in SEQ ID NO: 1 or SEQ ID NO: 6 under conditions of 2×SSC at 50° C. and encodes a protein having an activity that enhances generation of DG and/or TG from PA in a PAH1-deficient yeast strain;

(c) a nucleic acid comprising a nucleotide sequence which consists of a nucleotide sequence having an identity of 90% or more with the nucleotide sequence set forth in SEQ ID NO: 1 or SEQ ID NO: 6 and encodes a protein having an activity that enhances generation of DG and/or TG from PA in a PAH1-deficient yeast strain;

(d) a nucleic acid comprising a nucleotide sequence encoding a protein that consists of an amino acid sequence having an identity of 90% or more with the amino acid sequence set forth in SEQ ID NO: 2 or SEQ ID NO: 7 and has an activity that enhances generation of DG and/or TG from PA in a PAH1-deficient yeast strain;

(e) a nucleic acid comprising a nucleotide sequence that is hybridizable with a nucleic acid consisting of a nucleotide sequence complementary to a nucleotide sequence encoding a protein consisting of the amino acid sequence set forth in SEQ ID NO: 2 or SEQ ID NO: 7 under conditions of 2×SSC at 50° C. and encodes a protein having an activity that enhances generation of DG and/or TG from PA in a PAH1-deficient yeast strain;

(f) a nucleic acid comprising a nucleotide sequence that is hybridizable with a nucleic acid comprising a nucleotide sequence complementary to the nucleotide sequence set forth in SEQ ID NO: 5 or SEQ ID NO: 10 under conditions of 2×SSC at 50° C. and includes an exon encoding a protein having an activity that enhances generation of DG and/or TG from PA in a PAH1-deficient yeast strain; and (g) a nucleic acid comprising a nucleotide sequence which consists of a nucleotide sequence having an identity of 90% or more with the nucleotide sequence set forth in SEQ ID NO: 5 or SEQ ID NO: 10 and includes an exon encoding a protein having an activity that enhances generation of DG and/or TG from PA in a PAH1-deficient yeast strain.

(6) A protein according to (a) or (b) below:

(a) a protein consisting of an amino acid sequence having deletion, substitution, or addition of one or more amino acids in the amino acid sequence set forth in SEQ ID NO: 2 or SEQ ID NO: 7 and having a phosphatidic acid phosphatase activity; and (b) a protein consisting of an amino acid sequence having an identity of 70% or more with the amino acid sequence set forth in SEQ ID NO: 2 or SEQ ID NO: 7 and having a phosphatidic acid phosphatase activity.

(7) A protein according to (a) or (b) below:

(a) a protein consisting of an amino acid sequence having deletion, substitution, or addition of 1 to 130 amino acids in the amino acid sequence set forth in SEQ ID NO: 2 or SEQ ID NO: 7 and having a phosphatidic acid phosphatase activity; and (b) a protein consisting of an amino acid sequence having an identity of 90% or more with the amino acid sequence set forth in SEQ ID NO: 2 or SEQ ID NO: 7 and having a phosphatidic acid phosphatase activity.

(8) A protein according to (a) or (b) below:

(a) a protein consisting of an amino acid sequence having deletion, substitution, or addition of one or more amino acids in the amino acid sequence set forth in SEQ ID NO: 2 or SEQ ID NO: 7 and having an activity that enhances generation of diacylglycerol (DG) and/or triglyceride (TG) from phosphatidic acid (PA) in a PAH1-deficient yeast strain; and (b) a protein consisting of an amino acid sequence having an identity of 70% or more with the amino acid sequence set forth in SEQ ID NO: 2 or SEQ ID NO: 7 and having an activity that enhances generation of DG and/or TG from PA in a PAH1-deficient yeast strain.

(9) A protein according to (a) or (b) below:

(a) a protein consisting of an amino acid sequence having deletion, substitution, or addition of 1 to 130 amino acids in the amino acid sequence set forth in SEQ ID NO: 2 or SEQ ID NO: 7 and having an activity that enhances generation of diacylglycerol (DG) and/or triglyceride (TG) from phosphatidic acid (PA) in a PAH1-deficient yeast strain; and (b) a protein consisting of an amino acid sequence having an identity of 90% or more with the amino acid sequence set forth in SEQ ID NO: 2 or SEQ ID NO: 7 and having an activity that enhances generation of DG and/or TG from PA in a PAH1-deficient yeast strain.

(10) A protein consisting of the amino acid sequence set forth in SEQ ID NO: 2 or SEQ ID NO: 7.

(11) A recombinant vector comprising a nucleic acid according to any one of aspects (1) to (5).

(12) A transformant transformed with the recombinant vector according to aspect (11).

(13) A fatty acid composition comprising a fatty acid or a lipid obtained by culturing the transformant according to aspect (12).

(14) A method for producing a fatty acid composition, chyaracterized by collecting a fatty acid or a lipid from a culture obtained by culturing the transformant according to aspect (12).

(15) A food comprising the fatty acid composition according to aspect (13).

Advantageous Effects of Invention

The PAP of the present invention can enhance the ability of producing fatty acids and reserve lipids in cells to which PAP has been introduced, and preferably can enhance the productivity of polyunsaturated fatty acids in microorganisms or plants.

The PAP of the present invention is expected to produce fatty acids in a host cell, the fatty acids having a composition different from that of fatty acids produced in a host cell to which PAP is not introduced. This can provide lipids having intended characteristics and effects and is therefore useful in application to, for example, foods, cosmetics, pharmaceuticals, and soap.

BRIEF DESCRIPTION OF DRAWINGS

FIG. 1-1 shows a comparison between a genomic sequence (SEQ ID NO: 5) and an ORF (SEQ ID NO: 1) of a MaPAH1.1 derived from *M. alpina* strain 1S-4.

FIG. 1-2 is the continuation of FIG. 1-1.

FIG. 1-3 is the continuation of FIG. 1-2.

FIG. 1-4 is the continuation of FIG. 1-3.

FIG. 2-1 shows a comparison between genomic sequence (SEQ ID NO: 10) and an ORF (SEQ ID NO: 6) of a MaPAH1.2 derived from *M. alpina* strain 1S-4.

FIG. 2-2 is a continuation of FIG. 2-1.

FIG. 2-3 is a continuation of FIG. 2-2.

FIG. 2-4 is a continuation of FIG. 2-3.

FIG. 3-1 shows the cDNA (SEQ ID NO: 4) of MaPAH1.1 derived from *M. alpina* strain 1S-4 and an amino acid sequence (SEQ ID NO: 2) deduced therefrom.

FIG. 3-2 is a continuation of FIG. 3-1.

FIG. 3-3 is a continuation of FIG. 3-2.

FIG. 4-1 shows the cDNA (SEQ ID NO: 9) of MaPAH1.2 derived from *M. alpina* strain 1S-4 and an amino acid sequence (SEQ ID NO: 7) deduced therefrom.

FIG. 4-2 is a continuation of FIG. 4-1.

FIG. 5-1 shows a comparison of a deduced amino acid sequence (SEQ ID NO: 2) of MaPAH1.1 and a deduced amino acid sequence (SEQ ID NO: 7) of MaPAH1.2 derived from *M. alpina* strain 1S-4 with phosphatidic acid phosphatases of a PAP1 family, a ScPAH1 protein (SEQ ID NO: 19) derived from yeast, *Saccharomyces cerevisiae*, and lipin amino acid sequence (SEQ ID NO: 20) derived from a mouse. In phosphatidic acid phosphatases of a PAP1 family, the N-terminal region is well conserved and is referred to as lipin, N-terminal conserved region (pfam04571). Also in MaPAH1.1 and MaPAH1.2, the N-terminal region is well conserved. In this sequence, the glycine residue indicated by * (corresponding to the 80th amino acid of SEQ ID NO: 2 and the 80th amino acid of SEQ ID NO: 7) is known to be essential for PAP activity. The sequence indicated by a double underline (corresponding to the 819th to 823rd amino acids of SEQ ID NO: 2 and 737th to 741st amino acids of SEQ ID NO: 7) is a DXDX(T/V) motif present in a haloacid dehalogenase (HAD)-like domain. This motif is also conserved in MaPAH1.1 and MaPAH1.2. The sequences upstream and downstream of the motif are also conserved.

FIG. 5-2 is a continuation of FIG. 5-1.

FIG. 6-1 shows a comparison of a CDS sequence (SEQ ID NO: 3) of MaPAH1.1 and a CDS sequence (SEQ ID NO: 8) of MaPAH1.2 derived from *M. alpina* strain 1S-4.

FIG. 6-2 is a continuation of FIG. 6-1.

FIG. 6-3 is a continuation of FIG. 6-2.

FIG. 7 shows a comparison of a deduced amino acid sequence (SEQ ID NO: 2) of MaPAH1.1 with a deduced amino acid sequence (SEQ ID NO: 7) of MaPAH1.2 derived from *M. alpina* strain 1S-4.

DESCRIPTION OF EMBODIMENTS

The present invention relates to a novel phosphatidic acid phosphatase gene derived from genus *Mortierella*, wherein the phosphatidic acid phosphatase dephosphorylates phosphatidic acid to generate diacylglycerol.

The phosphatidic acid phosphatase of the present invention is an enzyme that catalyzes a reaction of generating diacylglycerol by dephosphorylation of phosphatidic acid. The substrate of PAP of the present invention is usually phosphatidic acid, but is not limited thereto.

Nucleic Acid Encoding Phosphatidic Acid Phosphatase of the Present Invention

Phosphatidic acid phosphatase (PAP) of the present invention encompasses MaPAH1.1 and MaPAH1.2. The correspondences between cDNA, CDS, and ORF encoding MaPAH1.1 and MaPAH1.2, as well as a deduced amino acid sequence are summarized in Table 1.

TABLE 1

| | MaPAH1.1 | | MaPAH1.2 | |
|---|---|---|---|---|
| | SEQ ID NO | Corresponding region in SEQ ID NO: 4 | SEQ ID NO | Corresponding region in SEQ ID NO: 9 |
| cDNA | SEQ ID NO: 4 | ***** | SEQ ID NO: 9 | ***** |
| CDS | SEQ ID NO: 3 | Positions 1 to 3985 | SEQ ID NO: 8 | Positions 72 to 3791 |
| ORF | SEQ ID NO: 1 | Positions 1 to 3982 | SEQ ID NO: 6 | Positions 72 to 3788 |
| Amino acid sequence | SEQ ID NO: 2 | ***** | SEQ ID NO: 7 | ***** |

Sequences related to MaPAH1.1 of the present invention include SEQ ID NO: 2, which is the amino acid sequence of MaPAH1.1; SEQ ID NO: 1, which shows the sequence of the ORF region of MaPAH1.1; SEQ ID NO: 3, which shows the sequence of the CDS region of MaPAH1.1; and SEQ ID NO: 4, which is the nucleotide sequence of cDNA for MaPAH1.1. Among them, SEQ ID NO: 3 corresponds to the nucleotides 1 to 3985 of SEQ ID NO: 4, while SEQ ID NO: 1 corresponds to the nucleotides 1 to 3982 of SEQ ID NO: 4 and the nucleotides 1 to 3982 of SEQ ID NO: 3. SEQ ID NO: 5 is a genomic nucleotide sequence encoding MaPAH1.1 of the present invention. The genomic sequence of SEQ ID NO: 5 is composed of eleven exons and ten introns. In SEQ ID NO: 5, the exon regions correspond to the nucleotides 1 to 182, 370 to 584, 690 to 1435, 1536 to 1856, 1946 to 2192, 2292 to 2403, 2490 to 2763, 2847 to 3077, 3166 to 3555, 3648 to 3862, and 3981 to 5034.

Sequences related to MaPAH1.2 of the present invention include SEQ ID NO: 7, which is the amino acid sequence of MaPAH1.2; SEQ ID NO: 6, which shows the sequence of the ORF region of MaPAH1.2; SEQ ID NO: 8, which shows the sequence of the CDS region of MaPAH1.2; and SEQ ID NO: 9, which is the nucleotide sequence of cDNA for MaPAH1.2. Among them, SEQ ID NO: 8 corresponds to the nucleotides 72-3791 of SEQ ID NO: 9, while SEQ ID NO: 6 corresponds to the nucleotides 72 to 3788 of SEQ ID NO: 9 and the nucleotides 1 to 3717 of SEQ ID NO: 8. SEQ ID NO: 10 is a genomic nucleotide sequence encoding MaPAH1.2 of the present invention. The genomic sequence of SEQ ID NO: 10 consists of eight exons and seven introns. In SEQ ID NO: 10, the exon regions correspond to the nucleotides 1 to 454, 674 to 1006, 1145 to 1390, 1479 to 1583, 1662 to 1804, 1905 to 2143, 2243 to 3409, and 3520 to 4552.

The nucleic acids of the present invention encompass single-stranded and double-stranded DNAs and also complementary RNAs thereof, which may be either naturally occurring or artificially prepared. Examples of DNA include, but not limited to, genomic DNAs, cDNAs corresponding to the genomic DNAs, chemically synthesized DNAs, PCR-amplified DNAs, combinations thereof, and DNA/RNA hybrids.

Preferred embodiments for the nucleic acids of the present invention include (a) nucleic acids comprising the nucleotide sequence set forth in SEQ ID NO: 1 or SEQ ID NO: 6, (b) nucleic acids comprising a nucleotide sequence encoding a protein consisting of the amino acid sequence set forth in SEQ ID NO: 2 or SEQ ID NO: 7, (c) nucleic acids comprising the nucleotide sequence set forth in SEQ ID NO: 4 or SEQ ID NO: 9, and (d) nucleic acids comprising the nucleotide sequence set forth in SEQ ID NO: 5 or SEQ ID NO: 10.

In order to obtain these nucleotide sequences, nucleotide sequence data of ESTs or genomic DNAs from organisms having PAP activity may be used to search a nucleotide sequence encoding a protein having a high identity with known proteins having PAP activity. Preferred organisms having PAP activity are lipid-producing fungi including, but not limited to, M. alpina.

For EST analysis, a cDNA library is first prepared. The cDNA library may be prepared by referring to "Molecular Cloning, A Laboratory Manual 3rd ed." (Cold Spring Harbor Press (2001)). Alternatively, a commercially available cDNA library preparation kit may be used. Examples of a method of preparing a cDNA library suitable for the present invention are as follows. That is, an appropriate strain of M. alpina, a lipid-producing fungus, is inoculated into an appropriate medium and pre-cultured for an appropriate period. Culture conditions suitable for this pre-culture are, for example, a medium composition of 1.8% glucose, 1% yeast extract, and pH 6.0, a culture period of 3 to 4 days, and a culture temperature of 28° C. The pre-cultured product is then subjected to main culture under appropriate conditions. A medium composition suitable for the main culture is, for example, 1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, and 0.05% $MgCl_2.6H_2O$, and pH 6.0. Culture conditions suitable for the main culture are, for example, aeration and agitation culture at 300 rpm, 1 vvm, and 26° C. for 8 days. An appropriate amount of glucose may be added during culture. The cultured product is sampled at appropriate time points during the main culture, from which the cells are collected to prepare total RNA. The total RNA may be prepared by any known method such as a guanidine hydrochloride/CsCl method. From the resulting total RNA, poly(A)$^+$ RNA can be purified using a commercially available kit, and a cDNA library can be prepared using a commercially available kit. The nucleotide sequence of any clone from the prepared cDNA library is determined using primers that are designed on a vector to allow determination of the nucleotide sequence of an insert. As a result, ESTs can be obtained. For example, when a ZAP-cDNA GigapackIII Gold Cloning Kit (Stratagene Inc.) is used for preparing a cDNA library, directional cloning is possible.

In analysis of genomic DNA, cells of an organism having PAP activity are cultured, and genomic DNA is prepared from the cells. The nucleotide sequence of the resulting genomic DNA is determined, and the determined nucleotide sequence is assembled. From the finally obtained supercontig sequence, a sequence encoding an amino acid sequence having a high homology to the amino acid sequence of a known protein having PAP activity is searched. From the supercontig sequence giving a hit as that encoding such an amino acid sequence, primers are prepared. PCR is performed using the cDNA library as a template, and the resulting DNA fragment is inserted into a plasmid for cloning. PCR is performed using the cloned plasmid as a template and the above-mentioned primers to prepare a probe. The cDNA library is screened using the resulting probe.

A homology search of deduced amino acid sequences of MaPAH1.1 and MaPAH1.2 of the present invention was performed against amino acid sequences registered in GenBank with BLASTp program. These deduced amino acid sequences of MaPAH1.1 and MaPAH1.2 give a hit with nuclear elongation and deformation protein 1 putative protein (AAW42851) derived from Cryptococcus neoformans var. neoformans JEC21 with the highest scores, and the identities are 25.9% and 26.6%, respectively. The deduced amino acid sequences of MaPAH1.1 and MaPAH1.2 of the present invention have identities of 22.7% and 22.5%, respectively, with the amino acid sequence of S. cerevisiae-derived PAH1 protein (throughout the specification, also referred to as PAH1 of yeast or ScPAH1), which has been functionally analyzed, among PAP1 homologs of fungi.

The present invention also encompasses nucleic acids functionally equivalent to a nucleic acid including the nucleotide sequence set forth in SEQ ID NO: 1 or SEQ ID NO: 6 (hereinafter also referred to as "the nucleotide sequence of the present invention") or a nucleotide sequence encoding a protein consisting of the amino acid sequence set forth in SEQ ID NO: 2 or SEQ ID NO: 7 (hereinafter also referred to as "the amino acid sequence of the present invention"). The term "functionally equivalent" refers to that a protein encoded by the nucleotide sequence of the present invention and a protein consisting of the amino acid sequence of the present invention have a phosphatidic acid phosphatase (PAP) activity. In addition, the term "functionally equivalent" includes the activity that enhances generation of diacylglycerol (DG) and/or triglyceride (TG) from phosphatidic acid (PA) in a PAH1-deficient yeast strain when a protein encoded by the nucleotide sequence of the present invention or a protein consisting of the amino acid sequence of the present invention is expressed. The PAP activity of the protein of the present invention and the activity that enhances generation of DG and/or TG from PA in a PAH1-deficient yeast strain may be Mg$^{2+}$-dependent or Mg$^{2+}$-independent. The activity of the protein of the present invention is preferably Mg$^{2+}$-dependent.

Such nucleic acids that are functionally equivalent to the nucleic acids of the present invention include nucleic acids comprising nucleotide sequences shown in any one of (a) to (g) below. It should be noted that in the descriptions of the nucleotide sequences listed below, the term "the activity of the present invention" refers to "the PAP activity and/or the activity that enhances generation of DG and/or TG from PA in a PAH1-deficient yeast strain".

(a) A nucleic acid comprising a nucleotide sequence encoding a protein that consists of an amino acid sequence having deletion, substitution, or addition of one or more amino acids in the amino acid sequence set forth in SEQ ID NO: 2 or SEQ ID NO: 7 and has the activity of the present invention The nucleotide sequence contained in the nucleic acid of the present invention encompasses nucleotide sequences encoding a protein that consists of an amino acid sequence having deletion, substitution, or addition of one or more amino acids in the amino acid sequence set forth in SEQ ID NO: 2 or SEQ ID NO: 7 and has the activity of the present invention.

Specifically, the nucleotide sequence contained in the nucleic acid of the present invention is a nucleotide sequence encoding a protein having the above-described activity of the present invention and consisting of:

(i) an amino acid sequence having deletion of one or more (preferably one to several (e.g., 1 to 400, 1 to 200, 1 to 130, 1 to 100, 1 to 75, 1 to 50, 1 to 30, 1 to 25, 1 to 20, or 1 to 15, more preferably 10, 9, 8, 7, 6, 5, 4, 3, 2, or 1)) amino acids in the amino acid sequence set forth in SEQ ID NO: 2 or SEQ ID NO: 7;

(ii) an amino acid sequence having substitution of one or more (preferably one to several (e.g., 1 to 400, 1 to 200, 1 to 130, 1 to 100, 1 to 75, 1 to 50, 1 to 30, 1 to 25, 1 to 20, or 1 to 15, more preferably 10, 9, 8, 7, 6, 5, 4, 3, 2, or 1)) amino acids in the amino acid sequence set forth in SEQ ID NO: 2 or SEQ ID NO: 7;

(iii) an amino acid sequence having addition of one or more (preferably one to several (e.g., 1 to 400, 1 to 200, 1 to 130, 1 to 100, 1 to 75, 1 to 50, 1 to 30, 1 to 25, 1 to 20, or 1 to 15, more preferably 10, 9, 8, 7, 6, 5, 4, 3, 2, or 1)) amino acids in the amino acid sequence set forth in SEQ ID NO: 2 or SEQ ID NO: 7; or (iv) an amino acid sequence in any combination of (i) to (iii) above.

Among the above, substitution is preferably conservative, which means replacement of a certain amino acid residue by another residue having similar physical and chemical characteristics. It may be any substitution that does not substantially alter the structural characteristics of the original sequence. For example, any substitution is possible as long as the substituted amino acids do not disrupt the helix of the original sequence or do not disrupt any other type of secondary structure characterizing the original sequence.

Conservative substitution is generally introduced by synthesis with a biological system or chemical peptide synthesis, preferably by chemical peptide synthesis. In such a case, substituents may include an unnatural amino acid residue, a peptidomimetic, or a reversed or inverted form where an unsubstituted region is reversed or inverted in the amino acid sequence.

Unlimited examples of the mutually substitutable amino acid residues are classified and listed below:

Group A: leucine, isoleucine, norleucine, valine, norvaline, alanine, 2-aminobutanoic acid, methionine, O-methylserine, t-butylglycine, t-butylalanine, and cyclohexylalanine;

Group B: aspartic acid, glutamic acid, isoaspartic acid, isoglutamic acid, 2-aminoadipic acid, and 2-aminosuberic acid;

Group C: asparagine and glutamine;

Group D: lysine, arginine, ornithine, 2,4-diaminobutanoic acid, and 2,3-diaminopropionic acid;

Group E: proline, 3-hydroxyproline, and 4-hydroxyproline;

Group F: serine, threonine, and homoserine; and

Group G: phenylalanine and tyrosine.

In non-conservative substitution, replacement of a member of one of the above classes by a member from another class is possible. In such a case, in order to maintain the biological function of the protein of the present invention, the hydropathic indices of amino acids (hydropathic amino acid indices) (Kyte, et al., J. Mol. Biol., 157: 105-131 (1982)) are preferably considered.

In the case of non-conservative substitution, amino acid substitutions can be accomplished on the basis of hydrophilicity.

Note that in either conservative substitution or non-conservative substitution, the amino acid residue corresponding to the 80th amino acid in SEQ ID NO: 2 or SEQ ID NO: 7 is preferably glycine, and the region corresponding to the 819 to 823 amino acids of SEQ ID NO: 2 or the 737 to 741 amino acids of SEQ ID NO: 7 is preferably DXDX (T/V) (X is an arbitrary amino acid).

Throughout the specification and drawings, nucleotides, amino acids, and abbreviations thereof are those according to the IUPAC-IUB Commission on Biochemical Nomenclature or those conventionally used in the art, for example, as described in Immunology—A Synthesis (second edition, edited by E. S. Golub and D. R. Gren, Sinauer Associates, Sunderland, Mass. (1991)). Moreover, amino acids which may have optical isomers are intended to represent their L-isomers, unless otherwise specified.

Stereoisomers such as D-amino acids of the above-mentioned amino acids, unnatural amino acids such as α,α-disubstituted amino acids, N-alkylamino acids, lactic acid, and other unconventional amino acids can also be members constituting the proteins of the present invention.

Note that in the protein notation used throughout the specification, the left-hand direction is the amino terminal direction and the right-hand direction is the carboxy terminal direction, in accordance with standard usage and convention in the art.

Similarly, in general, unless otherwise specified, the left-hand end of single-stranded polynucleotide sequences is the 5'-end and the left-hand direction of double-stranded polynucleotide sequences is referred to as the 5'-direction.

Those skilled in the art would be able to design and prepare appropriate mutants of the proteins described in the specification by using techniques known in the art. For example, a region in the protein molecule suitable for changing the structure without impairing the biological activity of the protein of the present invention can be identified by targeting a region which appears to be less important for the biological activity of the protein. It is also possible to identify residues or regions conserved between similar proteins. Moreover, it is also possible to introduce conservative amino acid substitution into a region that appears to be important for the biological activity or structure of the protein of the present invention, without impairing the biological activity and without adversely affecting the polypeptide structure of the protein.

In particular, in the amino acid sequences of MaPAH1.1 and MaPAH1.2, an amino acid sequence of about 100 amino acids at the N-terminal region, which is referred to as lipin, N-terminal conserved region: pfam04571) in regard of a $Mg^{2+}$-dependent phosphatidic acid phosphatase (PAP1) family enzyme, is relatively well conserved. Moreover, the amino acid sequences of MaPAH1.1 and MaPAH1.2 each have a "DXDX(T/V) catalytic site motif", which is a conserved motif of a haloacid dehalogenase (HAD)-like protein superfamily enzyme. In FIG. 5, DIDGT sequences (corresponding to the 819 to 823 residues of SEQ ID NO: 2 and the 737 to 741 residues of SEQ ID NO: 7) indicated with double underlines correspond to these motifs. The mutants of the present invention may be any mutant that conserves the conserved motif and maintains the above-described activity. It has been reported that a variation in this conserved motif site in the PAP1 of yeast loses the PAP activity (J. Biol. Chem., 282 (51): 37026-37035, (2007)).

Those skilled in the art would be able to conduct a so-called structure-function study which identifies residues of a peptide that is important for a biological activity or structure of a protein of the present invention and residues of a peptide similar to the protein, compares the amino acid residues between these two peptides, and thereby predicts which residue in the protein similar to the protein of the present invention is the amino acid residue corresponding to the important amino acid residue for the biological activity or structure. Moreover, it is possible to select a mutant which maintains the biological activity of the protein of the present invention by selecting amino acid substituent chemically similar to the predicted amino acid residue. Likewise, those skilled in the art would also be able to analyze the three-dimensional structure and amino acid sequence of this protein mutant. The analysis results thus obtained can further be used to predict the alignment of amino acid residues involved in the three-dimensional structure of the protein. Though amino acid residues predicted to be on the protein surface may be involved in important interaction with other molecules, those skilled in the art would be able to prepare a mutant which causes no change in these amino acid residues predicted to be on the protein surface, on the basis of analysis results as mentioned above. Moreover, those skilled in the art would also be able to prepare a mutant having a single amino acid substitution for any of the amino acid residues constituting the protein of the present invention. These mutants may be screened by any known assay to collect information about the individual mutants, which in turn allows evaluation of the usefulness of individual amino acid residues constituting the protein of the present invention by comparison of the case where a mutant having substitution of a specific amino acid residue shows a lower biological activity than that of the protein of the present invention, the case where such a mutant shows no biological activity, or where such a mutant produces unsuitable activity that inhibits the biological activity of the protein of the present invention. Moreover, those skilled in the art can readily analyze amino acid substitutions undesirable for mutants of the protein of the present invention based on information collected from such routine experiment alone or in combination with other mutations.

As described above, a protein consisting of an amino acid sequence having deletion, substitution, or addition of one or more amino acids in the amino acid sequence set forth in SEQ ID NO: 2 or SEQ ID NO: 7 can be prepared according to techniques such as site-directed mutagenesis as described in, for example, "Molecular Cloning, A Laboratory Manual 3rd ed." (Cold Spring Harbor Press (2001)); "Current Protocols in Molecular Biology" (John Wiley & Sons (1987-1997); Kunkel, (1985), Proc. Natl. Acad. Sci. USA, 82: 488-92; or Kunkel, (1988), Method Enzymol., 85: 2763-6. Preparation of a mutant with such a mutation including amino acid deletion, substitution, or addition may be accomplished, for example, by known procedures such as a Kunkel method or a Gapped duplex method using a mutation-introducing kit based on site-directed mutagenesis such as a QuikChange™ Site-Directed Mutagenesis Kit (manufactured by Stratagene), a GeneTailor™ Site-Directed Mutagenesis System (manufactured by Invitrogen), or a TaKaRa Site-Directed Mutagenesis System (e.g., Mutan-K, Mutan-Super Express Km; manufactured by Takara Bio Inc.).

Techniques for allowing deletion, substitution, or addition of one or more amino acids in the amino acid sequence of a protein while maintaining its activity include, in addition to site-directed mutagenesis mentioned above, a method of treating a gene with a mutagen and a method selectively cleaving a gene and deleting, substituting or adding a selected nucleotide, and then ligating the gene.

The nucleotide sequence contained in the nucleic acid of the present invention is preferably a nucleotide sequence that encodes a protein consisting of an amino acid sequence having deletion, substitution, or addition of 1 to 130 amino acids in the amino acid sequence set forth in SEQ ID NO: 2 or SEQ ID NO: 7 and having PAP activity.

The nucleotide sequence contained in the nucleic acid of the present invention preferably encompasses nucleotide sequences that encode a protein consisting of an amino acid sequence having deletion, substitution, or addition of 1 to 130 amino acids in the amino acid sequence set forth in SEQ ID NO: 2 or SEQ ID NO: 7 and having the activity of the present invention.

The number and sites of amino acid mutations or modifications in the protein of the present invention are not limited as long as the PAP activity or the activity that enhances generation of DG and/or TG from PA in a PAH1-deficient yeast strain is maintained.

The PAP activity or the activity that enhances generation of DG and/or TG from PA in a PAH1-deficient yeast strain can be measured by a known method, for example, see J. Biol. Chem., 273, 14331-14338 (1998).

For example, the "PAP activity" of the present invention may be measured as follows: A crude enzyme solution is prepared by disrupting transformed cells expressing PAP of the present invention, centrifugating the lysate, and collecting the supernatant. The resulting crude enzyme solution may be further subjected to purification of PAP of the present invention. The crude enzyme solution containing PAP of the present invention or purified PAP of the present invention is added to a reaction solution containing 0.5 mM phosphatidic acid, 10 mM 2-mercaptoethanol, and 50 mM Tris-HCl (pH 7.5), followed by reaction at 25° C. to 28° C. for an appropriate time. The reaction is terminated by addition of a mixture of chloroform and methanol, and lipids are extracted. The resulting lipids are fractionated by thin layer chromatography to measure the amount of generated diacylglycerol.

The "activity that enhances generation of DG and/or TG from PA in a PAH1-deficient yeast strain" may be measured by, for example, as follows: A PAH1-deficient yeast strain is prepared by disrupting the ScPAH1 gene of yeast (*S. cerevisiae*). The PAH1-deficient yeast strain as a host cell is transformed using a vector containing a nucleic acid encoding PAP of the present invention, and the transformed strain is cultured. The culture solution is centrifugated to collect the cells. The cells are washed with water and lyophilized. Chloroform and methanol are added to the dried cells, and the cells are disrupted with glass beads to extract lipids. The extracted lipids are fractionated by thin layer chromatography, and the amount of generated DG and/or TG is measured. The PAH1-deficient yeast strain transformed with a vector not containing the nucleic acid encoding PAP of the present invention is used as a control for comparison. If the amount of generated DG and/or TG is increased in a PAH1-deficient yeast strain transformed with a vector containing a nucleic acid encoding PAP of the present invention, the PAP is determined to have "an activity that enhances generation of DG and/or TG from PA in a PAH1-deficient yeast strain".

(b) A nucleic acid comprising a nucleotide sequence that is hybridizable with a nucleic acid consisting of a nucleotide sequence complementary to the nucleotide sequence set forth in SEQ ID NO: 1 or SEQ ID NO: 6 under stringent conditions and encodes a protein having the activity of the present invention The nucleotide sequence contained in the nucleic acid of the present invention encompasses nucleotide sequences that are hybridizable with a nucleic acid consisting of a nucleotide sequence complementary to the nucleotide sequence set forth in SEQ ID NO: 1 or SEQ ID NO: 6 under stringent conditions and encode a protein having the activity of the present invention.

Such a nucleotide sequence can be prepared from, for example, a cDNA library or a genomic library by a known hybridization technique such as colony hybridization, plaque hybridization, or Southern blotting using a probe produced from an appropriate fragment by a method known to those skilled in the art.

Detailed procedure of the hybridization can be referred to "Molecular Cloning, A Laboratory Manual 3rd ed." (Cold Spring Harbor Press (2001), in particular, Sections 6 and 7), "Current Protocols in Molecular Biology" (John Wiley & Sons (1987-1997), in particular, Sections 6.3 and 6.4), and "DNA Cloning 1: Core Techniques, A Practical Approach 2nd ed." (Oxford University (1995), in particular, Section 2.10 for hybridization conditions).

The strength of hybridization conditions is determined primarily based on hybridization conditions, more preferably based on hybridization conditions and washing conditions. The term "stringent conditions" used throughout the specification is intended to include moderately or highly stringent conditions.

Specifically, examples of the moderately stringent conditions include hybridization conditions of 1×SSC to 6×SSC at 42° C. to 55° C., more preferably 1×SSC to 3×SSC at 45° C. to 50° C., and most preferably 2×SSC at 50° C. In the case of a hybridization solution containing, for example, about 50% formamide, a hybridization temperature of lower than the temperature mentioned above by 5° C. to 15° C. is employed. Washing conditions are, for example, 0.5×SSC to 6×SSC at 40° C. to 60° C. To the hybridization solution and washing solution, 0.05% to 0.2% SDS, preferably about 0.1% SDS, may usually be added.

Highly stringent (high stringent) conditions include hybridization and/or washing at higher temperature and/or lower salt concentration, compared to the moderately stringent conditions. Examples of the hybridization conditions include 0.1×SSC to 2×SSC at 55° C. to 65° C., more preferably 0.1×SSC to 1×SSC at 60° C. to 65° C., and most preferably 0.2×SSC at 63° C. Washing conditions are, for example, 0.2×SSC to 2×SSC at 50° C. to 68° C., and more preferably 0.2×SSC at 60° C. to 65° C.

Examples of the hybridization conditions particularly used in the present invention include, but not limited to, prehybridization in 5×SSC, 1% SDS, 50 mM Tris-HCl (pH 7.5) and 50% formamide at 42° C., overnight incubation at 42° C. in the presence of a probe to form hybrids, and washing in 0.2×SSC, 0.1% SDS at 65° C. for 20 minutes three times.

It is also possible to use a commercially available hybridization kit not using radioactive substance as a probe. Specifically, for example, a DIG nucleic acid detection kit (Roche Diagnostics) or an ECL direct labeling & detection system (manufactured by Amersham) is used for hybridization.

Preferred examples of the nucleotide sequence falling within the present invention include nucleotide sequences that are hybridizable with a nucleic acid consisting of a nucleotide sequence complementary to the nucleotide sequence set forth in SEQ ID NO: 1 or SEQ ID NO: 6 under conditions of 2×SSC at 50° C. and encode a protein having PAP activity.

(c) A nucleic acid comprising a nucleotide sequence which consists of a nucleotide sequence having an identity of 70% or more with the nucleotide sequence set forth in SEQ ID NO: 1 or SEQ ID NO: 6 and encodes a protein having the activity of the present invention The nucleotide sequence contained in the nucleic acid of the present invention encompasses nucleotide sequences which consists of a nucleotide sequence having an identity of at least 70% with the nucleotide sequence set forth in SEQ ID NO: 1 or SEQ ID NO: 6 and encode a protein having the activity of the present invention.

Preferably, for example, a nucleic acid comprises a nucleotide sequence having an identity of at least 75%, more preferably 80% or more (e.g., 85% or more, more preferably 90% or more, and most preferably 95%, 98%, or 99% or more) with the nucleotide sequence set forth in SEQ ID NO: 1 or SEQ ID NO: 6 and encoding a protein having the activity of the present invention.

The percent identity between two nucleotide sequences can be determined by visual inspection and mathematical calculation, but is preferably determined by comparing sequence information of two nucleic acids using a computer program. As computer programs for sequence comparison, for example, the BLASTN program (Altschul et al., (1990), J. Mol. Biol., 215: 403-10) version 2.2.7, available via the National Library of Medicine website: www.ncbi.nlm.nih.gov/blast/bl2seq/bls.html or the WU-BLAST 2.0 algorithm can be used. Standard default parameter settings for WU-BLAST 2.0 are described at the following Internet site: blast.wustl.edu.

(d) A nucleic acid comprising a nucleotide sequence encoding an amino acid sequence having an identity of 70% or more with the amino acid sequence set forth in SEQ ID NO: 2 or SEQ ID NO: 7 and encoding a protein having the activity of the present invention The nucleotide sequence contained in the nucleic acid of the present invention encompasses nucleotide sequences encoding an amino acid sequence having an identity of 70% or more with the amino acid sequence set forth in SEQ ID NO: 2 or SEQ ID NO: 7 and encoding a protein having the activity of the present invention. The protein encoded by the nucleic acid of the present invention may be a protein having an identity with the amino acid sequence of MaPAH1.1 or MaPAH1.2 as long as the protein is functionally equivalent to the protein having the activity of the present invention.

Specific examples of the protein include amino acid sequences having an identity of 75% or more, preferably 80% or more, more preferably 85% or more, and most preferably 90% or more (e.g., 95% or more, furthermore 98% or more) with the amino acid sequence set forth in SEQ ID NO: 2 or SEQ ID NO: 7.

The nucleotide sequence contained in the nucleic acid of the present invention is preferably a nucleotide sequence encoding an amino acid sequence having an identity of 90% or more with the amino acid sequence set forth in SEQ ID NO: 2 or SEQ ID NO: 7 and encoding a protein having the activity of the present invention. More preferably, a nucleotide sequence encoding an amino acid sequence having an identity of 95% or more with the amino acid sequence set forth in SEQ ID NO: 2 or SEQ ID NO: 7 and encoding a protein having the activity of the present invention.

The percent identity between two amino acid sequences can be determined by visual inspection and mathematical calculation or can be determined using a computer program. Examples of such a computer program include BLAST, FASTA (Altschul et al., J. Mol. Biol., 215: 403-410, (1990)) and ClustalW. In particular, various conditions (parameters) for an identity search with the BLAST program are described by Altschul et al. (Nucl. Acids. Res., 25, pp. 3389-3402, 1997) and publicly available via the website of the National Center for Biotechnology Information (NCBI) of USA or the DNA Data Bank of Japan (DDBJ) (BLAST Manual, Altschul et al., NCB/NLM/NIH Bethesda, Md. 20894; Altschul et al.). It is also possible to use a program such as genetic information processing software GENETYX Ver. 7 (Genetyx Corporation), DINASIS Pro (Hitachisoft), or Vector NTI (Infomax) for determination of the percent identity.

A specific alignment scheme for aligning a plurality of amino acid sequences can show matching of sequences also in a specific short region and can therefore detect a region having a very high sequence identity in such a short region even if the full-length sequences have no significant relationship therebetween. In addition, the BLAST algorithm can use the BLOSUM62 amino acid scoring matrix, and the following separation parameters can be used: (A) inclusion of filters to mask a segment of a query sequence having low compositional complexity (as determined by the SEG program of Wootton and Federhen (Computers and Chemistry, 1993); also see Wootton and Federhen, 1996, "Analysis of compositionally biased regions in sequence databases", Methods Enzymol., 266: 554-71) or to mask segments consisting of short-periodicity internal repeats (as determined by the XNU program of Claverie and States (Computers and Chemistry, 1993), and (B) a statistical significance threshold for reporting matches against database sequences, or the expected probability of matches being found merely by chance, according to the statistical model of E-score (Karlin and Altschul, 1990); if the statistical significance ascribed to a match is greater than this E-score threshold, the match will not be reported.

(e) A nucleic acid comprising a nucleotide sequence that is hybridizable with a nucleic acid consisting of a nucleotide sequence complementary to a nucleotide sequence encoding a protein consisting of the amino acid sequence set forth in SEQ ID NO: 2 or SEQ ID NO: 7 under stringent conditions and encodes a protein having the activity of the present invention The nucleotide sequence contained in the nucleic acid of the present invention encompasses nucleotide sequences that are hybridizable with a nucleic acid consisting of a nucleotide sequence complementary to a nucleotide sequence encoding a protein consisting of the amino acid sequence set forth in SEQ ID NO: 2 or SEQ ID NO: 7 under stringent conditions and encode a protein having the activity of the present invention.

The protein consisting of the amino acid sequence set forth in SEQ ID NO: 2 or SEQ ID NO: 7 and the hybridization conditions are as described above. Examples of the nucleotide sequence contained in the nucleic acid of the present invention include nucleotide sequences that are hybridizable with a nucleic acid consisting of a nucleotide sequence complementary to a nucleotide sequence encoding a protein consisting of the amino acid sequence set forth in SEQ ID NO: 2 or SEQ ID NO: 7 under stringent conditions and encode a protein having the activity of the present invention.

(f) A nucleic acid comprising a nucleotide sequence that is hybridizable with a nucleic acid consisting of a nucleotide sequence complementary to the nucleotide sequence set forth in SEQ ID NO: 5 or SEQ ID NO: 10 under stringent conditions and includes an exon encoding a protein having the activity of the present invention The nucleotide sequences set forth in SEQ ID NO: 5 and SEQ ID NO: 10 are respectively the genomic DNA sequences encoding MaPAH1.1 and MaPAH1.2 of the present invention.

The nucleotide sequence contained in the nucleic acid of the present invention encompasses nucleotide sequences that are hybridizable with a nucleic acid consisting of a nucleotide sequence complementary to the nucleotide sequence set forth in SEQ ID NO: 5 or SEQ ID NO: 10 under stringent conditions and include an exon encoding a protein having the activity of the present invention.

Such a nucleotide sequence can be prepared by a method known to those skilled in the art from, for example, a genomic library by a known hybridization technique such as colony hybridization, plaque hybridization, or Southern blotting using a probe produced using an appropriate fragment. The hybridization conditions are as described above.

(g) A nucleic acid comprising a nucleotide sequence which consists of a nucleotide sequence having an identity of 70% or more with the nucleotide sequence set forth in SEQ ID NO: 5 or SEQ ID NO: 10 and includes an exon encoding a protein having the activity of the present invention The nucleotide sequence contained in the nucleic acid of the present invention encompasses nucleotide sequences which consists of a nucleotide sequence having an identity of at least 70% with the nucleotide sequence set forth in SEQ ID NO: 5 or SEQ ID NO: 10 and encode a protein having the activity of the present invention. Preferred examples of the nucleotide sequence include those having an identity of at least 75%, more preferably 80% or more (e.g., 85% or more, more preferably 90% or more, and most preferably 95%, 98%, or 99% or more) with the nucleotide sequence set forth in SEQ ID NO: 5 or SEQ ID NO: 10 and having an exon encoding a protein having the activity of the present invention. The percent identity between two nucleotide sequences can be determined as described above.

The genomic DNA sequence of SEQ ID NO: 5 is composed of eleven exons and ten introns. In SEQ ID NO: 5, the exon regions correspond to nucleotides 1 to 182, 370 to 584, 690 to 1435, 1536 to 1856, 1946 to 2192, 2292 to 2403, 2490 to 2763, 2847 to 3077, 3166 to 3555, 3648 to 3862, and 3981 to 5034. The genomic DNA sequence of SEQ ID NO: 10 is composed of eight exons and seven introns. In SEQ ID NO: 10, the exon regions correspond to nucleotides 1 to 454, 674 to 1006, 1145 to 1390, 1479 to 1583, 1662 to 1804, 1905 to 2143, 2243 to 3409, and 3520 to 4552.

In another embodiment, examples of the nucleotide sequence contained in the nucleic acid of the present invention include nucleotide sequences including intron regions having a nucleotide sequence identity of 100% with the genomic DNA sequence set forth in SEQ ID NO: 5 or SEQ ID NO: 10 and exon regions having a nucleotide sequence identity of at least 70% or more, more preferably 75% or more, and more preferably 80% or more (e.g., 85% or more, more preferably 90% or more, and most preferably 95%, 98%, or 99% or more) with the sequence set forth in SEQ ID NO: 5 or SEQ ID NO: 10, wherein the exon encodes a protein having the activity of the present invention.

In another embodiment, examples of the nucleotide sequence contained in the nucleic acid of the present invention include nucleotide sequences including exon regions having a nucleotide sequence identity of 100% with the genomic DNA sequence set forth in SEQ ID NO: 5 or SEQ ID NO: 10 and intron regions having a nucleotide sequence identity of at least 70% or more, more preferably 75% or more, and more preferably 80% or more (e.g., 85% or more, more preferably 90% or more, and most preferably 95%, 98%, or 99% or more) with the sequence set forth in SEQ ID NO: 5 or SEQ ID NO: 10, wherein the intron regions can be eliminated by splicing, and thereby the exon regions are ligated to encode a protein having the activity of the present invention.

In another embodiment, examples of the nucleotide sequence contained in the nucleic acid of the present invention include nucleotide sequences including intron regions having a nucleotide sequence identity of at least 70% or more, more preferably 75% or more, and more preferably 80% or more (e.g., 85% or more, more preferably 90% or more, and most preferably 95%, 98%, or 99% or more) with the genomic DNA sequence set forth in SEQ ID NO: 5 or SEQ ID NO: 10 and exon regions having a nucleotide sequence identity of at least 70% or more, more preferably 75% or more, and more preferably 80% or more (e.g., 85% or more, more preferably 90% or more, and most preferably 95% or more, 98% or more, or 99% or more) with the sequence set forth in SEQ ID NO: 5 or SEQ ID NO: 10, wherein the intron regions can be eliminated by splicing, and thereby the exon regions are ligated to encode a protein having the activity of the present invention.

The percent identity between two nucleotide sequences can be determined by the method described above.

The nucleic acid of the present invention encompasses nucleic acids each consisting of a nucleotide sequence having deletion, substitution, or addition of one or more nucleotides in the nucleotide sequence set forth in SEQ ID NO: 1 or SEQ ID NO: 6 and encoding a protein having the activity of the present invention. More specifically, a usable nucleic acid include any one of the following nucleotide sequences:

(i) a nucleotide sequence having deletion of one or more (preferably one to several (e.g., 1 to 1200, 1 to 1000, 1 to 750, 1 to 500, 1 to 400, 1 to 300, 1 to 250, 1 to 200, 1 to 150, 1 to 100, 1 to 50, 1 to 30, 1 to 25, 1 to 20, or 1 to 15, more preferably, 10, 9, 8, 7, 6, 5, 4, 3, 2, or 1)) nucleotides in the nucleotide sequence set forth in SEQ ID NO: 1 or SEQ ID NO: 6;

(ii) a nucleotide sequence having substitution of one or more (preferably one to several (e.g., 1 to 1200, 1 to 1000, 1 to 750, 1 to 500, 1 to 400, 1 to 300, 1 to 250, 1 to 200, 1 to 150, 1 to 100, 1 to 50, 1 to 30, 1 to 25, 1 to 20, or 1 to 15, more preferably, 10, 9, 8, 7, 6, 5, 4, 3, 2, or 1)) nucleotides in the nucleotide sequence set forth in SEQ ID NO: 1 or SEQ ID NO: 6;

(iii) a nucleotide sequence having addition of one or more (preferably one to several (e.g., 1 to 1200, 1 to 1000, 1 to 750, 1 to 500, 1 to 400, 1 to 300, 1 to 250, 1 to 200, 1 to 150, 1 to 100, 1 to 50, 1 to 30, 1 to 25, 1 to 20, or 1 to 15, more preferably, 10, 9, 8, 7, 6, 5, 4, 3, 2, or 1)) nucleotides in the nucleotide sequence set forth in SEQ ID NO: 1 or SEQ ID NO: 6; or (iv) a nucleotide sequence with any combination of (i) to (iii) above, wherein the nucleotide sequence encodes a protein having the activity of the present invention.

A preferred embodiment of the nucleic acid of the present invention also encompasses nucleic acids comprising a fragment of a nucleotide sequence shown in any one of (a) to (d) below:

(a) the nucleotide sequence set forth in SEQ ID NO: 1 or SEQ ID NO: 6;

(b) a nucleotide sequence encoding a protein consisting of the amino acid sequence set forth in SEQ ID NO: 2 or SEQ ID NO: 7;

(c) the nucleotide sequence set forth in SEQ ID NO: 4 or SEQ ID NO: 9; and (d) the nucleotide sequence set forth in SEQ ID NO: 5 or SEQ ID NO: 10.

(A) the nucleotide sequence set forth in SEQ ID NO: 1 or SEQ ID NO: 6, (b) the nucleotide sequence encoding a protein consisting of the amino acid sequence set forth in SEQ ID NO: 2 or SEQ ID NO: 7, and (c) the nucleotide sequence set forth in SEQ ID NO: 4 or SEQ ID NO: 9 are as shown in Table 1. The nucleotide sequence set forth in SEQ ID NO: 5 or SEQ ID NO: 10 is also as described above. The fragments of these sequences are ORF, CDS, a biologically active region, a region used as a primer as described later, and a region which may serve as a probe contained in these nucleotide sequences, and may be either naturally occurring or artificially prepared.

The nucleic acid of the present invention encompasses the following nucleic acids.

(1) Nucleic acids shown in any one of (a) to (g) below:

(a) nucleic acids comprising a nucleotide sequence encoding a protein consisting of an amino acid sequence having deletion, substitution, or addition of one or more amino acids in the amino acid sequence set forth in SEQ ID NO: 2 or SEQ ID NO: 7;

(b) nucleic acids hybridizable with a nucleic acid consisting of a nucleotide sequence complementary to the nucleotide sequence set forth in SEQ ID NO: 1 or SEQ ID NO: 6 under stringent conditions;

(c) nucleic acids comprising a nucleotide sequence having an identity of 70% or more with the nucleotide sequence set forth in SEQ ID NO: 1 or SEQ ID NO: 6;

(d) nucleic acids comprising a nucleotide sequence encoding a protein consisting of an amino acid sequence having an identity of 70% or more with the amino acid sequence set forth in SEQ ID NO: 2 or SEQ ID NO: 7;

(e) nucleic acids hybridizable with a nucleic acid consisting of a nucleotide sequence complementary to a nucleotide sequence encoding a protein consisting of the amino acid sequence set forth in SEQ ID NO: 2 or SEQ ID NO: 7 under stringent conditions;

(f) nucleic acids hybridizable with a nucleic acid consisting of a nucleotide sequence complementary to the nucleotide sequence set forth in SEQ ID NO: 5 or SEQ ID NO: 10 under stringent conditions; and (g) nucleic acids comprising a nucleotide sequence having an identity of 70% or more with the nucleotide sequence set forth in SEQ ID NO: 5 or SEQ ID NO: 10.

(2) Nucleic acids described in (1) above, shown in any one of (a) to (g) below:

(a) nucleic acids comprising a nucleotide sequence encoding a protein consisting of an amino acid sequence having deletion, substitution, or addition of 1 to 130 amino acids in the amino acid sequence set forth in SEQ ID NO: 2 or SEQ ID NO: 7;

(b) nucleic acids hybridizable with a nucleic acid consisting of a nucleotide sequence complementary to the nucleotide sequence set forth in SEQ ID NO: 1 or SEQ ID NO: 6 under conditions of 2×SSC at 50° C.;

(c) nucleic acids comprising a nucleotide sequence having an identity of 90% or more with the nucleotide sequence set forth in SEQ ID NO: 1 or SEQ ID NO: 6;

(d) nucleic acids comprising a nucleotide sequence encoding a protein consisting of an amino acid sequence having an identity of 90% or more with the amino acid sequence set forth in SEQ ID NO: 2 or SEQ ID NO: 7;

(e) nucleic acids hybridizable with a nucleic acid consisting of a nucleotide sequence complementary to a nucleotide sequence encoding a protein consisting of the amino acid sequence set forth in SEQ ID NO: 2 or SEQ ID NO: 7 under conditions of 2×SSC at 50° C.;

(f) nucleic acids hybridizable with a nucleic acid consisting of a nucleotide sequence complementary to the nucleotide sequence set forth in SEQ ID NO: 5 or SEQ ID NO: 10 under conditions of 2×SSC at 50° C.; and (g) nucleic acids comprising a nucleotide sequence having an identity of 90% or more with the nucleotide sequence set forth in SEQ ID NO: 5 or SEQ ID NO: 10.

Phosphatidic Acid Phosphatase of the Present Invention

The protein of the present invention encompasses a protein consisting of the amino acid sequence set forth in SEQ ID NO: 2 or SEQ ID NO: 7 and proteins functionally equivalent to such a protein. These proteins may be either naturally occurring or artificially prepared. The protein consisting of the amino acid sequence set forth in SEQ ID NO: 2 or SEQ ID NO: 7 is as described above. The "proteins functionally equivalent" refers to proteins having "the activity of the present invention" described in the "Nucleic acid encoding phosphatidic acid phosphatase of the present invention" above.

In the present invention, examples of the proteins functionally equivalent to a protein consisting of the amino acid sequence set forth in SEQ ID NO: 2 or SEQ ID NO: 7 include proteins shown in (a) and (b) below:

(a) proteins comsisting of an amino acid sequence having deletion, substitution, or addition of one or more amino acids in the amino acid sequence set forth in SEQ ID NO: 2 or SEQ ID NO: 7 and having the activity of the present invention; and (b) proteins consisting of an amino acid sequence having an identity of 70% or more with the amino acid sequence set forth in SEQ ID NO: 2 or SEQ ID NO: 7 and having the activity of the present invention.

In the above, the amino acid sequence having deletion, substitution, or addition of one or more amino acids in the amino acid sequence set forth in SEQ ID NO: 2 or SEQ ID NO: 7 or the amino acid sequence having an identity of 70% or more with the amino acid sequence set forth in SEQ ID NO: 2 are as described in the "Nucleic acid encoding phosphatidic acid phosphatase of the present invention" above. The "protein having the activity of the present invention" encompasses mutants of proteins encoded by a nucleic acid containing the nucleotide sequence set forth in SEQ ID NO: 1 or SEQ ID NO: 6; mutated proteins by many types of modification such as deletion, substitution, and addition of one or more amino acids in the amino acid sequence set forth in SEQ ID NO: 2 or SEQ ID NO: 7; those proteins modified having, for example, modified amino acid side chains; and those proteins fused with other proteins, where these proteins have the PAP activity and/or the activity that enhances generation of diacylglycerol (DG) and/or triglyceride (TG) from phosphatidic acid (PA) in a PAH1-deficient yeast strain.

The protein of the present invention may be artificially prepared. In such a case, the protein can be produced by chemical synthesis such as a Fmoc method (fluorenylmethyloxycarbonyl method) or a tBoc method (t-butyloxycarbonyl method). In addition, peptide synthesizers available from Advanced ChemTech, Perkin Elmer, Pharmacia, Protein Technology Instrument, Synthecell-Vega, PerSeptive, Shimadzu Corporation, or other manufacturers may be used for chemical synthesis.

The protein of the present invention further encompasses the following proteins:

(1) (a) proteins consisting of an amino acid sequence having deletion, substitution, or addition of one or more amino acids in the amino acid sequence set forth in SEQ ID NO: 2 or SEQ ID NO: 7;

(b) proteins consisting of an amino acid sequence having an identity of 80% or more with the amino acid sequence set forth in SEQ ID NO: 2 or SEQ ID NO: 7; and (2) proteins according to any one of (a) and (b) below:

(a) proteins consisting of an amino acid sequence having deletion, substitution, or addition of 1 to 200 amino acids in the amino acid sequence set forth in SEQ ID NO: 2 or SEQ ID NO: 7; and (b) proteins consisting of an amino acid sequence having an identity of 90% or more with the amino acid sequence set forth in SEQ ID NO: 2 or SEQ ID NO: 7.

Cloning of Nucleic Acid of the Present Invention

The PAP nucleic acid of the present invention can be cloned by, for example, screening from a cDNA library using an appropriate probe. The cloning can be performed by PCR amplification using appropriate primers and subsequent ligation to an appropriate vector. The cloned nucleic acid may be further subcloned into another vector.

Commercially available plasmid vectors can be used, such as pBlue-Script™ SK(+) (Stratagene), pGEM-T (Promega), pAmp (TM: Gibco-BRL), p-Direct (Clontech), or pCR2.1-TOPO (Invitrogen). In PCR amplification, primers may be any regions of, e.g., the nucleotide sequence set forth in SEQ ID NO: 4. For example, NotI-PAH1-1-F: 5'-GCGGCCGCATGCAGTCCGTGGGAAG-3' (SEQ ID NO: 15) can be used as an upstream primer, and MaPAH1-1-10R: 5'-TTCTTGAGTAGCTGCTGTTGTTCG-3' (SEQ ID NO: 16) can be used as a downstream primer. Then, PCR is performed using cDNA prepared from *M. alpina* cells with the primers above, DNA polymerase, and any other substance. Although this procedure can be readily performed by those skilled in the art according to, e.g., "Molecular Cloning, A Laboratory Manual 3rd ed." (Cold Spring Harbor Press (2001)), PCR conditions in the present invention may be, for example, as follows:

Denaturation temperature: 90° C. to 95° C.,
Annealing temperature: 40° C. to 60° C.,
Elongation temperature: 60° C. to 75° C., and
Number of cycles: 10 or more cycles.

The resulting PCR product can be purified by a known method, for example, using a kit such as GENECLEAN kit (Funakoshi Co., Ltd.), QIAquick PCR purification (QIAGEN), or ExoSAP-IT (GE Healthcare Bio-Sciences)); a DEAE-cellulose filter; or a dialysis tube. In the case of using an agarose gel, the PCR product is subjected to agarose gel electrophoresis, and nucleotide sequence fragments are cut out from the agarose gel and are purified, for example, with a GENECLEAN kit (Funakoshi Co., Ltd.) or a QIAquick Gel extraction kit (QIAGEN) or by a freeze-squeeze method.

The nucleotide sequence of the cloned nucleic acid can be determined with a nucleotide sequencer.

Vector Construction for Pap Expression and Preparation of Transformant

The present invention also provides a recombinant vector containing a nucleic acid encoding PAP of the present invention. The present invention further provides a transformant transformed with such a recombinant vector.

The recombinant vector and transformant can be prepared as follows: A plasmid having a nucleic acid encoding the PAP of the present invention is digested with a restriction enzyme. Examples of the restriction enzyme include, but not limited to, EcoRI, KpnI, BamHI, and SalI. The end may be blunted with T4 polymerase. A digested DNA fragment is purified by agarose gel electrophoresis. This DNA fragment is incorporated into an expression vector by a known method in order to prepare a vector for PAP expression. This expression vector is introduced into a host cell to prepare a transformant, which is provided for expression of a desired protein.

In this case, the expression vector and the host may be any types that allow expression of a desired protein. Examples of the host include fungi, bacteria, plants, animals, and cells thereof. Examples of fungi include filamentous fungi such as lipid-producing *M. alpina* and yeast strains such as *Saccharomyces cerevisiae*. Examples of bacteria include *Escherichia coli* and *Bacillus subtilis*. Further examples of plants include oil plants such as rapeseed, soybean, cotton, safflower, and flax.

As lipid-producing microorganisms, for example, strains described in MYCOTAXON, Vol. XLIV, NO. 2, pp. 257-265 (1992) can be used, and specific examples thereof include microorganisms belonging to the genus *Mortierella* such as microorganisms belonging to subgenus *Mortierella*, e.g., *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70, and CBS754.68; and microorganisms belonging to subgenus *Micromucor*, e.g., *Mortierella isabellina* CBS194.28, IFO6336, IFO7824, IFO7873, IFO7874, IFO8286, IFO8308, IFO7884, *Mortierella nana* IFO8190, *Mortierella ramanniana* IFO5426, IFO8186, CBS112.08, CBS212.72, IFO7825, IFO8184, IFO8185, IFO8287, and *Mortierella vinacea* CBS236.82. In particular, *Mortierella alpina* is preferred.

When a fungus is used as a host, the nucleic acid of the present invention is preferably self-replicable in the host or preferably has a structure insertable onto the fungal chromosome. Preferably, the nucleic acid also includes a promoter and a terminator. When *M. alpina* is used as a host, for example, pD4, pDuraSC, or pDura5 can be used as the expression vector. Any promoter that allows expression in the host can be used, and examples thereof include promoters derived from *M. alpina*, such as histonH4.1 gene promoter, GAPDH (glyceraldehyde-3-phosphate dehydrogenase) gene promoter, and TEF (translation elongation factor) gene promoter.

Examples of the method introducing a recombinant vector into filamentous fungi such as *M. alpina* include electroporation, a spheroplast method, a particle delivery method, and direct microinjection of DNA into nuclei. In the case of using an auxotrophic host strain, the transformed strain can be obtained by selecting a strain that grows on a selective medium lacking a certain nutrient(s). Alternatively, in transformation of using a drug resistant-marker gene, a colony of drug-resistant cells can be obtained by culturing the host cells in a selective medium containing the drug.

When yeast is used as a host, for example, pYE22m can be used as the expression vector. Alternatively, commercially available yeast expression vectors such as pYES (Invitrogen) or pESC(STRATAGENE) may be used. Examples of the host suitable for the present invention include, but not limited to, *Saccharomyces cerevisiae* strain EH13-15 (trp1, MATα). The promoter that can be used is, for example, a promoter derived from yeast, such as GAPDH promoter, gal1 promoter, or gal10 promoter.

Examples of the method introducing a recombinant vector into yeast include a lithium acetate method, electroporation, a spheroplast method, dextran-mediated transfection, calcium phosphate precipitation, polybrene-mediated transfection, protoplast fusion, encapsulation of polynucleotide(s) in liposomes, and direct microinjection of DNA into nuclei.

When a bacterium such as *E. coli* is used as a host, for example, pGEX or pUC18 available from Pharmacia can be used as the expression vector. The promoter that can be used include those derived from, for example, *E. coli* or phage, such as trp promoter, lac promoter, PL promoter, and PR promoter. Examples of the method of introducing a recombinant vector into bacteria include electroporation and calcium chloride methods.

Method of Preparing Fatty Acid Composition of the Present Invention

The present invention provides a method of preparing a fatty acid composition from the transformant described above, i.e., a method of preparing a fatty acid composition from a cultured product obtained by culturing the transformant. The fatty acid composition contains an assembly of one or more fatty acids therein. The fatty acids may be free fatty acids or may be present in the form of lipids containing fatty acids such as triglyceride or phospholipid. Specifically, the fatty acid composition of the present invention can be prepared by the following method. Alternatively, the fatty acid composition can also be prepared by any other known method.

The medium used for culturing an organism expressing PAP may be any culture solution (medium) that has an appropriate pH and osmotic pressure and contains biomaterials such as nutrients, trace elements, serum, and antibiotics necessary for growth of each host. For example, in the case of expressing PAP by transforming yeast, unlimited examples of the medium include SC-Trp medium, YPD medium, and YPD5 medium. The composition of a specific medium, for example, SC-Trp medium, is as follows: One liter of the medium includes 6.7 g of yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, and 0.6 g of uracil).

Any culture conditions which are suitable for host growth and adequate for stably maintaining the generated enzyme may be employed. Specifically, individual conditions including anaerobic degree, culture period, temperature, humidity, and static culture or shake culture can be adjusted. Culture may be accomplished under the same conditions (one-step culture) or by so-called two-step or three-step culture using two or more different culture conditions. For large-scale culture, two- or more-step culture is preferred because of its high culture efficiency.

In two-step culture using yeast as the host, the fatty acid composition of the present invention can be prepared as follows: As pre-culture, a colony of a transformant is inoculated in, for example, the SC-Trp medium and shake-cultured at 30° C. for two days. Subsequently, 500 µL of the pre-culture solution as main culture is added to 10 mL of YPD5 (2% yeast extract, 1% polypeptone, and 5% glucose) medium, followed by shake culture at 30° C. for two days.

Fatty Acid Composition of the Present Invention

The present invention also provides a fatty acid composition as an assembly of one or more fatty acids in cells expressing PAP of the present invention, preferably, a fatty acid composition obtained by culturing a transformant expressing PAP of the present invention. The fatty acids may be free fatty acids or may be present in the form of lipids containing fatty acids such as triglyceride or phospholipid.

The fatty acids contained in the fatty acid composition of the present invention are linear or branched monocarboxylic acids of long-chain carbohydrates, and examples thereof include, but not limited to, myristic acid (tetradecanoic acid) (14:0), myristoleic acid (tetradecenoic acid) (14:1), palmitic acid (hexadecanoic acid) (16:0), palmitoleic acid (9-hexadecenoic acid) (16:1), stearic acid (octadecanoic acid) (18:0), oleic acid (cis-9-octadecenoic acid) (18:1(9)), vaccenic acid (11-octadecenoic acid) (18:1(11)), linolic acid (cis,cis-9,12 octadecadienoic acid) (18:2(9,12)), α-linolenic acid (9,12,15-octadecatrienoic acid) (18:3(9,12,15)), γ-linolenic acid (6,9,12-octadecatrienoic acid) (18:3(6,9,12)), stearidonic acid (6,9,12,15-octadecatetraenoic acid) (18:4(6,9,12,15)), arachidic acid (icosanoic acid) (20:0), (8,11-icosadienoic acid) (20:2(8,11)), mead acid (5,8,11-icosatrienoic acid) (20:3(5,8,11)), dihomo-γ-linolenic acid (8,11,14-icosatrienoic acid) (20:3(8,11,14)), arachidonic acid (5,8,11,14-icosatetraenoic acid) (20:4(5,8,11,14)), eicosatetraenoic acid (8,11,14,17-icosatetraenoic acid) (20:4(8,11,14,17)), eicosapentaenoic acid (5,8,11,14,17-icosapentaenoic acid) (20:5(5,8,11,14,17)), behenic acid (docosanoic acid) (22:0), (7,10,13,16-docosatetraenoic acid) (22:4(7,10,13,16)), (7,10,13,16,19-docosapentaenoic acid) (22:5(7,10,13,16,19)), (4,7,10,13,16-docosapentaenoic acid) (22:5(4,7,10,13,16)), (4,7,10,13,16,19-docosahexaenoic acid) (22:6(4,7,10,13,16,19)), lignoceric acid (tetracosanoic acid) (24:0), nervonic acid (cis-15-tetradocosanoic acid) (24:1), and cerotic acid (hexacosanoic acid) (26:0). Note that the substance names are common names defined by the IUPAC Biochemical Nomenclature, and their systematic names are given in parentheses along with numerics denoting the number of carbons and the positions of double bonds.

The fatty acid composition of the present invention may be composed of any number and any type of fatty acids, as long as it is a combination of one or more fatty acids selected from the fatty acids mentioned above.

Food or Other Products Comprising Fatty Acid Composition of the Present Invention The present invention also provides a food product comprising the fatty acid composition described above. The fatty acid composition of the present invention can be used for production of food products containing fats and oils and production of industrial raw materials (for example, raw materials for cosmetics, pharmaceuticals (e.g., external applications for the skin), and soaps), in usual methods. Cosmetics (cosmetic compositions) or pharmaceuticals (pharmaceutical compositions) may be formulated into any dosage form including, but not limited to, solutions, pastes, gels, solids, and powders. Examples of the forms of food products include pharmaceutical formulations such as capsules; natural liquid diets, semi-digested nutritious diets, and elemental nutritious diets where the fatty acid composition of the present invention is blended with proteins, sugars, fats, trace elements, vitamins, emulsifiers, and flavorings; and processed forms such as drinkable preparations and enteral nutrients.

Moreover, examples of the food product of the present invention include, but not limited to, nutritional supplements, health food, functional food, children's food, modified milk for infants, modified milk for premature infant, and geriatric food. Throughout the specification, the term "food" is used as a collective term for edible materials in the form of a solid, a fluid, a liquid, or a mixture thereof.

The term "nutritional supplements" refers to food products enriched with specific nutritional ingredients. The term "health food" refers to food products that are healthful or good for health and encompasses nutritional supplements, natural food, and diet food. The term "functional food" refers to food products for supplying nutritional ingredients that assist body control functions and is synonymous with food for specified health use. The term "children's food" refers to food products given to children up to about 6 years old. The term "geriatric food" refers to food products treated to facilitate digestion and absorption thereof, compared to untreated food. The term "modified milk for infants" refers to modified milk given to children up to about one year old. The term "modified milk for premature infants" refers to modified milk given to premature infants until about 6 months after birth.

Examples of these food products include natural food (treated with fats and oils) such as meat, fish, and nuts; food supplemented with fats and oils during preparation, such as Chinese foods, Chinese noodles, and soups; food products prepared using fats and oils as heating media, such as tempura (deep-fried fish and vegetables), deep-fried food, fried tofu, Chinese fried rice, doughnuts, and Japanese fried dough cookies (karinto); fat- and oil-based food or processed food supplemented with fats and oils during processing, such as butter, margarine, mayonnaise, dressing, chocolate, instant noodles, caramel, biscuits, cookies, cake, and ice cream; and food sprayed or coated with fats and oils upon finishing, such as rice crackers, hard biscuits, and sweet bean paste bread. However, the food products of the present invention are not limited to food containing fats and oils, and other examples thereof include agricultural food products such as bakery products, noodles, cooked rice, sweets (e.g., candies, chewing gums, gummies, tablets, Japanese sweets), tofu, and processed products thereof; fermented food products such as refined sake, medicinal liquor, seasoning liquor (mirin), vinegar, soy sauce, and miso; livestock food products such as yogurt, ham, bacon, and sausage; seafood products such as fish paste (kamaboko), deep-fried fish paste (ageten), and fish cake (hanpen); and fruit drinks, soft drinks, sports drinks, alcoholic beverages, and tea.

Method for Strain Evaluation and Selection Using Pap-Encoding Nucleic Acid or PAP Protein of the Present Invention The present invention also provides a method of evaluating or selecting a lipid-producing fungus using the PAP-encoding nucleic acid or PAP protein of the present invention. Details are given below.

(1) Method for Evaluation

One embodiment of the present invention is a method of evaluating a lipid-producing fungus using the PAP-encoding nucleic acid or PAP protein of the present invention. In the method for evaluation of the present invention, for example, a lipid-producing fungus strain as a test strain is evaluated for the activity of the present invention using primers or probes designed based on the nucleotide sequence of the present invention. Such evaluation can be performed by known procedures, for example, described in International Publication No. WO01/040514 and JP-A-8-205900. The method for evaluation will be briefly described below.

The first step is preparation of a genome of a test strain. The genome can be prepared by any known method such as a Hereford method or a potassium acetate method (see, e.g., Methods in Yeast Genetics, Cold Spring Harbor Laboratory Press, p. 130 (1990)).

Primers or probes are designed based on the nucleotide sequence of the present invention, preferably the sequence set forth in SEQ ID NO: 1 or SEQ ID NO: 6. These primers or probes may be any regions of the nucleotide sequence of the present invention and may be designed by a known procedure. The number of nucleotides in a polynucleotide used as a primer is generally 10 or more, preferably 15 to 25. The number of nucleotides appropriate for a region to be flanked by primers is generally 300 to 2000.

The primers or probes prepared above are used to examine whether the genome of a test strain contains a sequence specific to the nucleotide sequence of the present invention. The sequence specific to the nucleotide sequence of the present invention can be detected by a known procedure. For example, a polynucleotide containing a part or all of the sequence specific to the nucleotide sequence of the present invention or a polynucleotide containing a nucleotide sequence complementary to the nucleotide sequence is used as one primer, and a polynucleotide containing a part or all of a sequence located upstream or downstream of this sequence or a polynucleotide containing a nucleotide sequence complementary to the nucleotide sequence is used as the other primer, and a nucleic acid from the test strain is amplified by PCR or other techniques. Further, for example, the presence or absence of an amplification product and the molecular weight of an amplification product can be measured.

PCR conditions suitable for the method of the present invention are not particularly limited and may be, for example, as follows:

Denaturation temperature: 90° C. to 95° C.
Annealing temperature: 40° C. to 60° C.
Elongation temperature: 60° C. to 75° C.
Number of cycles: 10 or more cycles.

The resulting reaction products can be separated by electrophoresis on an agarose gel or any other process to determine the molecular weight of the amplification product. The test strain can be predicted or evaluated for the activity of the present invention by confirming whether the molecular weight of the amplification product is enough for covering a nucleic acid molecule corresponding to a region specific to the nucleotide sequence of the present invention. Furthermore, the activity of the present invention can be predicted or evaluated with higher accuracy by analyzing the nucleotide sequence of the amplification product by the method described above. The method of evaluating the activity of the present invention is as described above.

Alternatively, in the evaluation according to the present invention, a test strain can be evaluated for the activity of the present invention by culturing the test strain and measuring the expression level of PAP encoded by the nucleotide sequence of the present invention, e.g., the sequence set forth in SEQ ID NO: 1 or SEQ ID NO: 6. The expression level of PAP can be measured by culturing a test strain under appropriate conditions and quantifying mRNA or protein for PAP. The mRNA or protein can be quantified by a known procedure. For example, mRNA can be quantified by Northern hybridization or quantitative RT-PCR, and protein can be quantified by Western blotting (Current Protocols in Molecular Biology, John Wiley & Sons, 1994-2003).

(2) Method for Selection

Another embodiment of the present invention is a method of selecting a lipid-producing fungus using the PAP-encoding nucleic acid or PAP protein of the present invention. In the selection according to the present invention, a strain having a desired activity can be selected by culturing a test strain, measuring the expression level of PAP encoded by the nucleotide sequence of the present invention, e.g., sequence set forth in SEQ ID NO: 1 or SEQ ID NO: 6, and selecting a strain of a desired expression level. Alternatively, a desired strain can be selected by establishing a standard strain, culturing the standard strain and a test strain separately, measuring the expression level of each strain, and comparing the expression level of the standard strain with that of the test strain. Specifically, for example, a standard strain and test strains are cultured under appropriate conditions, and the expression level of each strain is measured. A strain exhibiting a desired activity can be selected by selecting a test strain showing higher or lower expression than the standard strain does. The desired activity can be determined by, for example, measuring the expression level of PAP and the composition of fatty acids produced by PAP, as described above.

In the selection according to the present invention, a test strain having a desired activity can be selected by culturing test strains and selecting a strain having high or low activity of the present invention. A desired activity can be determined by, for example, measuring the expression level of PAP and the composition of fatty acids produced by PAP, as described above.

Examples of the test strain and the standard strain include, but not limited to, strains transformed with the vector of the present invention, strains modified to suppress expression of the nucleic acid of the present invention, mutagenized strains, and naturally mutated strains. The activity of the present invention can be measured by, for example, the method described in the "Nucleic acid encoding phosphatidic acid phosphatase of the present invention" in the specification. Examples of the mutagenesis include, but not limited to, physical methods such as irradiation with ultraviolet light or radiation; and chemical methods by treatment with a chemical such as EMS (ethylmethane sulfonate) or N-methyl-N-nitrosoguanidine (see, e.g., Yasuji Oshima ed., Biochemistry Experiments vol. 39, Experimental Protocols for Yeast Molecular Genetics, pp. 67-75, Japan Scientific Societies Press).

Examples of the strain used as the standard strain of the present invention or the test strain include, but not limited to, the lipid-producing fungus and yeast described above. Specifically, the standard strain and the test strain may be any combination of strains belonging to different genera or species, and one or more test strains may be simultaneously used.

The present invention will now be described in more detail by the following examples, which are not intended to limit the scope of the invention.

EXAMPLES

Example 1

Genomic Analysis of *M. alpina*

*M. alpina* strain 1S-4 was inoculated into 100 mL of a GY2:1 medium (2% glucose, 1% yeast extract, pH 6.0) and was shake-cultured at 28° C. for 2 days. The cells were collected by filtration and genomic DNA was prepared by using DNeasy (QIAGEN).

The nucleotide sequence of the genome DNA was determined using a Roche 454 GS FLX Standard. On this occasion, the nucleotide of a fragment library was sequenced in two runs, and the nucleotide of a mate pair library was sequenced in three runs. The resulting nucleotide sequences were assembled to obtain 300 supercontigs.

Example 2

Synthesis of cDNA and Construction of cDNA Library

*M. alpina* strain 1S-4 was inoculated into 100 mL of a medium (1.8% glucose, 1% yeast extract, pH 6.0) and was shake-cultured at 28° C. for 4 days. The cells were collected by filtration, and total RNA was prepared by a guanidine hydrochloride/CsCl method.

From the total RNA, cDNA was synthesized by reverse transcription with SuperScript II RT (Invitrogen) using a random hexamer. In addition, from the total RNA, poly(A)$^+$ RNA was purified using an Oligotex-dT30<Super>mRNA Purification Kit (Takara Bio Inc.). A cDNA library was constructed using a ZAP-cDNA GigapackIII Gold Cloning Kit (STRATAGENE).

Example 3

Search for Homolog of *S. cerevisiae*-Derived PAH1

The amino acid sequence of a gene having the PAP activity of *Saccharomyces cerevisiae*, PAH1 (YMR165C) (may be also referred to as ScPAH1 in the specification), was subjected to tblastn analysis against *M. alpina* strain 1S-4 genome nucleotide sequences. As a result, supercontigs including the sequences set forth in SEQ ID NO: 5 and SEQ ID NO: 10 gave a hit. The gene relating to SEQ ID NO: 5 was named MaPAH1.1, and the gene relating to SEQ ID NO: 10 was named MaPAH1.2.

Example 4

Cloning of MaPAH1.1 and MaPAH1.2

(1) Preparation of Probe

In order to clone cDNAs of the MaPAH1.1 gene and the MaPAH1.2 gene, nucleotide sequences set forth in SEQ ID NO: 5 and SEQ ID NO: 10 and the following primers determined based on the results of the BLAST analysis above were prepared.

```
                                              (SEQ ID NO: 11)
MaPAH1-1-3F: 5'-CGCCAATACATTGACGTTTTCAG-3'

(SEQ ID NO: 12)
MaPAH1-1-5R: 5'-AGTTCCAGTCATTGAACTCGGGTGC-3'

(SEQ ID NO: 13)
MaPAH1-2-3F: 5'-GAGCCCAGTTGACCTTTGAGGCATTC-3'

(SEQ ID NO: 14)
MaPAH1-2-5R: 5'-CACTGAGAACGAGACCGTGTTGGCG-3'
```

PCR was performed with ExTaq (Takara Bio Inc.) using the cDNA library constructed in Example 2 as a template and a combination of primer MaPAH1-1-3F and primer MaPAH1-1-5R or a combination of primer MaPAH1-2-3F and primer MaPAH1-2-5R at 94° C. for 2 min and then 30 cycles of (94° C. for 30 sec, 55° C. for 30 sec, and 72° C. for 2 min). The DNA fragment of about 0.6 kbp obtained in each combination was cloned with a TOPO-TA cloning Kit (Invitrogen), and the nucleotide sequence of the insert of the resulting plasmid was determined. The plasmid, obtained by the former combination of the primer, having a sequence corresponding to the nucleotides 2352 to 3010 of SEQ ID NO: 4 was identified as pCR-MaPAH1.1-P; and the plasmid, obtained by the latter combination of the primers, having a sequence corresponding to the nucleotides 1615 to 2201 of SEQ ID NO: 9 was identified as pCR-MaPAH1.2-P.

Subsequently, probes were produced by PCR using these plasmids as templates and the primers in the above. In the reaction, ExTaq (Takara Bio Inc., Japan) was used, except that a PCR labeling mix (Roche Diagnostics) was used instead of the attached dNTP mix for labeling DNAs to be amplified with digoxigenin (DIG) to prepare an MaPAH1.1 probe and an MaPAH1.2 probe. The cDNA library was screened with these probes.

Hybridization conditions were set as follows:

Buffer: 5×SSC, 1% SDS, 50 mM Tris-HCl (pH 7.5), 50% formamide,

Temperature: 42° C. (overnight), and

Washing conditions: in 0.2×SSC, 0.1% SDS solution (65° C.) for 20 min (three times).

A DIG nucleic acid detection kit (Roche Diagnostics) was used for detection. Plasmids were cut out by in vivo excision from phage clones obtained by screening to obtain each plasmid DNA. A plasmid having the longest insert among the plasmids obtained by screening with the MaPAH1.1 probe had a sequence of the positions 1307th and after in the sequence set forth in SEQ ID NO: 4 and was named plasmid pB-MaPAH1.1p. The results of comparison with the amino acid sequence of ScPAH1 suggest that this plasmid pB-MaPAH1.1p does not contain a region encoding the N-terminal of PAH1.1. Comparison of the genomic sequence (SEQ ID NO: 5), which was expected to have the MaPAH1.1 gene from the results of BLAST analysis, with the N-terminal sequence of the amino acid sequence of ScPAH1 suggest that ATG at the 1 to 3 positions in the sequence set forth in SEQ ID NO: 5 is the start codon. Each frame of the plasmid pB-MaPAH1.1p was translated into an amino acid sequence. The amino acid sequence was compared with the amino acid sequence of ScPAH1 protein derived from *S. cerevisiae*. The results suggest that the TGA at the 3985 to 3987 positions in the sequence set forth in SEQ ID NO: 4 is the stop codon. Accordingly, in order to clone the full-length cDNA, the following primers were designed:

```
NotI-PAH1-1-F:    5'-GCGGCCGCATGCAGTCCGTGGGAAG-3',
                                               (SEQ ID NO: 15)
and MaPAH1-1-10R:     5'-TTCTTGAGTAGCTGCTGTTGTTCG-3'.
                                               (SEQ ID NO: 16)
```

PCR was performed with ExTaq (Takara Bio Inc.) using the cDNA above as a template and a combination of primer NotI-PAH1-1-F and primer MaPAH1-1-10R at 94° C. for 2 min and then 30 cycles of (94° C. for 30 sec, 55° C. for 30 sec, and 72° C. for 2 min). The resulting DNA fragment of about 1.5 kbp was cloned with a TOPO-TA cloning Kit (Invitrogen), and the nucleotide sequence of the inserted part was determined. The plasmid that cloned the DNA fragment including the sequence of nucleotides 1 to 1500 of SEQ ID NO: 4 was identified as pCR-MaPAH1.1-Np. Subsequently, a DNA fragment of about 1.4 kbp obtained by digestion of plasmid pCR-MaPAH1.1-Np with restriction enzymes NotI and XhoI, a DNA fragment of about 3.7 kbp obtained by digestion of plasmid pB-MaPAH1.1p with restriction enzymes NotI and BamHI, and a DNA fragment of about 2.1 kb obtained by digestion of plasmid pB-MaPAH1.1p with restriction enzymes XhoI and BamHI were linked using ligation high (TOYOBO) to prepare plasmid pB-MaPAH1.1 cDNA, which probably contain the full-length cDNA of MaPAH1.1. A cDNA sequence including the full-length ORF of MaPAH1.1 is shown in SEQ ID NO: 4.

Separately, a plasmid having the longest insert among the plasmids obtained by screening with the MaPAH1.2 probe had the nucleotide sequence set forth in SEQ ID NO: 9. The results of comparison of this plasmid with the sequence of ScPAH1 derived from *S. cerevisiae* suggest that the plasmid has cDNA including the full-length ORF of MaPAH1.2. This plasmid was identified as pB-MaPAH1.2 cDNA.

(2) Sequence Analysis

The cDNA sequence (SEQ ID NO: 4) of the MaPAH1.1 gene includes CDS (SEQ ID NO: 3) consisting of a sequence of the nucleotides 1 to 3987 and ORF (SEQ ID NO: 1) consisting of a sequence of the nucleotides 1 to 3984. A deduced amino acid sequence encoded by the MaPAH1.1 gene is shown in SEQ ID NO: 2. The genomic sequence of the MaPAH1.1 gene was compared with the ORF sequence (FIG. 1). The results suggest that the genomic sequence of the MaPAH1.1 gene is composed of eleven exons and ten introns.

The cDNA sequence (SEQ ID NO: 9) of the MaPAH1.2 gene includes CDS (SEQ ID NO: 8) consisting of a sequence of the nucleotides 72 to 3791 and ORF (SEQ ID NO: 6) consisting of a sequence of the nucleotides 72 to 3788. A deduced amino acid sequence encoded by the MaPAH1.2 gene is shown in SEQ ID NO: 7. The genomic sequence of the MaPAH1.2 gene was compared with the ORF sequence (FIG. 2). The genomic sequence of the MaPAH1.2 gene is composed of eight exons and seven introns.

The cDNA sequences of MaPAH1.1 and MaPAH1.2 and deduced amino acid sequences thereof are respectively shown in FIG. 3 and FIG. 4.

The deduced amino acid sequences of MaPAH1.1 and MaPAH1.2 were subjected to homology search against amino acid sequences in GenBank with the BLASTp program. Both amino acid sequences gave a hit with nuclear elongation and deformation protein 1 putative protein (AAW42851) derived from *Cryptococcus neoformans* var. *neoformans* JEC21 with the highest scores, but the identities thereof were low, i.e., 25.9% and 26.6%, respectively.

The amino acid sequences of MaPAH1.1 and MaPAH1.2 derived from *M. alpina* of the present invention have identities of 22.7% and 22.5%, respectively, with the amino acid sequence of ScPAH1 protein, which has been functionally analyzed, among PAP1 homologs of fungi. The amino acid sequences of MaPAH1.1 and MaPAH1.2 derived from *M. alpina* in the present invention were compared with the amino acid sequences of known ScPAH1 and mouse-derived lipin (FIG. 5). In the PAP1 family enzymes, the amino acid sequence of the N-terminal region is well conserved and is called lipin, N-terminal conserved region (pfam04571). In also MaPAH1.1 and MaPAH1.2 derived from *M. alpina* of the present invention, the known enzyme and the N-terminal region are relatively well conserved. In addition, the DIDGT sequence indicated with double underline in FIG. 5 is haloacid dehalogenase (HAD)-like protein superfamily enzyme and is consistent with the motif of the conserved DXDX(T/V) catalytic site.

The CDS sequences of MaPAH1.1 and MaPAH1.2 were compared with each other to show an identity of 54.7% (FIG. 6), while the identity between the deduced amino acid sequences was 35.6% (FIG. 7).

Example 5

Expression of MaPAH1.1 and MaPAH1.2 in Yeast

Construction of Expression Vector of MaPAH1.1 and MaPAH1.2:

In order to express MaPAH1.1 in yeast, expression vectors were constructed as follows.

Yeast expression vector pYE22m (Biosci. Biotech. Biochem., 59, 1221-1228, 1995) was digested with a restriction enzyme EcoRI, and the ends were blunted with a Blunting Kit (TaKaRa Bio Inc.). The resulting fragment and a linker, pNotI, phosphorylated (8-mer) (TaKaRa Bio Inc.) were linked to each other using ligation high (TOYOBO) to construct vector pYE22mN. The vector pYE22mN was digested with restriction enzymes NotI and KpnI, and the resulting fragment was linked to a DNA fragment of about 4.2 kbp obtained by digestion of plasmid pB-MaPAH1.1 cDNA with restriction enzymes NotI and KpnI to provide plasmid pYE-MaPAH1.1. Separately, vector pYE22mN was digested with restriction enzymes NotI and KpnI, and the resulting fragment was linked to a DNA fragment of about 3.8 kbp obtained by digestion of plasmid pB-MaPAH1.2 cDNA with restriction enzymes NotI and KpnI to provide plasmid pYE-MaPAH1.2.

Preparation of *S. cerevisiae* ΔScpah1:URA3 Strain

In order to clone an ScPAH1 gene derived from *S. cerevisiae* strain S288C, the following primers were prepared:

```
Primer KpnI-PAH1-F:
                                               (SEQ ID NO: 17)
5'-GGTACCATGCAGTACGTAGGCAGAGCTC-3',
and Primer XhoI-PAH1-R:
                                               (SEQ ID NO: 18)
5'-CTCGAGTTAATCTTCGAATTCATCTTCG-3'.
```

*S. cerevisiae* strain S288C was cultured in an YPD (2% yeast extract, 1% polypeptone, 2% glucose) liquid medium at 30° C. overnight. From the cells, DNA was extracted using Dr. GenTLE (from yeast) (TaKaRa Bio Inc.), and the ScPAH1 gene was amplified by PCR with ExTaq using the resulting DNA as a template and primers KpnI-PAH1-F and XhoI-PAH1-R. The resulting DNA fragment of about 2.5 kbp was cloned using a TOPO TA cloning Kit, and a clone having a correct nucleotide sequence was identified as pCR-ScPAH1. A DNA fragment of about 0.4 kbp obtained by digestion of pCR-ScPAH1 with restriction enzymes EcoRI and EcoRV and a DNA fragment of about 2.1 kbp obtained by digestion of pCR-ScPAH1 with restriction enzymes EcoRV and XhoI were ligated to vector pBluescriptIISK+digested by restriction enzymes EcoRI and XhoI to prepare plasmid pBScPAH1. Plasmid pBScPAH1 was digested with restriction enzymes EcoRV and HincII and was ligated to a DNA fragment of about 1.2 kbp obtained by digestion of plasmid pURA34 (Japanese Unexamined Patent Application Publication No. 2001-120276) with a restriction enzyme HindIII and then blunt-ended. The resulting product having the URA3 gene in the same direction as that of the ScPAH1 gene was determined as plasmid pBΔpah1:URA3. Subsequently, S. cerevisiae strain YPH499 (ura3-52 lys2-801amber ade2-101ochre trp1-Δ63 his3-Δ200 leu2-Δ1 a) (STARATAGENE), as a host, was transformed with a DNA fragment obtained by digestion of plasmid pBΔpah1:URA3 with a restriction enzyme EcoRI. Transformed strain was selected by the ability to grow on an SC-Ura agar medium (one liter of the medium includes 6.7 g of yeast nitrogen base w/o amino acids (DIFCO), 20 g of glucose, 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, and 1.2 g of tryptophan), and an agar medium (2% agar)). A strain that was confirmed by PCR that the Δpah1:URA3 construction was introduced thereinto and that the ScPAH1 gene was disrupted was determined as a ΔScpah1:URA3 strain.

Acquisition of Transformed Strain:

The ΔScpah1:URA3 strain was used as a host and transformed with plasmid pYE22m, pYE-MaPAH1.1, or pYE-MaPAH1.2. Transformed strains were selected by the ability to grow on an SC-Ura, Trp agar medium (one liter of the medium includes 6.7 g of yeast nitrogen base w/o amino acids (DIFCO), 20 g of glucose, 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, and 6 g of threonine), and an agar medium (2% agar)). Arbitrary two strains from the respective strains transformed with each plasmid (control strains transformed with plasmid pYE22m: C1 and C2, strains transformed with plasmid pYE-MaPAH1.1: MaPAH1.1-1 and MaPAH1.1-2, and strains transformed with plasmid pYE-MaPAH1.2: MaPAH1.2-1 and MaPAH1.2-2) were used the subsequent experiments.

Example 6

Measurement of $Mg^{2+}$-Dependent Phosphatidic Acid Phosphatase Activity (PAP1 Activity)

Each transformed yeast strain was inoculated into 100 mL of an SC-Ura, Trp liquid medium and shake-cultured at 30° C. for one day. A crude enzyme solution was prepared from the resulting culture solution as follows. In particular, the procedure was conducted at 4° C. or in ice. The cells were collected from the culture solution by centrifugation and were washed with water. Subsequently, the cells were suspended in 5 mL of buffer A (50 mM Tris-HCl (pH 7.5), 0.3 M sucrose, 10 mM mercaptoethanol, 0.5 mM phenylmethylsulfonyl fluoride (PMSF)). The cells were disrupted by treatment with a french press (Thermo Fisher Scientific), Mini-Cell, at 16 kPa three times. The cell lysate was subjected to centrifugation at 1500×g for 10 min, and the supernatant was collected as a crude enzyme solution. The concentration of protein contained in the crude enzyme solution was measured with Protein Assay CBB Solution (5×) (Nacalai Tesque).

The PAP1 activity was measured by a modified method by Gil-Soo, et al. (J. Biol. Chem., 282 (51), 37026-37035, (2007)) as follows. Since S. cerevisiae cannot synthesize linoleic acid, 1,2-dilinoleoyl-sn-glycero-3-phosphate (18:2-PA) was used as the substrate of PAP. Five hundred microliters of a reaction solution was used. The composition of the reaction solution was 100 μL of the crude enzyme solution, 50 mM Tris-HCl (pH 7.5), 100 μg/mL of 1,2-dilinoleoyl-sn-glycero-3-phosphate, monosodium salt (Avanti Polar Lipids, Inc.), 1 mM $MgCl_2$, and 10 mM 2-mercaptoethanol. The reaction solution was maintained at 25° C. for 30 min, and then the reaction was terminated by addition of chloroform:methanol (1:2). Lipids were extracted by a Bligh-Dyer method. The lipids were fractionated on a silica gel 60 plate (Merck) by thin layer chromatography (TLC) using hexane:diethyl ether:acetic acid=70:30:1 as the eluent. The lipids were visualized by spraying a primulin solution (0.015% primulin in aqueous 80% acetone) and then irradiated with UV light. The diacylglycerol (DG) fraction was scraped from the plate and fatty acids were converted to methyl ester by a hydrochloric acid/methanol method. Subsequently, fatty acid methyl ester was extracted with hexane, and hexane was distilled off, followed by gas chromatographic analysis.

Table 2 shows the amounts of linoleic acid transferred into the DG fraction per protein in the crude enzyme solution.

TABLE 2

| Transformed strain | 18:2 (μg/mg protein) |
| --- | --- |
| C1 | 15.43 |
| C2 | 17.53 |
| MaPAH1.1-1 | 56.03 |
| MaPAH1.1-2 | 44.34 |
| MaPAH1.2-1 | 19.45 |
| MaPAH1.2-2 | 20.90 |

As shown in Table 2, in comparison with C1 and C2 transformed with pYE22m, the activity of converting 18:2-PA to dilinolein (18:2-DG) was about 3-fold in MaPAH1.1-1 and MaPAH1.1-2 expressing MaPAH1.1 and about 1.2-fold in MaPAH1.2-1 and MaPAH1.2-2 expressing MaPAH1.2. This suggests that MaPAH1.1 and MaPAH1.2 have PAP activity.

The dependency of the PAP activity on $Mg^{2+}$ was investigated as follows: Five hundred microliters of a reaction solution was used. The reaction and analysis were performed under the same conditions as above except that the composition of the reaction solution was 100 μL of the crude enzyme solution, 50 mM Tris-HCl (pH 7.5), 100 μg/mL of 1,2-dilinoleoyl-sn-glycero-3-phosphate, monosodium salt (Avanti Polar Lipids, Inc.), 2 mM EDTA, and 10 mM 2-mercaptoethanol. Table 3 shows the amounts of linoleic acid transferred into the DG fraction per protein in the crude enzyme solution.

TABLE 3

| Transformed strain | 18:2 (μg/mg protein) |
|---|---|
| C1 | 11.17 |
| C2 | 10.77 |
| MaPAH1.1-1 | 13.06 |
| MaPAH1.1-2 | 11.39 |
| MaPAH1.2-1 | 12.52 |
| MaPAH1.2-2 | 10.93 |

As shown in Table 3, in every strain, the activity of converting 18:2-PA to dilinolein (18:2-DG) was approximately the same.

This suggests that the PAP activity of MaPAH1.1 and MaPAH1.2 depends on $Mg^{2+}$ and that MaPAH1.1 and MaPAH1.2 have PAP1 activity.

Example 7

Amount of Produced Triacylglycerol

Triacylglycerol (throughout the specification, referred to as triglyceride or TG), which is a reserve lipid, is a lipid obtained by further acylating diacylglycerol which is a product of PAP protein. The amounts of TG produced by yeast transformants in which MaPAH1.1 or MaPAH1.2 was highly expressed were measured.

The transformant cells, ScPAH1-deficient yeast strain host, were inoculated in 10 mL of an SD-Ura, Trp liquid medium and were statically cultured at 30° C. for 3 days. One milliliter of the culture solution was inoculated in 10 mL of a YPDA (2% yeast extract, 1% polypeptone, 2% glucose, 0.008% adenine sulfate) liquid medium, followed by shake culture at 30° C. for one day (n=3). The cells were collected by centrifugation of the culture solution, washed with water, and lyophilized. Chloroform and methanol (2:1) were added to the dried cells. The cells were repeatedly disrupted with glass beads, and lipids were extracted with 8 mL in total of a solvent. The extracted lipids were fractionated by TLC as in above, and the TG fraction was scraped and analyzed. Table 4 shows the results.

TABLE 4

Amount* of TG produced in each medium

| Transformed strain | mg/L |
|---|---|
| C1 | 11.01 ± 1.27 |
| C2 | 11.54 ± 0.54 |
| MaPAH1.1-1 | 16.01 ± 2.45 |
| MaPAH1.1-2 | 17.09 ± 1.41 |
| MaPAH1.2-1 | 14.29 ± 0.87 |
| MaPAH1.2-2 | 13.32 ± 0.78 |

*In terms of fatty acid

As shown in Table 4, the amount of TG was about 1.5-fold in the MaPAH1.1 high expression strain and was about 1.2-fold in the MaPAH1.2 high expression strain compared with that in the control.

Example 8

Substrate Specificity of MaPAH1.1 and MaPAH1.2

The ΔScpah1:URA3 strain, the host, was transformed with plasmid pYE22m, pYE-MaPAH1.1, or pYE-MaPAH1.2. Four strains of each transformant were used in the following experiments. The strains transformed with plasmid pYE22m were used as a control.

The yeast transformants were each inoculated in 10 mL of an SC-Ura, Trp liquid medium and were statically cultured at 27.5° C. overnight. The resulting culture solutions were each inoculated in 40 mL of an SC-Ura, Trp liquid medium at an amount of 1/10 in duplicate and were statically cultured at 27.5° C. for two days. Crude enzyme solutions were prepared from the resulting culture solutions as in Example 6, and the protein concentrations thereof were measured.

The PAP1 activity was measured as in Example 6 except that 1,2-dilinoleoyl-sn-glycero-3-phosphate (18:2-PA) and 1,2-dioleoyl-sn-glycero-3-phosphate (18:1-PA) were used as substrates of PAP.

Tables 5 and Table 6 respectively show the amounts of linoleic acid (18:2) and oleic acid (18:1) transferred into the diacylglycerol (DG) fraction per crude enzyme solution protein.

TABLE 5

18:2 in DG per protein (μg/mg · protein)

| Sample name | Control | | MaPAH1.1 | | MaPAH1.2 | |
|---|---|---|---|---|---|---|
| | mean | SD | mean | SD | mean | SD |
| | 13.72 | 2.74 | 25.50 | 6.75 | 18.19 | 1.43 |

TABLE 6

18:1 in DG per protein (μg/mg · protein)

| Sample name | Control | | MaPAH1.1 | | MaPAH1.2 | |
|---|---|---|---|---|---|---|
| | mean | SD | mean | SD | mean | SD |
| | 15.14 | 0.88 | 29.16 | 7.04 | 16.69 | 1.05 |

When the substrate used was 18:2-PA, the activities of MaPAH1.1 and MaPAH1.2 derived from *Mortierella* were 1.9-fold and 1.3-fold, respectively, compared with that of the control.

When the substrate used was 18:1-PA, the activities of MaPAH1.1 and MaPAH1.2 were 1.9-fold and 1.1-fold, respectively, compared with that of the control. The 18:1 is a fatty acid that yeast intrinsically possesses and is therefore originally present in DG of the crude enzyme solution. However, no difference was observed in the amount of 18:1 in DG in the crude enzyme solution when the substrate was not added. Accordingly, it can be assumed that the differences in activity of MaPAH1.1 and MaPAH1.2 from the control shown in Table 6 are based on the effect against 18:1-PA added as a substrate.

In comparison of activities of the same enzyme against different substrates, MaPAH1.1 increased both 18:1 and 18:2 by 1.9-fold compared with the control, while MaPAH1.2 increased the amount of 18:1 by 1.1-fold and the amount of 18:2 by 1.3-fold compared with the control. This suggests that MaPAH1.1 exhibits its activity on both 18:1-PA and 18:2-PA equally, but in MaPAH1.2, the activity on 18:2-PA is higher than that on 18:1-PA.

These results suggest that MaPAH1.1 and MaPAH1.2 have PAP activity. In addition, MaPAH1.2 shows higher activity on 18:2-PA than on 18:1-PA, which suggests that MaPAH1.2 shows a higher activity on phosphatidic acid having a fatty acid portion with a higher degree of unsaturation.

SEQUENCE LISTING FREE TEXT

SEQ ID NO: 11: primer
SEQ ID NO: 12: primer
SEQ ID NO: 13: primer
SEQ ID NO: 14: primer
SEQ ID NO: 15: primer
SEQ ID NO: 16: primer
SEQ ID NO: 17: primer
SEQ ID NO: 18: primer

The invention claimed is:

1. A cDNA or recombinant vector comprising:
   (a) a nucleotide sequence encoding a protein that consists of an amino acid sequence having deletion, substitution, or addition of 1-50 amino acids in the amino acid sequence set forth in SEQ ID NO: 2 and has a phosphatidic acid phosphatase activity; or
   (b) a nucleotide sequence encoding a protein that consists of an amino acid sequence having an identity of 95% or more with the amino acid sequence set forth in SEQ ID NO: 2 and has a phosphatidic acid phosphatase activity, wherein 100 amino acids at the N-terminus and the DXDX(T/V) catalytic site motif in the protein are identical to SEQ ID NO: 2.

2. A cDNA or recombinant vector comprising:
   (a) a nucleotide sequence encoding a protein that consists of an amino acid sequence having deletion, substitution, or addition of 1-50 amino acids in the amino acid sequence set forth in SEQ ID NO: 2 and has an activity that enhances generation of diacylglycerol (DG) and/or triglyceride (TG) from phosphatidic acid (PA) in a PAH1-deficient yeast strain; or
   (b) a nucleotide sequence encoding a protein that consists of an amino acid sequence having an identity of 95% or more with the amino acid sequence set forth in SEQ ID NO: 2 and has an activity that enhances generation of DG and/or TG from PA in a PAH1-deficient yeast strain,
   wherein 100 amino acids at the N-terminus and the DXDX(T/V) catalytic site motif in the protein are identical to SEQ ID NO: 2.

3. A cDNA or recombinant vector comprising a nucleic acid sequence according to any one of (a) to (d) below:
   (a) the nucleotide sequence set forth in SEQ ID NO: 1;
   (b) a nucleotide sequence encoding a protein consisting of the amino acid sequence set forth in SEQ ID NO: 2;
   (c) the nucleotide sequence set forth in SEQ ID NO: 4; and
   (d) the nucleotide sequence set forth in SEQ ID NO: 5.

4. An isolated transformant transformed with the recombinant vector according to claim 1.

5. A method for producing a lipid composition, comprising:
   culturing the transformant according to claim 4; and
   collecting a lipid from the culture,
   wherein the lipid comprises diacylglycerol (DG) and/or triglyceride (TG).

* * * * *

```
                         SEQUENCE LISTING

<160> NUMBER OF SEQ ID NOS: 20

<210> SEQ ID NO 1
<211> LENGTH: 3984
<212> TYPE: DNA
<213> ORGANISM: Mortierella alpina
<220> FEATURE:
<221> NAME/KEY: CDS
<222> LOCATION: (1)..(3984)
<223> OTHER INFORMATION:

<400> SEQUENCE: 1 atg cag tcc gtg gga agc ttc ttc tcc act gtc tca agg ttc tac aat      48
Met Gln Ser Val Gly Ser Phe Phe Ser Thr Val Ser Arg Phe Tyr Asn
1               5                   10                  15 gag ctc aat cca gcc acg ctt tcg ggc gcc att gac gtg gtc gtg gtc      96
Glu Leu Asn Pro Ala Thr Leu Ser Gly Ala Ile Asp Val Val Val Val
                20                  25                  30 gag caa gcc gat ggt gaa tta gca tgc tca cca ttt cat gtc cgc ttt     144
Glu Gln Ala Asp Gly Glu Leu Ala Cys Ser Pro Phe His Val Arg Phe
            35                  40                  45 ggc aaa ctg agc att ctc cga ccg cag gaa aaa gtg gtg gag gtg acc     192
Gly Lys Leu Ser Ile Leu Arg Pro Gln Glu Lys Val Val Glu Val Thr
        50                  55                  60 gtc aac ggt cgc gtc gtt gat ttt cct atg aag gtt ggc gat gca ggc     240
Val Asn Gly Arg Val Val Asp Phe Pro Met Lys Val Gly Asp Ala Gly
65                  70                  75                  80 gaa gcc ttc ttt gtt ttt gag act gag cag gac gtg ccc gaa gag ttt     288
Glu Ala Phe Phe Val Phe Glu Thr Glu Gln Asp Val Pro Glu Glu Phe
                85                  90                  95 gcc acg tct cca cta gcg gga ccc aac aca gac aaa gtt gag gag gac     336
Ala Thr Ser Pro Leu Ala Gly Pro Asn Thr Asp Lys Val Glu Glu Asp
                100                 105                 110 att gac tat ctg gat cta gcc gaa ggg cat agc acc gtg aca tat ccg     384
Ile Asp Tyr Leu Asp Leu Ala Glu Gly His Ser Thr Val Thr Tyr Pro
            115                 120                 125 cct gac gat ata gtc tta gat gcg ggc tat gtc agc gcc cac agt ggg     432
Pro Asp Asp Ile Val Leu Asp Ala Gly Tyr Val Ser Ala His Ser Gly
        130                 135                 140 cat gga tca gag ttt gaa gaa gac gag aga gca gac ttg tcg cct gaa     480
His Gly Ser Glu Phe Glu Glu Asp Glu Arg Ala Asp Leu Ser Pro Glu
145                 150                 155                 160 ttt gac aaa aag cca gat tac gca tcc gcg gtc aaa tac ggc ggt aca     528
Phe Asp Lys Lys Pro Asp Tyr Ala Ser Ala Val Lys Tyr Gly Gly Thr
                165                 170                 175 aat gga caa ggg aga cac cta ggc agt gct aat gag gca acg acg tct     576
Asn Gly Gln Gly Arg His Leu Gly Ser Ala Asn Glu Ala Thr Thr Ser
            180                 185                 190 gta cat gct ttc atg gag cgg caa gtt caa cga tgg tcg ctt acc atg     624
Val His Ala Phe Met Glu Arg Gln Val Gln Arg Trp Ser Leu Thr Met
        195                 200                 205 tcc cta cca ccc tct ccg gtg tta aag tct cgc gac att atg gag aac     672
Ser Leu Pro Pro Ser Pro Val Leu Lys Ser Arg Asp Ile Met Glu Asn
    210                 215                 220 ttt cag cct att gac tcg gcg ggc cct ttc gat aat agt cga gag gat     720
Phe Gln Pro Ile Asp Ser Ala Gly Pro Phe Asp Asn Ser Arg Glu Asp
```

-continued

| | | | | |
|---|---|---|---|---|
| | 225 | 230 | 235 | 240 | tct gga cgc ctg ctc gcg cca gag act atc gcc gtt agc aat gga ggc    768
Ser Gly Arg Leu Leu Ala Pro Glu Thr Ile Ala Val Ser Asn Gly Gly
                245                 250                 255 agc agt gga tct ctg ttt cat cct aag gag ggc atg ata atg gac atg    816
Ser Ser Gly Ser Leu Phe His Pro Lys Glu Gly Met Ile Met Asp Met
            260                 265                 270 act ggc tac aag acc gag gac tct gac ctg aat tcc gat gcg tct gat    864
Thr Gly Tyr Lys Thr Glu Asp Ser Asp Leu Asn Ser Asp Ala Ser Asp
        275                 280                 285 gaa cat gat gta ggc atg gct ggc gct ttg aat ggt cgc cat cgg cgc    912
Glu His Asp Val Gly Met Ala Gly Ala Leu Asn Gly Arg His Arg Arg
    290                 295                 300 aaa agg gct gct cgg cgg aaa agg aga ggg ccg gtg cat ggc gtc aac    960
Lys Arg Ala Ala Arg Arg Lys Arg Arg Gly Pro Val His Gly Val Asn
305                 310                 315                 320 tct caa gac aac ctg gcc act gaa act ccc tca att aca gcg cat gtc   1008
Ser Gln Asp Asn Leu Ala Thr Glu Thr Pro Ser Ile Thr Ala His Val
                325                 330                 335 ctc agc agt ctc gac cct cgc ttg ccg ttg cga cct act gcg cga cct   1056
Leu Ser Ser Leu Asp Pro Arg Leu Pro Leu Arg Pro Thr Ala Arg Pro
            340                 345                 350 gct cta cgc ccc aaa gct aac aac ggg ttg ggc act cta ccg aat cgc   1104
Ala Leu Arg Pro Lys Ala Asn Asn Gly Leu Gly Thr Leu Pro Asn Arg
        355                 360                 365 cgt tcg tca tcg atg ccg aat ctt aaa gat ttc gta ggt gag aat aac   1152
Arg Ser Ser Ser Met Pro Asn Leu Lys Asp Phe Val Gly Glu Asn Asn
    370                 375                 380 agt ttg tcg cca agc gtg ccg gcg ata atg cga cgc ttt cct tcg aag   1200
Ser Leu Ser Pro Ser Val Pro Ala Ile Met Arg Arg Phe Pro Ser Lys
385                 390                 395                 400 acg tta aac tca aag ttt tcc gca aga agc gac atc aaa gat ggg acc   1248
Thr Leu Asn Ser Lys Phe Ser Ala Arg Ser Asp Ile Lys Asp Gly Thr
                405                 410                 415 agt tca agc agc tcc gta gcc tcc tcg cct cca ccg tca gtt gcc aac   1296
Ser Ser Ser Ser Ser Val Ala Ser Ser Pro Pro Pro Ser Val Ala Asn
            420                 425                 430 cag cag agc cct aaa aac cgc cac cat cac cat cat cac cac aaa gag   1344
Gln Gln Ser Pro Lys Asn Arg His His His His His His His Lys Glu
        435                 440                 445 cac acc gaa gga agc cat ccc cgt cgc cac tcg cac aaa cct tca cag   1392
His Thr Glu Gly Ser His Pro Arg Arg His Ser His Lys Pro Ser Gln
    450                 455                 460 caa gtg caa gtg aaa aaa ccc ccg ccc aga tcc aat cca gct gtt aat   1440
Gln Val Gln Val Lys Lys Pro Pro Pro Arg Ser Asn Pro Ala Val Asn
465                 470                 475                 480 gcg ctg agc gat acg gag ctc gag tat caa acg ccg cga aca aca gca   1488
Ala Leu Ser Asp Thr Glu Leu Glu Tyr Gln Thr Pro Arg Thr Thr Ala
                485                 490                 495 gct act caa gaa tca gag tgg tcc tgg gga tgg ggc agc tta ccg gtt   1536
Ala Thr Gln Glu Ser Glu Trp Ser Trp Gly Trp Gly Ser Leu Pro Val
            500                 505                 510 aaa aat gac ggt cta ggc aca ggg gaa gca gat cac aag gag cat cac   1584
Lys Asn Asp Gly Leu Gly Thr Gly Glu Ala Asp His Lys Glu His His
        515                 520                 525 tct agt cat cca tca atc gac att cca gcc cca cgg aaa cct gtg ttg   1632
Ser Ser His Pro Ser Ile Asp Ile Pro Ala Pro Arg Lys Pro Val Leu
    530                 535                 540 aac gag atg gag att gac ggg act gtg tac aga ctc gcc atc agc ttg   1680

```
                                                     -continued

Asn Glu Met Glu Ile Asp Gly Thr Val Tyr Arg Leu Ala Ile Ser Leu
545                 550                 555                 560 tgt ccg ggt gat gaa ttc gga aaa gat ttg gaa gcc agc gaa gca ttg    1728
Cys Pro Gly Asp Glu Phe Gly Lys Asp Leu Glu Ala Ser Glu Ala Leu
                565                 570                 575 ttt gcc acc aat cag gtt tcg ttc gat gag ttc gcg aaa gac cca ctc    1776
Phe Ala Thr Asn Gln Val Ser Phe Asp Glu Phe Ala Lys Asp Pro Leu
                580                 585                 590 aag act ctc aat aac aag aat ttg gtc tgc ctg atc aat gac cgg tat    1824
Lys Thr Leu Asn Asn Lys Asn Leu Val Cys Leu Ile Asn Asp Arg Tyr
            595                 600                 605 ttt act tgg aca gct gcg gga cca tat ctt tcc tca ctg atg ctc ttc    1872
Phe Thr Trp Thr Ala Ala Gly Pro Tyr Leu Ser Ser Leu Met Leu Phe
610                 615                 620 cgg aag cct ctc tct gac gaa acg ctc cat cag ctt tca gcc aag gac    1920
Arg Lys Pro Leu Ser Asp Glu Thr Leu His Gln Leu Ser Ala Lys Asp
625                 630                 635                 640 tcg cgg cat cta tca gat cga ctc gct gtg caa gat gag ccc cca acc    1968
Ser Arg His Leu Ser Asp Arg Leu Ala Val Gln Asp Glu Pro Pro Thr
                645                 650                 655 cgt ttc ggc gct ctc tcc aga tgg cta agg gga tca caa acc tcg tcc    2016
Arg Phe Gly Ala Leu Ser Arg Trp Leu Arg Gly Ser Gln Thr Ser Ser
                660                 665                 670 caa ttg agc gcg atg gag caa ggg caa aga caa cgt act ccc agt acc    2064
Gln Leu Ser Ala Met Glu Gln Gly Gln Arg Gln Arg Thr Pro Ser Thr
            675                 680                 685 aac gat gcc ttg cag cct gct cag tta gag gag agt caa gct tta cag    2112
Asn Asp Ala Leu Gln Pro Ala Gln Leu Glu Glu Ser Gln Ala Leu Gln
690                 695                 700 agc gtg aaa gtc gaa tcg att aag cac act tcc gga tca cat tca tca    2160
Ser Val Lys Val Glu Ser Ile Lys His Thr Ser Gly Ser His Ser Ser
705                 710                 715                 720 ctt cta cgc gct cct aaa cca atg act cgt agc acc tct ctg ccg atc    2208
Leu Leu Arg Ala Pro Lys Pro Met Thr Arg Ser Thr Ser Leu Pro Ile
                725                 730                 735 gac gaa ggg atc gcc ggg tct ata tca gac gag tac gct gga agc tcg    2256
Asp Glu Gly Ile Ala Gly Ser Ile Ser Asp Glu Tyr Ala Gly Ser Ser
                740                 745                 750 cct ccg aca cat tct gcg ctc aag agc agt aga cgg tat gcg aaa acg    2304
Pro Pro Thr His Ser Ala Leu Lys Ser Ser Arg Arg Tyr Ala Lys Thr
            755                 760                 765 ctt cgc ttg aca tct gaa cag ttg aaa tca cta aat ttg aaa aaa ggc    2352
Leu Arg Leu Thr Ser Glu Gln Leu Lys Ser Leu Asn Leu Lys Lys Gly
770                 775                 780 gcc aat aca ttg acg ttt tca gta acg tca agt tat caa ggc aaa gca    2400
Ala Asn Thr Leu Thr Phe Ser Val Thr Ser Ser Tyr Gln Gly Lys Ala
785                 790                 795                 800 gtt tgt tcc gcc aaa ttg ttt ctg tgg gac cat gac tac caa gtc gtc    2448
Val Cys Ser Ala Lys Leu Phe Leu Trp Asp His Asp Tyr Gln Val Val
                805                 810                 815 ata tcg gac att gat ggc acg att aca aag tcg gac gct ctc gga cac    2496
Ile Ser Asp Ile Asp Gly Thr Ile Thr Lys Ser Asp Ala Leu Gly His
                820                 825                 830 atc ttt acc atg gca gga aag gat tgg acc cat tcg ggt gtc gcc aaa    2544
Ile Phe Thr Met Ala Gly Lys Asp Trp Thr His Ser Gly Val Ala Lys
            835                 840                 845 ctt tac acg gac atc gtc aac aat ggg tat cat att ttg tac ttg acc    2592
Leu Tyr Thr Asp Ile Val Asn Asn Gly Tyr His Ile Leu Tyr Leu Thr
850                 855                 860
```

| | | |
|---|---|---|
| tca agg gcc att gga cag gca gac tac aca cga aag tac ctc aag aac<br>Ser Arg Ala Ile Gly Gln Ala Asp Tyr Thr Arg Lys Tyr Leu Lys Asn<br>865                          870                   875                 880 | | 2640 |
| gtg gag caa aat aac tac cag tta ccg gat gga ccg gtg atc atg agc<br>Val Glu Gln Asn Asn Tyr Gln Leu Pro Asp Gly Pro Val Ile Met Ser<br>                  885                   890                 895 | | 2688 |
| cct gat cgc ttg atg acc gcc ttc cac agg gag gtg att atg agg aag<br>Pro Asp Arg Leu Met Thr Ala Phe His Arg Glu Val Ile Met Arg Lys<br>            900                  905                 910 | | 2736 |
| cca gaa gaa ttc aag atg gca tgt ctg cgt gac att cgg agg ctg ttt<br>Pro Glu Glu Phe Lys Met Ala Cys Leu Arg Asp Ile Arg Arg Leu Phe<br>                  915                  920                 925 | | 2784 |
| gga gat cgc aac ccc ttc tat gcc ggg ttt gga aac aga atc acg gac<br>Gly Asp Arg Asn Pro Phe Tyr Ala Gly Phe Gly Asn Arg Ile Thr Asp<br>930                          935                   940 | | 2832 |
| gca ctg tcc tac agg agc gtt aat gtc ccc tca tct cgg ata ttt aca<br>Ala Leu Ser Tyr Arg Ser Val Asn Val Pro Ser Ser Arg Ile Phe Thr<br>945                          950                   955                 960 | | 2880 |
| att gat tcg gga ggt gaa gtc aag ctg gag ctc ctc agc agc tac aaa<br>Ile Asp Ser Gly Gly Glu Val Lys Leu Glu Leu Leu Ser Ser Tyr Lys<br>                  965                  970                 975 | | 2928 |
| tca tca tat ctc gcg ttg aac gat ctc gtg aat gag atc ttt cca gga<br>Ser Ser Tyr Leu Ala Leu Asn Asp Leu Val Asn Glu Ile Phe Pro Gly<br>            980                   985                 990 | | 2976 |
| aaa aga cag gca ccc gag ttc aat  gac tgg aac ttt tgg  cgg gcg ccc<br>Lys Arg Gln Ala Pro Glu Phe Asn  Asp Trp Asn Phe Trp  Arg Ala Pro<br>                  995                   1000                1005 | | 3024 |
| ttg cca  gat atc gag ctt cca  gtt gcg ccg tct cat  caa tac gcc<br>Leu Pro  Asp Ile Glu Leu Pro  Val Ala Pro Ser His  Gln Tyr Ala<br>    1010                   1015                  1020 | | 3069 |
| cct aca  gcg gtg ccg ggc gag  tac aat gca caa  gga tat tct gca<br>Pro Thr  Ala Val Pro Gly Glu  Tyr Asn Ala Gln  Gly Tyr Ser Ala<br>    1025                   1030                  1035 | | 3114 |
| ggt cct  ggc cgg ttg gga gtg  ata cgg agc ctt acc  agt tcc ctc<br>Gly Pro  Gly Arg Leu Gly Val  Ile Arg Ser Leu Thr  Ser Ser Leu<br>    1040                   1045                  1050 | | 3159 |
| acc tca  gca gga ccg ctc aag  acg agg acc gct atc  cca att ttt<br>Thr Ser  Ala Gly Pro Leu Lys  Thr Arg Thr Ala Ile  Pro Ile Phe<br>    1055                   1060                  1065 | | 3204 |
| acc tca  aat tcg ccc cct cct  ccg aat tcc tac cca  tcg gcg atg<br>Thr Ser  Asn Ser Pro Pro Pro  Pro Asn Ser Tyr Pro  Ser Ala Met<br>    1070                   1075                  1080 | | 3249 |
| aag ccc  cat gca ccg cat cag  tcc caa cca gcc tcc  tcc tcg cct<br>Lys Pro  His Ala Pro His Gln  Ser Gln Pro Ala Ser  Ser Ser Pro<br>    1085                   1090                  1095 | | 3294 |
| caa ccc  ccc gca tca gcg ccg  tca gga ctg cag atc  gct gat agg<br>Gln Pro  Pro Ala Ser Ala Pro  Ser Gly Leu Gln Ile  Ala Asp Arg<br>    1100                   1105                  1110 | | 3339 |
| acc cgt  cga ctc tcg ctg tcg  ttg atg cga tat agc  agc cat tca<br>Thr Arg  Arg Leu Ser Leu Ser  Leu Met Arg Tyr Ser  Ser His Ser<br>    1115                   1120                  1125 | | 3384 |
| gct ccc  acg tcc gcg cca gtt  ttg aga act ttg acc  gac agt tcc<br>Ala Pro  Thr Ser Ala Pro Val  Leu Arg Thr Leu Thr  Asp Ser Ser<br>    1130                   1135                  1140 | | 3429 |
| gag ccc  aat gtc ggc att gac  agc ggt gat gca ggc  gct ctc tct<br>Glu Pro  Asn Val Gly Ile Asp  Ser Gly Asp Ala Gly  Ala Leu Ser<br>    1145                   1150                  1155 | | 3474 |
| gag ggg  aat cag gca ggt tta  gag cca aat cgc tca  cct cac ttg<br>Glu Gly  Asn Gln Ala Gly Leu  Glu Pro Asn Arg Ser  Pro His Leu<br>    1160                   1165                  1170 | | 3519 |

-continued

```
gga tcc aac act gat ggc gtt ttc cca ctg gac gtt cct gtt gtg      3564
Gly Ser Asn Thr Asp Gly Val Phe Pro Leu Asp Val Pro Val Val
    1175            1180                1185 aag aga aag gca tct ggt ttc tcg gtc tca ccg ccc cag ctt gcc      3609
Lys Arg Lys Ala Ser Gly Phe Ser Val Ser Pro Pro Gln Leu Ala
    1190            1195                1200 agt cga cta agt gag act gta atg cct ttt ctt cgc cga cga gca      3654
Ser Arg Leu Ser Glu Thr Val Met Pro Phe Leu Arg Arg Arg Ala
    1205            1210                1215 tcc aag ttg gag cag ggg cag gag cag cag cag gaa cag cag cag      3699
Ser Lys Leu Glu Gln Gly Gln Glu Gln Gln Gln Glu Gln Gln Gln
    1220            1225                1230 gaa cag gaa cag gaa cga gag cat gat gtc cag ctg ggt gca gca      3744
Glu Gln Glu Gln Glu Arg Glu His Asp Val Gln Leu Gly Ala Ala
    1235            1240                1245 gct gaa ggg gag cag ctt gct tac act cga gag tac ggg gaa gaa      3789
Ala Glu Gly Glu Gln Leu Ala Tyr Thr Arg Glu Tyr Gly Glu Glu
    1250            1255                1260 gaa gcc gct gct gga tat ctg gcg gag gac cat gaa ctc gga gag      3834
Glu Ala Ala Ala Gly Tyr Leu Ala Glu Asp His Glu Leu Gly Glu
    1265            1270                1275 gat gaa gag gat gaa gga gaa gga gca gat gga tat gtt ggt tat      3879
Asp Glu Glu Asp Glu Gly Glu Gly Ala Asp Gly Tyr Val Gly Tyr
    1280            1285                1290 tct gga gaa gag gat gaa ggt ctg gaa gaa gat cag ctc gag ggt      3924
Ser Gly Glu Glu Asp Glu Gly Leu Glu Glu Asp Gln Leu Glu Gly
    1295            1300                1305 gag gaa gac gag gat gag gat gac gat gat gta gag ctc aac att      3969
Glu Glu Asp Glu Asp Glu Asp Asp Asp Asp Val Glu Leu Asn Ile
    1310            1315                1320 gac gct ccg ttc cta                                              3984
Asp Ala Pro Phe Leu
    1325

<210> SEQ ID NO 2
<211> LENGTH: 1328
<212> TYPE: PRT
<213> ORGANISM: Mortierella alpina

<400> SEQUENCE: 2

Met Gln Ser Val Gly Ser Phe Phe Ser Thr Val Ser Arg Phe Tyr Asn
1               5                   10                  15

Glu Leu Asn Pro Ala Thr Leu Ser Gly Ala Ile Asp Val Val Val
            20                  25                  30

Glu Gln Ala Asp Gly Glu Leu Ala Cys Ser Pro Phe His Val Arg Phe
        35                  40                  45

Gly Lys Leu Ser Ile Leu Arg Pro Gln Glu Lys Val Val Glu Val Thr
    50                  55                  60

Val Asn Gly Arg Val Val Asp Phe Pro Met Lys Val Gly Asp Ala Gly
65                  70                  75                  80

Glu Ala Phe Phe Val Phe Glu Thr Glu Gln Asp Val Pro Glu Glu Phe
                85                  90                  95

Ala Thr Ser Pro Leu Ala Gly Pro Asn Thr Asp Lys Val Glu Glu Asp
            100                 105                 110

Ile Asp Tyr Leu Asp Leu Ala Glu Gly His Ser Thr Val Thr Tyr Pro
        115                 120                 125

Pro Asp Asp Ile Val Leu Asp Ala Gly Tyr Val Ser Ala His Ser Gly
    130                 135                 140
```

```
His Gly Ser Glu Phe Glu Glu Asp Glu Arg Ala Asp Leu Ser Pro Glu
145                 150                 155                 160

Phe Asp Lys Lys Pro Asp Tyr Ala Ser Ala Val Lys Tyr Gly Gly Thr
            165                 170                 175

Asn Gly Gln Gly Arg His Leu Gly Ser Ala Asn Glu Ala Thr Thr Ser
        180                 185                 190

Val His Ala Phe Met Glu Arg Gln Val Gln Arg Trp Ser Leu Thr Met
    195                 200                 205

Ser Leu Pro Pro Ser Pro Val Leu Lys Ser Arg Asp Ile Met Glu Asn
210                 215                 220

Phe Gln Pro Ile Asp Ser Ala Gly Pro Phe Asp Asn Ser Arg Glu Asp
225                 230                 235                 240

Ser Gly Arg Leu Leu Ala Pro Glu Thr Ile Ala Val Ser Asn Gly Gly
                245                 250                 255

Ser Ser Gly Ser Leu Phe His Pro Lys Glu Gly Met Ile Met Asp Met
            260                 265                 270

Thr Gly Tyr Lys Thr Glu Asp Ser Asp Leu Asn Ser Asp Ala Ser Asp
        275                 280                 285

Glu His Asp Val Gly Met Ala Gly Ala Leu Asn Gly Arg His Arg Arg
    290                 295                 300

Lys Arg Ala Ala Arg Arg Lys Arg Arg Gly Pro Val His Gly Val Asn
305                 310                 315                 320

Ser Gln Asp Asn Leu Ala Thr Glu Thr Pro Ser Ile Thr Ala His Val
                325                 330                 335

Leu Ser Ser Leu Asp Pro Arg Leu Pro Leu Arg Pro Thr Ala Arg Pro
            340                 345                 350

Ala Leu Arg Pro Lys Ala Asn Asn Gly Leu Gly Thr Leu Pro Asn Arg
        355                 360                 365

Arg Ser Ser Ser Met Pro Asn Leu Lys Asp Phe Val Gly Glu Asn Asn
    370                 375                 380

Ser Leu Ser Pro Ser Val Pro Ala Ile Met Arg Arg Phe Pro Ser Lys
385                 390                 395                 400

Thr Leu Asn Ser Lys Phe Ser Ala Arg Ser Asp Ile Lys Asp Gly Thr
                405                 410                 415

Ser Ser Ser Ser Ser Val Ala Ser Ser Pro Pro Ser Val Ala Asn
            420                 425                 430

Gln Gln Ser Pro Lys Asn Arg His His His His His His Lys Glu
        435                 440                 445

His Thr Glu Gly Ser His Pro Arg Arg His Ser His Lys Pro Ser Gln
    450                 455                 460

Gln Val Gln Val Lys Lys Pro Pro Arg Ser Asn Pro Ala Val Asn
465                 470                 475                 480

Ala Leu Ser Asp Thr Glu Leu Glu Tyr Gln Thr Pro Arg Thr Thr Ala
                485                 490                 495

Ala Thr Gln Glu Ser Glu Trp Ser Trp Gly Trp Gly Ser Leu Pro Val
            500                 505                 510

Lys Asn Asp Gly Leu Gly Thr Gly Glu Ala Asp His Lys Glu His His
        515                 520                 525

Ser Ser His Pro Ser Ile Asp Ile Pro Ala Pro Arg Lys Pro Val Leu
    530                 535                 540

Asn Glu Met Glu Ile Asp Gly Thr Val Tyr Arg Leu Ala Ile Ser Leu
545                 550                 555                 560
```

-continued

Cys Pro Gly Asp Glu Phe Gly Lys Asp Leu Glu Ala Ser Glu Ala Leu
            565                 570                 575

Phe Ala Thr Asn Gln Val Ser Phe Asp Glu Phe Ala Lys Asp Pro Leu
            580                 585                 590

Lys Thr Leu Asn Asn Lys Asn Leu Val Cys Leu Ile Asn Asp Arg Tyr
            595                 600                 605

Phe Thr Trp Thr Ala Ala Gly Pro Tyr Leu Ser Ser Leu Met Leu Phe
            610                 615                 620

Arg Lys Pro Leu Ser Asp Glu Thr Leu His Gln Leu Ser Ala Lys Asp
625                 630                 635                 640

Ser Arg His Leu Ser Asp Arg Leu Ala Val Gln Asp Glu Pro Pro Thr
            645                 650                 655

Arg Phe Gly Ala Leu Ser Arg Trp Leu Arg Gly Ser Gln Thr Ser Ser
            660                 665                 670

Gln Leu Ser Ala Met Glu Gln Gly Gln Arg Gln Arg Thr Pro Ser Thr
            675                 680                 685

Asn Asp Ala Leu Gln Pro Ala Gln Leu Glu Glu Ser Gln Ala Leu Gln
            690                 695                 700

Ser Val Lys Val Glu Ser Ile Lys His Thr Ser Gly Ser His Ser Ser
705                 710                 715                 720

Leu Leu Arg Ala Pro Lys Pro Met Thr Arg Ser Thr Ser Leu Pro Ile
            725                 730                 735

Asp Glu Gly Ile Ala Gly Ser Ile Ser Asp Glu Tyr Ala Gly Ser Ser
            740                 745                 750

Pro Pro Thr His Ser Ala Leu Lys Ser Ser Arg Arg Tyr Ala Lys Thr
            755                 760                 765

Leu Arg Leu Thr Ser Glu Gln Leu Lys Ser Leu Asn Leu Lys Lys Gly
            770                 775                 780

Ala Asn Thr Leu Thr Phe Ser Val Thr Ser Ser Tyr Gln Gly Lys Ala
785                 790                 795                 800

Val Cys Ser Ala Lys Leu Phe Leu Trp Asp His Asp Tyr Gln Val Val
            805                 810                 815

Ile Ser Asp Ile Asp Gly Thr Ile Thr Lys Ser Asp Ala Leu Gly His
            820                 825                 830

Ile Phe Thr Met Ala Gly Lys Asp Trp Thr His Ser Gly Val Ala Lys
            835                 840                 845

Leu Tyr Thr Asp Ile Val Asn Asn Gly Tyr His Ile Leu Tyr Leu Thr
            850                 855                 860

Ser Arg Ala Ile Gly Gln Ala Asp Tyr Thr Arg Lys Tyr Leu Lys Asn
865                 870                 875                 880

Val Glu Gln Asn Asn Tyr Gln Leu Pro Asp Gly Pro Val Ile Met Ser
            885                 890                 895

Pro Asp Arg Leu Met Thr Ala Phe His Arg Glu Val Ile Met Arg Lys
            900                 905                 910

Pro Glu Glu Phe Lys Met Ala Cys Leu Arg Asp Ile Arg Arg Leu Phe
            915                 920                 925

Gly Asp Arg Asn Pro Phe Tyr Ala Gly Phe Gly Asn Arg Ile Thr Asp
            930                 935                 940

Ala Leu Ser Tyr Arg Ser Val Asn Val Pro Ser Ser Arg Ile Phe Thr
945                 950                 955                 960

Ile Asp Ser Gly Gly Glu Val Lys Leu Glu Leu Leu Ser Ser Tyr Lys
            965                 970                 975

Ser Ser Tyr Leu Ala Leu Asn Asp Leu Val Asn Glu Ile Phe Pro Gly

Lys Arg Gln Ala Pro Glu Phe Asn Asp Trp Asn Phe Trp Arg Ala Pro
    980                 985                 990
                995                 1000                1005

Leu Pro Asp Ile Glu Leu Pro Val Ala Pro Ser His Gln Tyr Ala
    1010                1015                1020

Pro Thr Ala Val Pro Gly Glu Tyr Asn Ala Gln Gly Tyr Ser Ala
    1025                1030                1035

Gly Pro Gly Arg Leu Gly Val Ile Arg Ser Leu Thr Ser Ser Leu
    1040                1045                1050

Thr Ser Ala Gly Pro Leu Lys Thr Arg Thr Ala Ile Pro Ile Phe
    1055                1060                1065

Thr Ser Asn Ser Pro Pro Pro Asn Ser Tyr Pro Ser Ala Met
    1070                1075                1080

Lys Pro His Ala Pro His Gln Ser Gln Pro Ala Ser Ser Ser Pro
    1085                1090                1095

Gln Pro Pro Ala Ser Ala Pro Ser Gly Leu Gln Ile Ala Asp Arg
    1100                1105                1110

Thr Arg Arg Leu Ser Leu Ser Leu Met Arg Tyr Ser Ser His Ser
    1115                1120                1125

Ala Pro Thr Ser Ala Pro Val Leu Arg Thr Leu Thr Asp Ser Ser
    1130                1135                1140

Glu Pro Asn Val Gly Ile Asp Ser Gly Asp Ala Gly Ala Leu Ser
    1145                1150                1155

Glu Gly Asn Gln Ala Gly Leu Glu Pro Asn Arg Ser Pro His Leu
    1160                1165                1170

Gly Ser Asn Thr Asp Gly Val Phe Pro Leu Asp Val Pro Val Val
    1175                1180                1185

Lys Arg Lys Ala Ser Gly Phe Ser Val Ser Pro Pro Gln Leu Ala
    1190                1195                1200

Ser Arg Leu Ser Glu Thr Val Met Pro Phe Leu Arg Arg Arg Ala
    1205                1210                1215

Ser Lys Leu Glu Gln Gly Gln Glu Gln Gln Glu Gln Gln Gln
    1220                1225                1230

Glu Gln Glu Gln Glu Arg Glu His Asp Val Gln Leu Gly Ala Ala
    1235                1240                1245

Ala Glu Gly Glu Gln Leu Ala Tyr Thr Arg Glu Tyr Gly Glu Glu
    1250                1255                1260

Glu Ala Ala Ala Gly Tyr Leu Ala Glu Asp His Glu Leu Gly Glu
    1265                1270                1275

Asp Glu Glu Asp Glu Gly Glu Gly Ala Asp Gly Tyr Val Gly Tyr
    1280                1285                1290

Ser Gly Glu Glu Asp Glu Gly Leu Glu Glu Asp Gln Leu Glu Gly
    1295                1300                1305

Glu Glu Asp Glu Asp Glu Asp Asp Asp Val Glu Leu Asn Ile
    1310                1315                1320

Asp Ala Pro Phe Leu
    1325

<210> SEQ ID NO 3
<211> LENGTH: 3987
<212> TYPE: DNA
<213> ORGANISM: Mortierella alpina

<400> SEQUENCE: 3

```
atgcagtccg tgggaagctt cttctccact gtctcaaggt tctacaatga gctcaatcca      60
gccacgcttt cggcgccat tgacgtggtc gtggtcgagc aagccgatgg tgaattagca     120
tgctcaccat ttcatgtccg ctttggcaaa ctgagcattc tccgaccgca ggaaaaagtg     180
gtggaggtga ccgtcaacgg tcgcgtcgtt gattttccta tgaaggttgg cgatgcaggc     240
gaagccttct ttgtttttga gactgagcag gacgtgcccg aagagtttgc cacgtctcca     300
ctagcgggac ccaacacaga caaagttgag gaggacattg actatctgga tctagccgaa     360
gggcatagca ccgtgacata tccgcctgac gatatagtct tagatgcggg ctatgtcagc     420
gcccacagtg ggcatggatc agagtttgaa gaagacgaga gagcagactt gtcgcctgaa     480
tttgacaaaa agccagatta cgcatccgcg gtcaaatacg gcggtacaaa tggacaaggg     540
agacacctag gcagtgctaa tgaggcaaca acgtctgtac atgctttcat ggagcggcaa     600
gttcaacgat ggtcgcttac catgtcccta ccaccctctc cggtgttaaa gtctcgcgac     660
attatgaga actttcagcc tattgactcg gcgggccctt tcgataatag tcgagaggat     720
tctggacgcc tgctcgcgcc agagactatc gccgttagca atggaggcag cagtggatct     780
ctgtttcatc ctaaggaggg catgataatg gacatgactg gctacaagac cgaggactct     840
gacctgaatt ccgatgcgtc tgatgaacat gatgtaggca tggctggcgc tttgaatggt     900
cgccatcggc gcaaaagggc tgctcggcgg aaaaggagag ggccggtgca tggcgtcaac     960
tctcaagaca acctggccac tgaaactccc tcaattacag cgcatgtcct cagcagtctc    1020
gaccctcgct tgccgttgcg acctactgcg cgacctgctc tacgccccaa agctaacaac    1080
gggttgggca ctctaccgaa tcgccgttcg tcatcgatgc cgaatcttaa agatttcgta    1140
ggtgagaata acagtttgtc gccaagcgtg ccggcgataa tgcgacgctt ccttcgaag    1200
acgttaaact caaagttttc cgcaagaagc gacatcaaag atgggaccag ttcaagcagc    1260
tccgtagcct cctcgcctcc accgtcagtt gccaaccagc agagccctaa aaaccgccac    1320
catcaccatc atcaccacaa agagcacacc gaaggaagcc atccccgtcg ccactcgcac    1380
aaaccttcac agcaagtgca agtgaaaaaa ccccgccca gatccaatcc agctgttaat    1440
gcgctgagcg atacggagct cgagtatcaa acgccgcgaa caacagcagc tactcaagaa    1500
tcagagtggt cctggggatg gggcagctta ccggttaaaa atgacggtct aggcacaggg    1560
gaagcagatc acaaggagca tcactctagt catccatcaa tcgacattcc agccccacgg    1620
aaacctgtgt tgaacgagat ggagattgac gggactgtgt acagactcgc catcagcttg    1680
tgtccgggtg atgaattcgg aaaagatttg gaagccagcg aagcattgtt tgccaccaat    1740
caggtttcgt tcgatgagtt cgcgaaagac ccactcaaga ctctcaataa caagaatttg    1800
gtctgcctga tcaatgaccg gtattttact tggacagctg cgggaccata tctttcctca    1860
ctgatgctct tccggaagcc tctctctgac gaaacgctcc atcagctttc agccaaggac    1920
tcgcggcatc tatcagatcg actcgctgtg caagatgagc ccccaacccg tttcggcgct    1980
ctctccagat ggctaagggg atcacaaaacc tcgtcccaat tgagcgcgat ggagcaaggg    2040
caaagacaac gtactcccag taccaacgat gccttgcagc ctgctcagtt agaggagagt    2100
caagctttac agagcgtgaa agtcgaatcg attaagcaca cttccggatc acattcatca    2160
cttctacgcg ctcctaaacc aatgactcgt agcacctctc tgccgatcga cgaagggatc    2220
gccgggtcta tatcagacga gtacgctgga agctcgcctc cgacacattc tgcgctcaag    2280
agcagtagac ggtatgcgaa aacgcttcgc ttgcatctg aacagttgaa atcactaaat    2340
ttgaaaaaag gcgccaatac attgacgttt tcagtaacgt caagttatca aggcaaagca    2400
```

```
gtttgttccg ccaaattgtt tctgtgggac catgactacc aagtcgtcat atcggacatt    2460
gatggcacga ttacaaagtc ggacgctctc ggacacatct ttaccatggc aggaaaggat    2520
tggacccatt cgggtgtcgc caaactttac acggacatcg tcaacaatgg gtatcatatt    2580
ttgtacttga cctcaagggc cattggacag gcagactaca cacgaaagta cctcaagaac    2640
gtggagcaaa ataactacca gttaccggat ggaccggtga tcatgagccc tgatcgcttg    2700
atgaccgcct tccacaggga ggtgattatg aggaagccag aagaattcaa gatggcatgt    2760
ctgcgtgaca ttcggaggct gtttggagat cgcaacccct tctatgccgg gtttggaaac    2820
agaatcacgg acgcactgtc ctacaggagc gttaatgtcc cctcatctcg gatatttaca    2880
attgattcgg gaggtgaagt caagctggag ctcctcagca gctacaaatc atcatatctc    2940
gcgttgaacg atctcgtgaa tgagatcttt ccaggaaaaa gacaggcacc cgagttcaat    3000
gactggaact tttggcgggc gcccttgcca gatatcgagc ttccagttgc gccgtctcat    3060
caatacgccc ctacagcggt gccgggcgag tacaatgcac aaggatattc tgcaggtcct    3120
ggccggttgg gagtgatacg gagccttacc agttccctca cctcagcagg accgctcaag    3180
acgaggaccg ctatcccaat ttttacctca aattcgcccc ctcctccgaa ttcctaccca    3240
tcggcgatga agccccatgc accgcatcag tcccaaccag cctcctcctc gcctcaaccc    3300
cccgcatcag cgccgtcagg actgcagatc gctgatagga cccgtcgact ctcgctgtcg    3360
ttgatgcgat atagcagcca ttcagctccc acgtccgcgc cagttttgag aactttgacc    3420
gacagttccg agcccaatgt cggcattgac agcggtgatg caggcgctct ctctgagggg    3480
aatcaggcag gtttagagcc aaatcgctca cctcacttgg gatccaacac tgatggcgtt    3540
ttcccactgg acgttcctgt tgtgaagaga aaggcatctg gtttctcggt ctcaccgccc    3600
cagcttgcca gtcgactaag tgagactgta atgccttttc ttcgccgacg agcatccaag    3660
ttggagcagg ggcaggagca gcagcaggaa cagcagcagg aacaggaaca ggaacgagag    3720
catgatgtcc agctgggtgc agcagctgaa ggggagcagc ttgcttacac tcgagagtac    3780
ggggaagaag aagccgctgc tggatatctg gcggaggacc atgaactcgg agaggatgaa    3840
gaggatgaag gagaaggagc agatggatat gttggttatt ctggagaaga ggatgaaggt    3900
ctggaagaag atcagctcga gggtgaggaa gacgaggatg aggatgacga tgatgtagag    3960
ctcaacattg acgctccgtt cctatga                                        3987

<210> SEQ ID NO 4
<211> LENGTH: 4248
<212> TYPE: DNA
<213> ORGANISM: Mortierella alpina

<400> SEQUENCE: 4
atgcagtccg tgggaagctt cttctccact gtctcaaggt tctacaatga gctcaatcca      60
gccacgcttt cgggcgccat tgacgtggtc gtggtcgagc aagccgatgg tgaattagca     120
tgctcaccat ttcatgtccg cttttggcaaa ctgagcattc tccgaccgca ggaaaaagtg    180
gtggaggtga ccgtcaacgg tcgcgtcgtt gattttccta tgaaggttgg cgatgcaggc    240
gaagccttct ttgtttttga gactgagcag gacgtgcccg aagagtttgc cacgtctcca    300
ctagcgggac ccaacacaga caaagttgag gaggacattg actatctgga tctagccgaa    360
gggcatagca ccgtgacata tccgcctgac gatatagtct tagatgcggg ctatgtcagc    420
gcccacagtg gcatggatc agagtttgaa gaagacgaga gagcagactt gtcgcctgaa    480
```

```
tttgacaaaa agccagatta cgcatccgcg gtcaaatacg gcggtacaaa tggacaaggg     540
agacacctag gcagtgctaa tgaggcaaca acgtctgtac atgctttcat ggagcggcaa     600
gttcaacgat ggtcgcttac catgtcccta ccaccctctc cggtgttaaa gtctcgcgac     660
attatggaga actttcagcc tattgactcg gcgggcccctt tcgataatag tcgagaggat    720
tctggacgcc tgctcgcgcc agagactatc gccgttagca atggaggcag cagtggatct    780
ctgtttcatc ctaaggaggg catgataatg gacatgactg ctacaagac cgaggactct     840 gacctgaatt ccgatgcgtc tgatgaacat gatgtaggca tggctggcgc tttgaatggt    900
cgccatcggc gcaaaagggc tgctcggcgg aaaaggagag ggccggtgca tggcgtcaac    960
tctcaagaca acctggccac tgaaactccc tcaattacag cgcatgtcct cagcagtctc   1020
gaccctcgct tgccgttgcg acctactgcg cgacctgctc tacgcccaa agctaacaac    1080 gggttgggca ctctaccgaa tcgccgttcg tcatcgatgc cgaatcttaa agatttcgta   1140
ggtgagaata acagtttgtc gccaagcgtg ccggcgataa tgcgacgctt tccttcgaag   1200
acgttaaact caaagttttc cgcaagaagc gacatcaaag atgggaccag ttcaagcagc   1260
tccgtagcct cctcgcctcc accgtcagtt gccaaccagc agagccctaa aaaccgccac   1320
catcaccatc atcaccacaa agagcacacc gaaggaagcc atccccgtcg ccactcgcac   1380
aaaccttcac agcaagtgca agtgaaaaaa ccccgccca gatccaatcc agctgttaat    1440
gcgctgagcg atacggagct cgagtatcaa acgccgcgaa caacagcagc tactcaagaa   1500
tcagagtggt cctggggatg gggcagctta ccggttaaaa atgacggtct aggcacaggg   1560
gaagcagatc acaaggagca tcactctagt catccatcaa tcgacattcc agccccacgg   1620
aaacctgtgt tgaacgagat ggagattgac gggactgtgt acagactcgc catcagcttg   1680
tgtccgggtg atgaattcgg aaaagatttg gaagccagcg aagcattgtt tgccaccaat   1740
caggtttcgt tcgatgagtt cgcgaaagac ccactcaaga ctctcaataa caagaatttg   1800
gtctgcctga tcaatgaccg gtattttact tggacagctg cgggaccata tctttcctca   1860
ctgatgctct tccggaagcc tctctctgac gaaacgctcc atcagctttc agccaaggac   1920
tcgcggcatc tatcagatcg actcgctgtg caagatgagc ccccaacccg tttcggcgct   1980
ctctccagat ggctaagggg atcacaaaacc tcgtcccaat tgagcgcgat ggagcaaggg   2040
caaagacaac gtactcccag taccaacgat gccttgcagc ctgctcagtt agaggagagt   2100
caagctttac agagcgtgaa agtcgaatcg attaagcaca cttccggatc acattcatca   2160
cttctacgcg ctcctaaacc aatgactcgt agcacctctc tgccgatcga cgaagggatc   2220
gccgggtcta tatcagacga gtacgctgga agctcgcctc cgacacattc tgcgctcaag   2280
agcagtagac ggtatgcgaa aacgcttcgc ttgacatctg aacagttgaa atcactaaat   2340
ttgaaaaaag gcgccaatac attgacgttt tcagtaacgt caagttatca aggcaaagca   2400
gtttgttccg ccaaattgtt tctgtgggac catgactacc aagtcgtcat atcggacatt   2460
gatggcacga ttacaaagtc ggacgctctc ggacacatct ttaccatggc aggaaaggat   2520 tggaccccatt cgggtgtcgc caaactttac acggacatcg tcaacaatgg gtatcatatt   2580
ttgtacttga cctcaagggc cattggacag gcagactaca cacgaaagta cctcaagaac   2640
gtggagcaaa ataactacca gttaccggat ggaccggtga tcatgagccc tgatcgcttg   2700
atgaccgcct tccacaggga ggtgattatg aggaagccag aagaattcaa gatggcatgt   2760
ctgcgtgaca ttcggaggct gtttggagat cgcaaccccct tctatgccgg gtttggaaac   2820
agaatcacgg acgcactgtc ctacaggagc gttaatgtcc cctcatctcg gatatttaca   2880
```

-continued

| | |
|---|---|
| attgattcgg gaggtgaagt caagctggag ctcctcagca gctacaaatc atcatatctc | 2940 |
| gcgttgaacg atctcgtgaa tgagatcttt ccaggaaaaa gacaggcacc cgagttcaat | 3000 |
| gactggaact tttggcgggc gcccttgcca gatatcgagc ttccagttgc gccgtctcat | 3060 |
| caatacgccc ctacagcggt gccgggcgag tacaatgcac aaggatattc tgcaggtcct | 3120 |
| ggccggttgg gagtgatacg gagccttacc agttccctca cctcagcagg accgctcaag | 3180 |
| acgaggaccg ctatcccaat ttttacctca aattcgcccc ctcctccgaa ttcctaccca | 3240 |
| tcggcgatga agcccatgc accgcatcag tcccaaccag cctcctcctc gcctcaaccc | 3300 |
| cccgcatcag cgccgtcagg actgcagatc gctgatagga cccgtcgact ctcgctgtcg | 3360 |
| ttgatgcgat atagcagcca ttcagctccc acgtccgcgc cagttttgag aactttgacc | 3420 |
| gacagttccg agcccaatgt cggcattgac agcggtgatg caggcgctct ctctgagggg | 3480 |
| aatcaggcag gtttagagcc aaatcgctca cctcacttgg gatccaacac tgatggcgtt | 3540 |
| ttcccactgg acgttcctgt tgtgaagaga aaggcatctg gtttctcggt ctcaccgccc | 3600 |
| cagcttgcca gtcgactaag tgagactgta atgccttttc ttcgccgacg agcatccaag | 3660 |
| ttggagcagg ggcaggagca gcagcaggaa cagcagcagg aacaggaaca ggaacgagag | 3720 |
| catgatgtcc agctgggtgc agcagctgaa ggggagcagc ttgcttacac tcgagagtac | 3780 |
| ggggaagaag aagccgctgc tggatatctg gcggaggacc atgaactcgg agaggatgaa | 3840 |
| gaggatgaag gagaaggagc agatggatat gttggttatt ctggagaaga ggatgaaggt | 3900 |
| ctggaagaag atcagctcga gggtgaggaa gacgaggatg aggatgacga tgatgtagag | 3960 |
| ctcaacattg acgctccgtt cctatgaaca tccttgtaca tcaatgcgac agatcacagg | 4020 |
| ggttgcaagt cgtctgatgc tatgagcctt ccaagttttt ggctggataa atgggtgttg | 4080 |
| ttgaggattt attgttgtta caaggcgatg ccgattcaaa aatgtggata ccgcactgg | 4140 |
| tgcaagaggt gggaaatggc aaagaggacg agcaagaaag aagaaggaga aaaaagaca | 4200 |
| taaactacca acgagaaaag tctataacag aaaaaaaaaa aaaaaaaa | 4248 |

<210> SEQ ID NO 5
<211> LENGTH: 5034
<212> TYPE: DNA
<213> ORGANISM: Mortierella alpina

<400> SEQUENCE: 5

| | |
|---|---|
| atgcagtccg tgggaagctt cttctccact gtctcaaggt tctacaatga gctcaatcca | 60 |
| gccacgcttt cgggcgccat tgacgtggtc gtggtcgagc aagccgatgg tgaattagca | 120 |
| tgctcaccat ttcatgtccg ctttggcaaa ctgagcattc tccgaccgca ggaaaaagtg | 180 |
| gtaagctttg cctgtcctca cctccaagca tatcggtacc cgagacgacc cttgctattg | 240 |
| cccccctcttc aaaaccttgc cgactgaaat gcgtttcctg gtctaaagtg actccgtcgc | 300 |
| gcatgtccgc tccacatcaa taagctctga tacatggtca aaataactcc tcgacggcct | 360 |
| tcttaggtg gaggtgaccg tcaacggtcg cgtcgttgat tttcctatga aggttggcga | 420 |
| tgcaggcgaa gccttctttg tttttgagac tgagcaggac gtgcccgaag agtttgccac | 480 |
| gtctccacta gcgggaccca acacagacaa agttgaggag acattgact atctggatct | 540 |
| agccgaaggg catagcaccg tgacatatcc gcctgacgat ataggtaaat cacgacgttg | 600 |
| tatcatgctg ctgagacatg cggaacgcgg cggaatcccg tccctcgcaa ggttgtcgct | 660 |
| acttacataa tactacgcgc catccacagt cttagatgcg ggctatgtca gcgcccacag | 720 |

```
tgggcatgga tcagagtttg aagaagacga gagagcagac ttgtcgcctg aatttgacaa    780
aaagccagat tacgcatccg cggtcaaata cggcggtaca aatggacaag ggagacacct    840
aggcagtgct aatgaggcaa caacgtctgt acatgctttc atggagcggc aagttcaacg    900
atggtcgctt accatgtccc taccaccctc tccggtgtta aagtctcgcg acattatgga    960
gaactttcag cctattgact cggcgggccc tttcgataat agtcgagagg attctggacg   1020
cctgctcgcg ccagagacta tcgccgttag caatggaggc agcagtggat ctctgtttca   1080
tcctaaggag ggcatgataa tggacatgac tggctacaag accgaggact ctgacctgaa   1140
ttccgatgcg tctgatgaac atgatgtagg catggctggc gctttgaatg gtcgccatcg   1200
gcgcaaaagg gctgctcggc ggaaaaggag agggccggtg catggcgtca actctcaaga   1260
caacctggcc actgaaactc cctcaattac agccatgtc ctcagcagtc tcgaccctcg   1320
cttgccgttg cgacctactg cgcgacctgc tctacgcccc aaagctaaca acgggttggg   1380
cactctaccg aatcgccgtt cgtcatcgat gccgaatctt aaagatttcg taggtaagag   1440
gtccacaatg gactgtcaaa caacaaggtg ggtaatgatg agcaagtcca ggcagtaggc   1500
tgactcgagg caacccataa cgtcgcgtta taggtgagaa taacagtttg tcgccaagcg   1560
tgccggcgat aatgcgacgc tttccttcga agacgttaaa ctcaaagttt ccgcaagaa    1620
gcgacatcaa agatgggacc agttcaagca gctccgtagc ctcctcgcct ccaccgtcag   1680
ttgccaacca gcagagccct aaaaaccgcc accatcacca tcatcaccac aaagagcaca   1740
ccgaaggaag ccatccccgt cgccactcgc acaaaccttc acagcaagtg caagtgaaaa   1800
aaccccgcc cagatccaat ccagctgtta atgcgctgag cgatacggag ctcgaggtta    1860
gtgtcccatt catcaatagt tcgttcttaa agtgacaatg cccatatctc atgcctgtca   1920
gtaccgtctt catgattgag aatagtatca acgccgcga acaacagcag ctactcaaga   1980
atcagagtgg tcctggggat ggggcagctt accggttaaa aatgacggtc taggcacagg   2040
ggaagcagat cacaaggagc atcactctag tcatccatca atcgacattc cagccccacg   2100
gaaacctgtg ttgaacgaga tggagattga cgggactgtg tacagactcg ccatcagctt   2160
gtgtccgggt gatgaattcg gaaaagattt ggtacgtctg cttgaagtaa cgaaataatg   2220
gttacggcca tggaacaaaa tatgaaacag caagccgcta acctgttcta ctttggtgag   2280
gggtccgcag gaagccagcg aagcattgtt tgccaccaat caggtttcgt tcgatgagtt   2340
cgcgaaagac ccactcaaga ctctcaataa caagaatttg gtctgcctga tcaatgaccg   2400
gtacagaagt ctactggcat tcatgcatgg gactcaaagg cgtgcatccc attaagcgac   2460
tgtgtcaatt gatttgtttc cgctaggtat tttacttgga cagctgcggg accatatctt   2520
tcctcactga tgctcttccg gaagcctctc tctgacgaaa cgctccatca gctttcagcc   2580
aaggactcgc ggcatctatc agatcgactc gctgtgcaag atgagccccc aacccgtttc   2640
ggcgctctct ccagatggct aaggggatca caaacctcgt cccaattgag cgcgatggag   2700
caagggcaaa gacaacgtac tcccagtacc aacgatgcct tgcagcctgc tcagttagag   2760
gaggtacatg aaatcctctt ttattcaaaa agccccgaga tgcaatagta caaccagtta   2820
ctgacaacac ctcggtatcg ctgtagagtc aagctttaca gagcgtgaaa gtcgaatcga   2880
ttaagcacac ttccggatca cattcatcac ttctacgcgc tcctaaacca atgactcgta   2940
gcacctctct gccgatcgac gaagggatcg ccgggtctat atcagacgag tacgctggaa   3000
gctcgcctcc gacacattct gcgctcaaga gcagtagacg gtatgcgaaa acgcttcgct   3060
tgacatctga acagttggta cgtgcctaca accggatagc gtattgaatt gcgcgtgtac   3120
```

```
cagcagcatt gaaatctcac acggcattgt ccgcttctga aatagaaatc actaaatttg    3180
aaaaaaggcg ccaatacatt gacgttttca gtaacgtcaa gttatcaagg caaagcagtt    3240
tgttccgcca aattgtttct gtgggaccat gactaccaag tcgtcatatc ggacattgat    3300
ggcacgatta caaagtcgga cgctctcgga cacatcttta ccatggcagg aaaggattgg    3360
acccattcgg gtgtcgccaa actttacacg gacatcgtca acaatgggta tcatattttg    3420
tacttgacct caagggccat ggacaggca gactacacac gaaagtacct caagaacgtg     3480
gagcaaaata actaccagtt accggatgga ccggtgatca tgagccctga tcgcttgatg    3540
accgccttcc acaggtcagc agtgttcact gtggcgcata ggcttcgtag ggatgggaca    3600
tcttgctttg aatgcttact aacaaccatt tgcgttaacg ttttagggag gtgattatga    3660
ggaagccaga agaattcaag atggcatgtc tgcgtgacat tcggaggctg tttgagatc     3720 gcaaccccett ctatgccggg tttggaaaca gaatcacgga cgcactgtcc tacaggagcg    3780
ttaatgtccc ctcatctcgg atatttacaa ttgattcggg aggtgaagtc aagctggagc    3840
tcctcagcag ctacaaatca tcgtgagtac ccttcactgc acttgctttt ccactggtgg    3900
cgtccatcca gtctttgttg gcgaaacatg gatttaggac ctgaccattt ttgtctcttt    3960
gctgatctac ttgacacaag atatctcgcg ttgaacgatc tcgtgaatga gatctttcca    4020
ggaaaaagac aggcacccga gttcaatgac tggaactttt ggcgggcgcc cttgccagat    4080
atcgagcttc cagttgcgcc gtctcatcaa tacgcccta cagcggtgcc gggcgagtac     4140
aatgcacaag gatattctgc aggtcctggc cggttgggag tgatacggag ccttaccagt    4200
tccctcacct cagcaggacc gctcaagacg aggaccgcta tcccaattt tacctcaaat     4260 tcgccccctc ctccgaattc ctacccatcg gcgatgaagc cccatgcacc gcatcagtcc    4320
caaccagcct cctcctcgcc tcaaccccc gcatcagcgc cgtcaggact gcagatcgct     4380
gataggaccc gtcgactctc gctgtcgttg atgcgatata gcagccattc agctcccacg    4440
tccgcgccag ttttgagaac tttgaccgac agttccgagc ccaatgtcgg cattgacagc    4500
ggtgatgcag cgctctctc tgaggggaat caggcaggtt tagagccaaa tcgctcacct    4560
cacttgggat ccaacactga tggcgttttc ccactgacg ttcctgttgt gaagagaaag     4620
gcatctggtt tctcggtctc accgccccag cttgccagtc gactaagtga gactgtaatg    4680
ccttttcttc gccgacgagc atccaagttg gagcaggggc aggagcagca gcaggaacag    4740
cagcaggaac aggaacagga acgagagcat gatgtccagc tgggtgcagc agctgaaggg    4800
gagcagcttg cttacactcg agagtacggg gaagaagaag ccgctgctgg atatctggcg    4860
gaggaccatg aactcggaga ggatgaagag gatgaaggag aaggagcaga tggatatgtt    4920
ggttattctg gagaagagga tgaaggtctg gaagaagatc agctcgaggg tgaggaagac    4980
gaggatgagg atgacgatga tgtagagctc aacattgacg ctccgttcct atga          5034
```

<210> SEQ ID NO 6
<211> LENGTH: 3717
<212> TYPE: DNA
<213> ORGANISM: Mortierella alpina
<220> FEATURE:
<221> NAME/KEY: CDS
<222> LOCATION: (1)..(3717)
<223> OTHER INFORMATION:

<400> SEQUENCE: 6

```
atg tat tct gtc ggg aac ttc ttc tcg acc gtt acg aaa ttc tac aat    48
Met Tyr Ser Val Gly Asn Phe Phe Ser Thr Val Thr Lys Phe Tyr Asn
```

```
1               5                   10                  15
gag atc aac ccc gcc acc ctc tcc ggc gca atc gac atc atc gtc gtc        96
Glu Ile Asn Pro Ala Thr Leu Ser Gly Ala Ile Asp Ile Ile Val Val
             20                  25                  30 cag cag gcc aac ggc gac ctt gca tgc tct ccc ttc cac gtg cgt ttc       144
Gln Gln Ala Asn Gly Asp Leu Ala Cys Ser Pro Phe His Val Arg Phe
             35                  40                  45 ggc aaa ctc agc gtc ctc cgg ccg cag gag aag gtc gtc gag gtt cgg       192
Gly Lys Leu Ser Val Leu Arg Pro Gln Glu Lys Val Val Glu Val Arg
 50                  55                  60 gtc aat ggc gaa gtc atc gcc ttc ccc atg aag gtc ggc gac gca gga       240
Val Asn Gly Glu Val Ile Ala Phe Pro Met Lys Val Gly Asp Ala Gly
 65                  70                  75                  80 gag gcc ttc ttt gtg ctc gag acc gac gac tat gtg ccg gat gag ttt       288
Glu Ala Phe Phe Val Leu Glu Thr Asp Asp Tyr Val Pro Asp Glu Phe
                 85                  90                  95 gcc aca tcg cct atc gct ggt ccg agt gac gaa gcc gac ctc gcc cct       336
Ala Thr Ser Pro Ile Ala Gly Pro Ser Asp Glu Ala Asp Leu Ala Pro
                100                 105                 110 gtt gac tac ttt gac ctg aac ggc cat ccc cac ggg tct cag gac cag       384
Val Asp Tyr Phe Asp Leu Asn Gly His Pro His Gly Ser Gln Asp Gln
            115                 120                 125 aaa cgg agg cag cat cag cag caa cag gtg ctg gag ggc atg agc gga       432
Lys Arg Arg Gln His Gln Gln Gln Gln Val Leu Glu Gly Met Ser Gly
130                 135                 140 cag tat cct caa gga aca gaa gac gat gct cct ctt gac aac ggc tat       480
Gln Tyr Pro Gln Gly Thr Glu Asp Asp Ala Pro Leu Asp Asn Gly Tyr
145                 150                 155                 160 gtg agc gct gct agt ggc cat ggc tct gct ttt gaa gag agc ttg aag       528
Val Ser Ala Ala Ser Gly His Gly Ser Ala Phe Glu Glu Ser Leu Lys
                165                 170                 175 gac gac agc gat cac gag tcg gtc ttc tcg gcc aca tcc cca gga tca       576
Asp Asp Ser Asp His Glu Ser Val Phe Ser Ala Thr Ser Pro Gly Ser
                180                 185                 190 gca gaa cgg atc gcc gcc gat tct aat act aag gac aca gca ctc gac       624
Ala Glu Arg Ile Ala Ala Asp Ser Asn Thr Lys Asp Thr Ala Leu Asp
            195                 200                 205 ttg cct gga tcc ttt ggc cca acg gta gtg act aat acc atc aaa aac       672
Leu Pro Gly Ser Phe Gly Pro Thr Val Val Thr Asn Thr Ile Lys Asn
210                 215                 220 aag gac agc atc aac ttt cca gtt gat gcc atc ttt cct aca gtt gca       720
Lys Asp Ser Ile Asn Phe Pro Val Asp Ala Ile Phe Pro Thr Val Ala
225                 230                 235                 240 cac gag gaa cag gac atg gct ctg atc aaa gat caa cag ggc tct cga       768
His Glu Glu Gln Asp Met Ala Leu Ile Lys Asp Gln Gln Gly Ser Arg
                245                 250                 255 tcc agc cgt cgc aga agt gag gtc cta ttc gat atg aca gga tac aag       816
Ser Ser Arg Arg Arg Ser Glu Val Leu Phe Asp Met Thr Gly Tyr Lys
                260                 265                 270 acc gac tca tgc tcg gac tcg tcg gat gat gag gat ggc ttg cct cgt       864
Thr Asp Ser Cys Ser Asp Ser Ser Asp Asp Glu Asp Gly Leu Pro Arg
            275                 280                 285 ggc att cta tcg gat agt gag cgt cac ggt cgt agc acg cgt aag aag       912
Gly Ile Leu Ser Asp Ser Glu Arg His Gly Arg Ser Thr Arg Lys Lys
            290                 295                 300 ttc agg agg agc aag tcg cac ctt tca atg gag cag agg cac caa ttg       960
Phe Arg Arg Ser Lys Ser His Leu Ser Met Glu Gln Arg His Gln Leu
305                 310                 315                 320 ctg gag gac att aaa caa gga gcg ttc ctg aag ccc gag gaa agc ctt      1008
```

```
                Leu Glu Asp Ile Lys Gln Gly Ala Phe Leu Lys Pro Glu Glu Ser Leu
                                325                 330                 335 gca aac aca cag att gaa cgt caa aca tcc cgg gca agt agg aaa aca          1056
Ala Asn Thr Gln Ile Glu Arg Gln Thr Ser Arg Ala Ser Arg Lys Thr
                340                 345                 350 aag agg gca agc att cca agt gca tgg caa gga cga agg aac agg aag          1104
Lys Arg Ala Ser Ile Pro Ser Ala Trp Gln Gly Arg Arg Asn Arg Lys
            355                 360                 365 aga gcc aac agc atg cct gct atc ggt gaa cca gac ttg gca ttt cct          1152
Arg Ala Asn Ser Met Pro Ala Ile Gly Glu Pro Asp Leu Ala Phe Pro
        370                 375                 380 gcc tat gtg gct cgc cga cct aac cat cgt cgc gat gct caa gca aac          1200
Ala Tyr Val Ala Arg Arg Pro Asn His Arg Arg Asp Ala Gln Ala Asn
385                 390                 395                 400 cag acg gat gtt gca atg gac gac aag ccc aag ccc aag cgc act gct          1248
Gln Thr Asp Val Ala Met Asp Asp Lys Pro Lys Pro Lys Arg Thr Ala
                405                 410                 415 cgg ccc agc gtt atg agc gat acg gag atg gag tat gaa tcc aac aat          1296
Arg Pro Ser Val Met Ser Asp Thr Glu Met Glu Tyr Glu Ser Asn Asn
            420                 425                 430 gtc cct gca tct acc cag ggt aaa gag tgg acc tgg gga tgg gga acg          1344
Val Pro Ala Ser Thr Gln Gly Lys Glu Trp Thr Trp Gly Trp Gly Thr
        435                 440                 445 ctg cct gtc aaa cag gat aac cct gat gaa gag gat gag atc aag gaa          1392
Leu Pro Val Lys Gln Asp Asn Pro Asp Glu Glu Asp Glu Ile Lys Glu
    450                 455                 460 caa att acg gaa gaa aag gcg ccc gaa gtt cct gtg gag att gag gca          1440
Gln Ile Thr Glu Glu Lys Ala Pro Glu Val Pro Val Glu Ile Glu Ala
465                 470                 475                 480 aag gag ttt cag atg gga tca aca aaa tgc cgc gta gcg ctc agt ctc          1488
Lys Glu Phe Gln Met Gly Ser Thr Lys Cys Arg Val Ala Leu Ser Leu
                485                 490                 495 tgc gga gag gat gac ttt gga aag gac att gtt gct agc cac aag gct          1536
Cys Gly Glu Asp Asp Phe Gly Lys Asp Ile Val Ala Ser His Lys Ala
            500                 505                 510 ttt caa aga gcc cag ttg acc ttt gag gca ttc tcc aaa gat ccc gcg          1584
Phe Gln Arg Ala Gln Leu Thr Phe Glu Ala Phe Ser Lys Asp Pro Ala
        515                 520                 525 gca att ctg gcc gac aag aga ctt gtg tgt tac atg gat ggg cgg ttt          1632
Ala Ile Leu Ala Asp Lys Arg Leu Val Cys Tyr Met Asp Gly Arg Phe
    530                 535                 540 tat tcg tgg agt aat gcc gtt cct cag ctc gca gcc ctt ctc ttc ttc          1680
Tyr Ser Trp Ser Asn Ala Val Pro Gln Leu Ala Ala Leu Leu Phe Phe
545                 550                 555                 560 cac cag cct ctt tca gac gcg gcc tct gct ctc gac ctc aag gac caa          1728
His Gln Pro Leu Ser Asp Ala Ala Ser Ala Leu Asp Leu Lys Asp Gln
                565                 570                 575 aag gca cat gcg gcc gag gac aga ccg agc gcc acg cgt ttt ggc aca          1776
Lys Ala His Ala Ala Glu Asp Arg Pro Ser Ala Thr Arg Phe Gly Thr
            580                 585                 590 atc tcc aga tgg ttc agg aag gcg cct gca ggc agc gcg tcc ccc tct          1824
Ile Ser Arg Trp Phe Arg Lys Ala Pro Ala Gly Ser Ala Ser Pro Ser
        595                 600                 605 att gca gat atg gcc tca gca tcc tcg aca acc ctt gca ggt ggt gag          1872
Ile Ala Asp Met Ala Ser Ala Ser Ser Thr Thr Leu Ala Gly Gly Glu
    610                 615                 620 acc gcc gct gtc gct gtg gga tca gat gac gac gag ccc ttg cac aac          1920
Thr Ala Ala Val Ala Val Gly Ser Asp Asp Asp Glu Pro Leu His Asn
625                 630                 635                 640
```

-continued

| | | |
|---|---|---|
| aag gcc ctg cgt agc aaa tcc ctg ccc cca ctg gag act ggc cgg acc<br>Lys Ala Leu Arg Ser Lys Ser Leu Pro Pro Leu Glu Thr Gly Arg Thr<br>645 650 655 | 1968 | |
| gac gac cac agt cag agc cat gtc gct gta cct gcg ctt tcg gag aaa<br>Asp Asp His Ser Gln Ser His Val Ala Val Pro Ala Leu Ser Glu Lys<br>660 665 670 | 2016 | |
| gca gcg gac ggt gtc cca gat cag aag cgc tat gcc aag acg ctg cgg<br>Ala Ala Asp Gly Val Pro Asp Gln Lys Arg Tyr Ala Lys Thr Leu Arg<br>675 680 685 | 2064 | |
| ctc acc tcg gaa cag ctt caa tcc ttg ggt ttg aaa aag ggc gcc aac<br>Leu Thr Ser Glu Gln Leu Gln Ser Leu Gly Leu Lys Lys Gly Ala Asn<br>690 695 700 | 2112 | |
| acg gtc tcg ttc tca gtg aca tcg tcc tac cag gga act gca act tgt<br>Thr Val Ser Phe Ser Val Thr Ser Ser Tyr Gln Gly Thr Ala Thr Cys<br>705 710 715 720 | 2160 | |
| gta gcc aag atc ttt ttg tgg gat tac gac tcc cag gtg gtg atc tcg<br>Val Ala Lys Ile Phe Leu Trp Asp Tyr Asp Ser Gln Val Val Ile Ser<br>725 730 735 | 2208 | |
| gat att gat ggt aca atc aca aag tca gat gcc ctc ggc cac att ttt<br>Asp Ile Asp Gly Thr Ile Thr Lys Ser Asp Ala Leu Gly His Ile Phe<br>740 745 750 | 2256 | |
| gcc atg gcc ggt cgc gac tgg acg cat ctc ggt gtc gcc aag ctg ttc<br>Ala Met Ala Gly Arg Asp Trp Thr His Leu Gly Val Ala Lys Leu Phe<br>755 760 765 | 2304 | |
| aca gat att cgc agc aac gga tat cac atc ctg tac ctg acc tcc cga<br>Thr Asp Ile Arg Ser Asn Gly Tyr His Ile Leu Tyr Leu Thr Ser Arg<br>770 775 780 | 2352 | |
| gcc att ggc cag gca gac tac aca cgc aag tat ctt cag aag gtc gag<br>Ala Ile Gly Gln Ala Asp Tyr Thr Arg Lys Tyr Leu Gln Lys Val Glu<br>785 790 795 800 | 2400 | |
| caa aac agt tac cag ctc ccg gat ggc cct gtc atc atg agt cca gac<br>Gln Asn Ser Tyr Gln Leu Pro Asp Gly Pro Val Ile Met Ser Pro Asp<br>805 810 815 | 2448 | |
| cgt ctg ttc tct gcc ttc cat cgt gag gtg att atc cgg aaa cca gag<br>Arg Leu Phe Ser Ala Phe His Arg Glu Val Ile Ile Arg Lys Pro Glu<br>820 825 830 | 2496 | |
| gtg ttc aag atg gcg tgt ctg cgt gat gtg aag aag ctg ttt ggg gac<br>Val Phe Lys Met Ala Cys Leu Arg Asp Val Lys Lys Leu Phe Gly Asp<br>835 840 845 | 2544 | |
| agg aac ccg ttc tat gct gga ttt gga aac cgg atc acg gac gcc ctc<br>Arg Asn Pro Phe Tyr Ala Gly Phe Gly Asn Arg Ile Thr Asp Ala Leu<br>850 855 860 | 2592 | |
| tcc tac cgc agt gtc aac gtt cca ccc tcc cga atc ttc acc att gac<br>Ser Tyr Arg Ser Val Asn Val Pro Pro Ser Arg Ile Phe Thr Ile Asp<br>865 870 875 880 | 2640 | |
| tct tat ggt gag gtg aag ttg gag ctg ctc agt gct ttc aag tct tca<br>Ser Tyr Gly Glu Val Lys Leu Glu Leu Leu Ser Ala Phe Lys Ser Ser<br>885 890 895 | 2688 | |
| tac ttg gct ttg aat gac ctc gtc aat gag atc ttc cca gga caa cga<br>Tyr Leu Ala Leu Asn Asp Leu Val Asn Glu Ile Phe Pro Gly Gln Arg<br>900 905 910 | 2736 | |
| gtt gca ccc gag ttc aac gac tgg aac ttt tgg aaa tcg gat tta cca<br>Val Ala Pro Glu Phe Asn Asp Trp Asn Phe Trp Lys Ser Asp Leu Pro<br>915 920 925 | 2784 | |
| cgg att gat ctc cct gat ctc ccc atc ccc aac aat aat tat aca tca<br>Arg Ile Asp Leu Pro Asp Leu Pro Ile Pro Asn Asn Asn Tyr Thr Ser<br>930 935 940 | 2832 | |
| gga tct tcg aca tcg ctc ctc tca tcc acc act agc gtg gcc aag aag<br>Gly Ser Ser Thr Ser Leu Leu Ser Ser Thr Thr Ser Val Ala Lys Lys<br>945 950 955 960 | 2880 | |

```
gtg gcg tct ttg acc agc tct tca tcg agc tcg aac ctt ctc cag cca      2928
Val Ala Ser Leu Thr Ser Ser Ser Ser Ser Asn Leu Leu Gln Pro
                965                 970                 975 acg tcg ccc act agc cct acg gga gat ttc aag aac aag cgc ctg tct      2976
Thr Ser Pro Thr Ser Pro Thr Gly Asp Phe Lys Asn Lys Arg Leu Ser
            980                 985                 990 aat gac aga aac acg tat gcg ggc gtc ctt tca gga cgt cag gac aca      3024
Asn Asp Arg Asn Thr Tyr Ala Gly Val Leu Ser Gly Arg Gln Asp Thr
        995                 1000                1005 tgg acc agc gat gat gaa tat cag gat caa cag cag cga ctg atc          3069
Trp Thr Ser Asp Asp Glu Tyr Gln Asp Gln Gln Gln Arg Leu Ile
    1010                1015                1020 gcg ggt gac tct gcg ccg tca acg cca gga tca gag ttg aag gca          3114
Ala Gly Asp Ser Ala Pro Ser Thr Pro Gly Ser Glu Leu Lys Ala
1025                1030                1035 gga cag gag ctg aag gag gat gca agg aag gca cga tct ggc tcg          3159
Gly Gln Glu Leu Lys Glu Asp Ala Arg Lys Ala Arg Ser Gly Ser
1040                1045                1050 cca tcg atg ctc tct gct ctt gtt cca tcg cgg tta atc cgc gca          3204
Pro Ser Met Leu Ser Ala Leu Val Pro Ser Arg Leu Ile Arg Ala
1055                1060                1065 gtg agg agt ggc agc atc agc agt cag acc aac cct gtg ccc tcg          3249
Val Arg Ser Gly Ser Ile Ser Ser Gln Thr Asn Pro Val Pro Ser
1070                1075                1080 tcg atg cgg agt tcg gtt aca ccg cat tcg ccc gag atg aaa ggg          3294
Ser Met Arg Ser Ser Val Thr Pro His Ser Pro Glu Met Lys Gly
1085                1090                1095 atc atc ggg tcg ctg ccg tca cca gtg tct tcg ttt gag agc ggt          3339
Ile Ile Gly Ser Leu Pro Ser Pro Val Ser Ser Phe Glu Ser Gly
1100                1105                1110 gcg gat gtg gtg cgt cgg atg tcc att ccc tcg cct cca ccg ttg          3384
Ala Asp Val Val Arg Arg Met Ser Ile Pro Ser Pro Pro Pro Leu
1115                1120                1125 gag ggg ctg ctc cag acg gat gag gag gtg gct cag gca tcg agc          3429
Glu Gly Leu Leu Gln Thr Asp Glu Glu Val Ala Gln Ala Ser Ser
1130                1135                1140 aag gcg ctg gcg ctt cag gga tcg gac aca gca gat ttg agc aga          3474
Lys Ala Leu Ala Leu Gln Gly Ser Asp Thr Ala Asp Leu Ser Arg
1145                1150                1155 gag agc agt gtt cag gcc aag agt gat gtg atg gac gac ctt gtg          3519
Glu Ser Ser Val Gln Ala Lys Ser Asp Val Met Asp Asp Leu Val
1160                1165                1170 gcg gtc aag gag gaa gag gag gac gag acc gat cag cag cgg ttg          3564
Ala Val Lys Glu Glu Glu Glu Asp Glu Thr Asp Gln Gln Arg Leu
1175                1180                1185 ctg gat gca gcg tat gtg gat gag tat gtg gat gag gag gat gag          3609
Leu Asp Ala Ala Tyr Val Asp Glu Tyr Val Asp Glu Glu Asp Glu
1190                1195                1200 gag gga tat gat gga tat gac gag cag ggt gag gat gag atg gac          3654
Glu Gly Tyr Asp Gly Tyr Asp Glu Gln Gly Glu Asp Glu Met Asp
1205                1210                1215 gag gag gat gag gag gac gag tat ctg gat gag att gag gag act          3699
Glu Glu Asp Glu Glu Asp Glu Tyr Leu Asp Glu Ile Glu Glu Thr
1220                1225                1230 ctg gag gag ccg ttc ctg                                              3717
Leu Glu Glu Pro Phe Leu
1235
```

<210> SEQ ID NO 7

<211> LENGTH: 1239
<212> TYPE: PRT
<213> ORGANISM: Mortierella alpina

<400> SEQUENCE: 7

```
Met Tyr Ser Val Gly Asn Phe Phe Ser Thr Val Thr Lys Phe Tyr Asn
1               5                   10                  15

Glu Ile Asn Pro Ala Thr Leu Ser Gly Ala Ile Asp Ile Val Val
            20                  25                  30

Gln Gln Ala Asn Gly Asp Leu Ala Cys Ser Pro Phe His Val Arg Phe
        35                  40                  45

Gly Lys Leu Ser Val Leu Arg Pro Gln Glu Lys Val Val Glu Val Arg
    50                  55                  60

Val Asn Gly Glu Val Ile Ala Phe Pro Met Lys Val Gly Asp Ala Gly
65                  70                  75                  80

Glu Ala Phe Phe Val Leu Glu Thr Asp Asp Tyr Val Pro Asp Glu Phe
            85                  90                  95

Ala Thr Ser Pro Ile Ala Gly Pro Ser Asp Glu Ala Asp Leu Ala Pro
        100                 105                 110

Val Asp Tyr Phe Asp Leu Asn Gly His Pro His Gly Ser Gln Asp Gln
    115                 120                 125

Lys Arg Arg Gln His Gln Gln Gln Val Leu Glu Gly Met Ser Gly
130                 135                 140

Gln Tyr Pro Gln Gly Thr Glu Asp Asp Ala Pro Leu Asp Asn Gly Tyr
145                 150                 155                 160

Val Ser Ala Ala Ser Gly His Gly Ser Ala Phe Glu Glu Ser Leu Lys
            165                 170                 175

Asp Asp Ser Asp His Glu Ser Val Phe Ser Ala Thr Ser Pro Gly Ser
        180                 185                 190

Ala Glu Arg Ile Ala Ala Asp Ser Asn Thr Lys Asp Thr Ala Leu Asp
    195                 200                 205

Leu Pro Gly Ser Phe Gly Pro Thr Val Val Thr Asn Thr Ile Lys Asn
        210                 215                 220

Lys Asp Ser Ile Asn Phe Pro Val Asp Ala Ile Phe Pro Thr Val Ala
225                 230                 235                 240

His Glu Glu Gln Asp Met Ala Leu Ile Lys Asp Gln Gln Gly Ser Arg
            245                 250                 255

Ser Ser Arg Arg Arg Ser Glu Val Leu Phe Asp Met Thr Gly Tyr Lys
        260                 265                 270

Thr Asp Ser Cys Ser Asp Ser Ser Asp Glu Asp Gly Leu Pro Arg
    275                 280                 285

Gly Ile Leu Ser Asp Ser Glu Arg His Gly Arg Ser Thr Arg Lys Lys
    290                 295                 300

Phe Arg Arg Ser Lys Ser His Leu Ser Met Glu Gln Arg His Gln Leu
305                 310                 315                 320

Leu Glu Asp Ile Lys Gln Gly Ala Phe Leu Pro Glu Glu Ser Leu
            325                 330                 335

Ala Asn Thr Gln Ile Glu Arg Gln Thr Ser Arg Ala Ser Arg Lys Thr
        340                 345                 350

Lys Arg Ala Ser Ile Pro Ser Ala Trp Gln Gly Arg Asn Arg Lys
    355                 360                 365

Arg Ala Asn Ser Met Pro Ala Ile Gly Glu Pro Asp Leu Ala Phe Pro
    370                 375                 380

Ala Tyr Val Ala Arg Arg Pro Asn His Arg Arg Asp Ala Gln Ala Asn
```

```
            385                 390                 395                 400
        Gln Thr Asp Val Ala Met Asp Asp Lys Pro Lys Pro Lys Arg Thr Ala
                        405                 410                 415
        Arg Pro Ser Val Met Ser Asp Thr Glu Met Glu Tyr Glu Ser Asn Asn
                        420                 425                 430
        Val Pro Ala Ser Thr Gln Gly Lys Glu Trp Thr Trp Gly Trp Gly Thr
                        435                 440                 445
        Leu Pro Val Lys Gln Asp Asn Pro Asp Glu Gly Asp Glu Ile Lys Glu
                        450                 455                 460
        Gln Ile Thr Glu Glu Lys Ala Pro Glu Val Pro Val Glu Ile Glu Ala
        465                 470                 475                 480
        Lys Glu Phe Gln Met Gly Ser Thr Lys Cys Arg Val Ala Leu Ser Leu
                        485                 490                 495
        Cys Gly Glu Asp Asp Phe Gly Lys Asp Ile Val Ala Ser His Lys Ala
                        500                 505                 510
        Phe Gln Arg Ala Gln Leu Thr Phe Glu Ala Phe Ser Lys Asp Pro Ala
                        515                 520                 525
        Ala Ile Leu Ala Asp Lys Arg Leu Val Cys Tyr Met Asp Gly Arg Phe
        530                 535                 540
        Tyr Ser Trp Ser Asn Ala Val Pro Gln Leu Ala Ala Leu Leu Phe Phe
        545                 550                 555                 560
        His Gln Pro Leu Ser Asp Ala Ser Ala Leu Asp Leu Lys Asp Gln
                        565                 570                 575
        Lys Ala His Ala Ala Glu Asp Arg Pro Ser Ala Thr Arg Phe Gly Thr
                        580                 585                 590
        Ile Ser Arg Trp Phe Arg Lys Ala Pro Ala Gly Ser Ala Ser Pro Ser
                        595                 600                 605
        Ile Ala Asp Met Ala Ser Ala Ser Ser Thr Thr Leu Ala Gly Gly Glu
                        610                 615                 620
        Thr Ala Val Ala Val Gly Ser Asp Asp Glu Pro Leu His Asn
        625                 630                 635                 640
        Lys Ala Leu Arg Ser Lys Ser Leu Pro Pro Leu Glu Thr Gly Arg Thr
                        645                 650                 655
        Asp Asp His Ser Gln Ser His Val Ala Val Pro Ala Leu Ser Glu Lys
                        660                 665                 670
        Ala Ala Asp Gly Val Pro Asp Gln Lys Arg Tyr Ala Lys Thr Leu Arg
                        675                 680                 685
        Leu Thr Ser Glu Gln Leu Gln Ser Leu Gly Leu Lys Lys Gly Ala Asn
                        690                 695                 700
        Thr Val Ser Phe Ser Val Thr Ser Ser Tyr Gln Gly Thr Ala Thr Cys
        705                 710                 715                 720
        Val Ala Lys Ile Phe Leu Trp Asp Tyr Asp Ser Gln Val Val Ile Ser
                        725                 730                 735
        Asp Ile Asp Gly Thr Ile Thr Lys Ser Asp Ala Leu Gly His Ile Phe
                        740                 745                 750
        Ala Met Ala Gly Arg Asp Trp Thr His Leu Gly Val Ala Lys Leu Phe
                        755                 760                 765
        Thr Asp Ile Arg Ser Asn Gly Tyr His Ile Leu Tyr Leu Thr Ser Arg
                        770                 775                 780
        Ala Ile Gly Gln Ala Asp Tyr Thr Arg Lys Tyr Leu Gln Lys Val Glu
        785                 790                 795                 800
        Gln Asn Ser Tyr Gln Leu Pro Asp Gly Pro Val Ile Met Ser Pro Asp
                        805                 810                 815
```

-continued

Arg Leu Phe Ser Ala Phe His Arg Glu Val Ile Ile Arg Lys Pro Glu
            820                 825                 830

Val Phe Lys Met Ala Cys Leu Arg Asp Val Lys Lys Leu Phe Gly Asp
            835                 840                 845

Arg Asn Pro Phe Tyr Ala Gly Phe Gly Asn Arg Ile Thr Asp Ala Leu
            850                 855                 860

Ser Tyr Arg Ser Val Asn Val Pro Pro Ser Arg Ile Phe Thr Ile Asp
865                 870                 875                 880

Ser Tyr Gly Glu Val Lys Leu Glu Leu Leu Ser Ala Phe Lys Ser Ser
                885                 890                 895

Tyr Leu Ala Leu Asn Asp Leu Val Asn Glu Ile Phe Pro Gly Gln Arg
            900                 905                 910

Val Ala Pro Glu Phe Asn Asp Trp Asn Phe Trp Lys Ser Asp Leu Pro
            915                 920                 925

Arg Ile Asp Leu Pro Asp Leu Pro Ile Pro Asn Asn Asn Tyr Thr Ser
            930                 935                 940

Gly Ser Ser Thr Ser Leu Leu Ser Ser Thr Thr Ser Val Ala Lys Lys
945                 950                 955                 960

Val Ala Ser Leu Thr Ser Ser Ser Ser Ser Asn Leu Leu Gln Pro
            965                 970                 975

Thr Ser Pro Thr Ser Pro Thr Gly Asp Phe Lys Asn Lys Arg Leu Ser
            980                 985                 990

Asn Asp Arg Asn Thr Tyr Ala Gly Val Leu Ser Gly Arg Gln Asp Thr
            995                 1000                1005

Trp Thr Ser Asp Asp Glu Tyr Gln Asp Gln Gln Gln Arg Leu Ile
        1010                1015                1020

Ala Gly Asp Ser Ala Pro Ser Thr Pro Gly Ser Glu Leu Lys Ala
        1025                1030                1035

Gly Gln Glu Leu Lys Glu Asp Ala Arg Lys Ala Arg Ser Gly Ser
        1040                1045                1050

Pro Ser Met Leu Ser Ala Leu Val Pro Ser Arg Leu Ile Arg Ala
        1055                1060                1065

Val Arg Ser Gly Ser Ile Ser Ser Gln Thr Asn Pro Val Pro Ser
        1070                1075                1080

Ser Met Arg Ser Ser Val Thr Pro His Ser Pro Glu Met Lys Gly
        1085                1090                1095

Ile Ile Gly Ser Leu Pro Ser Pro Val Ser Ser Phe Glu Ser Gly
        1100                1105                1110

Ala Asp Val Val Arg Arg Met Ser Ile Pro Ser Pro Pro Pro Leu
        1115                1120                1125

Glu Gly Leu Leu Gln Thr Asp Glu Glu Val Ala Gln Ala Ser Ser
        1130                1135                1140

Lys Ala Leu Ala Leu Gln Gly Ser Asp Thr Ala Asp Leu Ser Arg
        1145                1150                1155

Glu Ser Ser Val Gln Ala Lys Ser Asp Val Met Asp Asp Leu Val
        1160                1165                1170

Ala Val Lys Glu Glu Glu Asp Glu Thr Asp Gln Gln Arg Leu
        1175                1180                1185

Leu Asp Ala Ala Tyr Val Asp Glu Tyr Val Asp Glu Glu Asp Glu
        1190                1195                1200

Glu Gly Tyr Asp Gly Tyr Asp Glu Gln Gly Glu Asp Glu Met Asp
        1205                1210                1215

Glu Glu Asp Glu Glu Asp Glu Tyr Leu Asp Glu Ile Glu Glu Thr
1220                1225                1230

Leu Glu Glu Pro Phe Leu
    1235

<210> SEQ ID NO 8
<211> LENGTH: 3720
<212> TYPE: DNA
<213> ORGANISM: Mortierella alpina

<400> SEQUENCE: 8

```
atgtattctg tcgggaactt cttctcgacc gttacgaaat tctacaatga gatcaacccc    60
gccaccctct ccggcgcaat cgacatcatc gtcgtccagc aggccaacgg cgaccttgca   120
tgctctccct tccacgtgcg tttcggcaaa ctcagcgtcc tccggccgca ggagaaggtc   180
gtcgaggttc gggtcaatgg cgaagtcatc gccttcccca tgaaggtcgg cgacgcagga   240
gaggccttct ttgtgctcga gaccgacgac tatgtgccgg atgagtttgc cacatcgcct   300
atcgctggtc cgagtgacga agccgacctc gcccctgttg actactttga cctgaacggc   360
catccccacg ggtctcagga ccagaaacgg aggcagcatc agcagcaaca ggtgctggag   420
ggcatgagcg acagtatcc tcaaggaaca gaagacgatg ctcctcttga caacggctat   480
gtgagcgctg ctagtggcca tggctctgct tttgaagaga gcttgaagga cgacagcgat   540
cacgagtcgg tcttctcggc acatccccca ggatcagcag aacggatcgc cgccgattct   600
aatactaagg acacagcact cgacttgcct ggatcctttg cccaacggt agtgactaat   660
accatcaaaa acaaggacag catcaacttt ccagttgatg ccatctttcc tacagttgca   720
cacgaggaac aggacatggc tctgatcaaa gatcaacagg gctctcgatc cagccgtcgc   780
agaagtgagg tcctattcga tatgacagga tacaagaccg actcatgctc ggactcgtcg   840
gatgatgagg atggcttgcc tcgtggcatt ctatcggata gtgagcgtca cggtcgtagc   900
acgcgtaaga agttcaggag gagcaagtcg cacctttcaa tggagcagag gcaccaattg   960
ctggaggaca ttaaacaagg agcgttcctg aagcccgagg aaagccttgc aaacacacag  1020
attgaacgtc aaacatcccg ggcaagtagg aaaacaaaga gggcaagcat tccaagtgca  1080
tggcaaggac gaaggaacag gaagagagcc aacagcatgc ctgctatcgg tgaaccagac  1140
ttggcatttc ctgcctatgt ggctcgccga cctaaccatc gtcgcgatgc tcaagcaaac  1200
cagacggatg ttgcaatgga cgacaagccc aagcccaagc gcactgctcg gcccagcgtt  1260
atgagcgata cggagatgga gtatgaatcc aacaatgtcc ctgcatctac ccagggtaaa  1320
gagtggacct ggggatgggg aacgctgcct gtcaaacagg ataaccctga tgaagaggat  1380
gagatcaagg aacaaattac ggaagaaaag gcgcccgaag ttcctgtgga gattgaggca  1440
aaggagtttc agatgggatc aacaaaatgc cgcgtagcgc tcagtctctg cggagaggat  1500
gactttggaa aggacattgt tgctagccac aaggcttttc aaagagccca gttgaccttt  1560
gaggcattct ccaaagatcc cgcggcaatt ctggccgaca gagacttgt gtgttacatg  1620
gatgggcggt tttattcgtg gagtaatgcc gttcctcagc tcgcagccct tctcttcttc  1680
caccagcctc tttcagacgc ggcctctgct ctcgacctca aggaccaaaa ggcacatgcg  1740
gccgaggaca gaccgagcgc cacgcgtttt ggcacaatct ccagatggtt caggaaggcg  1800
cctgcaggca gcgcgtcccc ctctattgca gatatggcct cagcatcctc gacaacccct  1860
gcaggtggtg agaccgccgc tgtcgctgtg ggatcagatg acgacgagcc cttgcacaac  1920
aaggccctgc gtagcaaatc cctgccccca ctggagactg gccggaccga cgaccacagt  1980
```

```
cagagccatg tcgctgtacc tgcgctttcg gagaaagcag cggacggtgt cccagatcag    2040
aagcgctatg ccaagacgct gcggctcacc tcggaacagt tcaatccttg ggtttgaaa     2100 aagggcgcca acacggtctc gttctcagtg acatcgtcct accagggaac tgcaacttgt    2160
gtagccaaga tctttttgtg ggattacgac tcccaggtgg tgatctcgga tattgatggt    2220
acaatcacaa agtcagatgc cctcggccac attttgcca tggccggtcg cgactggacg      2280
catctcggtg tcgccaagct gttcacagat attcgcagca acggatatca catcctgtac    2340
ctgacctccc gagccattgg ccaggcagac tacacacgca agtatcttca gaaggtcgag    2400
caaaacagtt accagctccc ggatggccct gtcatcatga gtccagaccg tctgttctct    2460
gccttccatc gtgaggtgat tatccggaaa ccagaggtgt tcaagatggc gtgtctgcgt    2520
gatgtgaaga agctgtttgg ggacaggaac ccgttctatg ctggatttgg aaaccggatc    2580
acggacgccc tctcctaccg cagtgtcaac gttccaccct cccgaatctt caccattgac    2640
tcttatggtg aggtgaagtt ggagctgctc agtgctttca gtcttcata cttggctttg     2700 aatgacctcg tcaatgagat cttcccagga caacgagttg cacccgagtt caacgactgg    2760
aacttttgga aatcggattt accacggatt gatctccctg atctccccat ccccaacaat    2820
aattatacat caggatcttc gacatcgctc ctctcatcca ccactagcgt ggccaagaag    2880
gtggcgtctt tgaccagctc ttcatcgagc tcgaacctcc tccagccaac gtcgcccact    2940
agccctacgg gagatttcaa gaacaagcgc ctgtctaatg acagaaacac gtatgcgggc    3000
gtcctttcag gacgtcagga cacatggacc agcgatgatg aatatcagga tcaacagcag    3060
cgactgatcg cgggtgactc tgcgccgtca acgccaggat cagagttgaa ggcaggacag    3120
gagctgaagg aggatgcaag gaaggcacga tctggctcgc catcgatgct ctctgctctt    3180
gttccatcgc ggttaatccg cgcagtgagg agtggcagca tcagcagtca gaccaaccct    3240
gtgccctcgt cgatgcggag ttcggttaca ccgcattcgc ccgagatgaa agggatcatc    3300
gggtcgctgc cgtcaccagt gtcttcgttt gagagcggtg cggatgtggt gcgtcggatg    3360
tccattccct cgcctccacc gttggagggg ctgctccaga cggatgagga ggtggctcag    3420
gcatcgagca aggcgctggc gcttcaggga tcggacacag cagatttgag cagagagagc    3480
agtgttcagg ccaagagtga tgtgatggac gaccttgtgg cggtcaagga ggaagaggag    3540
gacgagaccg atcagcagcg gttgctggat gcagcgtatg tggatgagta tgtggatgag    3600
gaggatgagg agggatatga tggatatgac gagcagggtg aggatgagat ggacgaggag    3660
gatgaggagg acgagtatct ggatgagatt gaggagactc tggaggagcc gttcctgtag    3720
```

<210> SEQ ID NO 9
<211> LENGTH: 3846
<212> TYPE: DNA
<213> ORGANISM: Mortierella alpina

<400> SEQUENCE: 9

```
ccttcgcatc accagcccett ctcgtccttc tcgtccttct ctcccacccg cctctcttcc     60
cacgccacac catgtattct gtcgggaact tcttctcgac cgttacgaaa ttctacaatg    120
agatcaaccc cgccaccctc tccggcgcaa tcgacatcat cgtcgtccag caggccaacg    180
gcgaccttgc atgctctccc ttccacgtgc gtttcggcaa actcagcgtc ctccggccgc    240
aggagaaggt cgtcgaggtt cgggtcaatg gcgaagtcat cgccttcccc atgaaggtcg    300
gcgacgcagg agaggccttc tttgtgctcg agaccgacga ctatgtgccg gatgagtttg    360
```

```
ccacatcgcc tatcgctggt ccgagtgacg aagccgacct cgcccctgtt gactactttg      420
acctgaacgg ccatcccac gggtctcagg accagaaacg gaggcagcat cagcagcaac       480
aggtgctgga gggcatgagc ggacagtatc ctcaaggaac agaagacgat gctcctcttg      540
acaacggcta tgtgagcgct gctagtggcc atggctctgc ttttgaagag agcttgaagg      600
acgacagcga tcacgagtcg gtcttctcgg ccacatcccc aggatcagca gaacggatcg      660
ccgccgattc taatactaag gacacagcac tcgacttgcc tggatccttt ggcccaacgg      720
tagtgactaa taccatcaaa acaaggaca gcatcaactt tccagttgat gccatctttc       780
ctacagttgc acacgaggaa caggacatgg ctctgatcaa agatcaacag gctctcgat       840 ccagccgtcg cagaagtgag gtcctattcg atatgacagg atacaagacc gactcatgct      900
cggactcgtc ggatgatgag gatggcttgc ctcgtggcat tctatcggat agtgagcgtc      960
acggtcgtag cacgcgtaag aagttcagga ggagcaagtc gcacctttca atggagcaga     1020
ggcaccaatt gctggaggac attaaacaag gagcgttcct gaagcccgag aaagccttg      1080 caaacacaca gattgaacgt caaacatccc gggcaagtag gaaaacaaag agggcaagca     1140
ttccaagtgc atggcaagga cgaaggaaca ggaagagagc caacagcatg cctgctatcg     1200
gtgaaccaga cttggcattt cctgcctatg tggctcgccg acctaaccat cgtcgcgatg     1260
ctcaagcaaa ccagacggat gttgcaatgg acgacaagcc caagcccaag cgcactgctc     1320
ggcccagcgt tatgagcgat acggagatgg agtatgaatc caacaatgtc cctgcatcta     1380
cccagggtaa agagtggacc tggggatggg aacgctgcc tgtcaaacag gataaccctg      1440
atgaagagga tgagatcaag gaacaaatta cggaagaaaa ggcgcccgaa gttcctgtgg     1500
agattgaggc aaaggagttt cagatgggat caacaaaatg ccgcgtagcg ctcagtctct     1560
gcggagagga tgactttgga aaggacattg ttgctagcca caaggctttt caaagagccc     1620
agttgacctt tgaggcattc tccaaagatc ccgcggcaat tctggccgac aagagacttg     1680
tgtgttacat ggatgggcgg ttttattcgt ggagtaatgc cgttcctcag ctcgcagccc     1740
ttctcttctt ccaccagcct cttttcagacg cggcctctgc tctcgacctc aaggaccaaa    1800
aggcacatgc ggccgaggac agaccgagcg ccacgcgttt tggcacaatc tccagatggt    1860
tcaggaaggc gcctgcaggc agcgcgtccc cctctattgc agatatggcc tcagcatcct    1920
cgacaaccct tgcaggtggt gagaccgccg ctgtcgctgt gggatcagat gacgacgagc    1980
ccttgcacaa caaggccctg cgtagcaaat ccctgccccc actggagact ggccggaccg    2040
acgaccacag tcagagccat gtcgctgtac ctgcgctttc ggagaaagca gcggacggtg    2100
tcccagatca gaagcgctat gccaagacgc tgcggctcac ctcggaacag cttcaatcct    2160
tgggtttgaa aaagggcgcc aacacggtct cgttctcagt gacatcgtcc taccagggaa    2220
ctgcaacttg tgtagccaag atcttttgt gggattacga ctcccaggtg gtgatctcgg     2280
atattgatgg tacaatcaca aagtcagatg ccctcggcca cattttgcc atggccggtc     2340 gcgactggac gcatctcggt gtcgccaagc tgttcacaga tattcgcagc aacggatatc    2400
acatcctgta cctgacctcc cgagccattg gccaggcaga ctacacacgc aagtatcttc    2460
agaaggtcga gcaaaacagt taccagctcc cggatggccc tgtcatcatg agtccagacc    2520
gtctgttctc tgccttccat cgtgaggtga ttatccggaa accagaggtg ttcaagatgg    2580
cgtgtctgcg tgatgtgaag aagctgtttg gggacaggaa cccgttctat gctggatttg    2640
gaaaccggat cacggacgcc ctctcctacc gcagtgtcaa cgttccaccc tcccgaatct    2700
tcaccattga ctcttatggt gaggtgaagt tggagctgct cagtgctttc aagtcttcat    2760
```

```
acttggcttt gaatgacctc gtcaatgaga tcttcccagg acaacgagtt gcacccgagt    2820
tcaacgactg gaacttttgg aaatcggatt taccacggat tgatctccct gatctcccca    2880
tccccaacaa taattataca tcaggatctt cgacatcgct cctctcatcc accactagcg    2940
tggccaagaa ggtggcgtct ttgaccagct cttcatcgag ctcgaacctt ctccagccaa    3000
cgtcgcccac tagccctacg ggagatttca agaacaagcg cctgtctaat gacagaaaca    3060
cgtatgcggg cgtcctttca ggacgtcagg acacatggac cagcgatgat gaatatcagg    3120
atcaacagca gcgactgatc gcgggtgact ctgcgccgtc aacgccagga tcagagttga    3180
aggcaggaca ggagctgaag gaggatgcaa ggaaggcacg atctggctcg ccatcgatgc    3240
tctctgctct tgttccatcg cggttaatcc gcgcagtgag gagtggcagc atcagcagtc    3300
agaccaaccc tgtgccctcg tcgatgcgga gttcggttac accgcattcg cccgagatga    3360
aagggatcat cgggtcgctg ccgtcaccag tgtcttcgtt tgagagcggt gcggatgtgg    3420
tgcgtcggat gtccattccc tcgcctccac cgttggaggg gctgctccag acggatgagg    3480
aggtggctca ggcatcgagc aaggcgctgg cgcttcaggg atcggacaca gcagatttga    3540
gcagagagag cagtgttcag gccaagagtg atgtgatgga cgaccttgtg gcggtcaagg    3600
aggaagagga ggacgagacc gatcagcagc ggttgctgga tgcagcgtat gtggatgagt    3660
atgtggatga ggaggatgag gagggatatg atggatatga cgagcagggt gaggatgaga    3720
tggacgagga ggatgaggag gacgagtatc tggatgagat tgaggagact ctggaggagc    3780
cgttcctgta gacgcgtttt ataatttttg taaaagttcc cttgttgtaa aaaaaaaaa     3840 aaaaaa                                                               3846

<210> SEQ ID NO 10
<211> LENGTH: 4552
<212> TYPE: DNA
<213> ORGANISM: Mortierella alpina

<400> SEQUENCE: 10
atgtattctg tcgggaactt cttctcgacc gttacgaaat tctacaatga gatcaacccc      60
gccaccctct ccggcgcaat cgacatcatc gtcgtccagc aggccaacgg cgaccttgca     120
tgctctccct tccacgtgcg tttcggcaaa ctcagcgtcc tccggccgca ggagaaggtc     180
gtcgaggttc gggtcaatgg cgaagtcatc gccttcccca tgaaggtcgg cgacgcagga     240
gaggccttct ttgtgctcga accgacgac tatgtgccgg atgagtttgc cacatcgcct      300
atcgctggtc cgagtgacga agccgacctc gcccctgttg actactttga cctgaacggc     360
catccccacg ggtctcagga ccagaaacgg aggcagcatc agcagcaaca ggtgctggag     420
ggcatgagcg acagtatcc tcaaggaaca gaaggtagag atcgatatga acactatgaa      480
cgcacgatgg cgtctttagc ccactgtcag tgtcagtgca gcacagctgt gttgtaaaag     540
cgttgacata tgtcagagcg cattttttct tcaatatttc agacgcagcg gtcaggacaa     600
acacatggga ttatatatga atatactcaa tcgatcgcac tctttctttt tgttctcccg     660
cggctatcaa tagacgatgc tcctcttgac aacggctatg tgagcgctgc tagtggccat     720
ggctctgctt tgaagagag cttgaaggac gacagcgatc acgagtcggt cttctcggcc      780
acatccccag gatcagcaga acggatcgcc gccgattcta atactaagga cacagcactc     840
gacttgcctg gatcctttgg cccaacggta gtgactaata ccatcaaaaa caaggacagc     900
atcaactttc cagttgatgc catctttcct acagttgcac acgaggaaca ggacatggct     960
```

-continued

```
ctgatcaaag atcaacaggg ctctcgatcc agccgtcgca gaagtggtac gatgttctta    1020
ctgaacttta tataccatga tctctgctgc atatgattcc gcttcccgta ctatgctctg    1080
ctgtcggcat tcctaaccat attttatccg ttaatgtttg ttttgggcgt tcgaattgat    1140
gcagaggtcc tattcgatat gacaggatac aagaccgact catgctcgga ctcgtcggat    1200
gatgaggatg gcttgcctcg tggcattcta tcggatagtg agcgtcacgg tcgtagcacg    1260
cgtaagaagt tcaggaggag caagtcgcac ctttcaatgg agcagaggca ccaattgctg    1320
gaggacatta acaaggagc gttcctgaag cccgaggaaa gccttgcaaa cacacagatt    1380
gaacgtcaaa gtaggcacac tagtttatcg caccttgatg atcatctcag cgacgtctct    1440
gccccaactc actcttgata ttttttttt atcttcagca tcccgggcaa gtaggaaaac    1500
aaagagggca agcattccaa gtgcatggca aggacgaagg aacaggaaga gagccaacag    1560
catgcctgct atcggtgaac caggtagcga tcatgtacca tatggaagga gtaactgtta    1620
gaaattgcag tcagctaata tgttttataa ctcttgtaca gacttggcat ttcctgccta    1680
tgtggctcgc cgacctaacc atcgtcgcga tgctcaagca aaccagacgg atgttgcaat    1740
ggacgacaag cccaagccca agcgcactgc tcggcccagc gttatgagcg atacggagat    1800
ggaggtaaga atcgcaactt gacataaatt acagtgtatc gatcgacctg tggcctcagt    1860
gactactgtt actcatctgc ttttcgcaaa cgttctgcaa ctagtatgaa tccaacaatg    1920
tccctgcatc tacccagggt aaagagtgga cctgggatg gggaacgctg cctgtcaaac    1980
aggataaccc tgatgaagag gatgagatca aggaacaaat tacggaagaa aaggcgcccg    2040
aagttcctgt ggagattgag gcaaaggagt ttcagatggg atcaacaaaa tgccgcgtag    2100
cgctcagtct ctgcggagag gatgactttg gaaaggacat tgtaggttac catcgcagtc    2160
cttactccct ttactcagtc atcagtacgt cgttggtatt tgaattgcag tttaacatgt    2220
ggcctctgct tgtgatatag gttgctagcc acaaggcttt tcaaagagcc cagttgacct    2280
ttgaggcatt ctccaaagat cccgcggcaa ttctggccga caagagactt gtgtgttaca    2340
tggatgggcg gttttattcg tggagtaatg ccgttcctca gctcgcagcc cttctcttct    2400
tccaccagcc tctttcagac gcggcctctg ctctcgacct caaggaccaa aaggcacatg    2460
cggccgagga cagaccgagc gccacgcgtt ttggcacaat ctccagatgg ttcaggaagg    2520
cgcctgcagg cagcgcgtcc ccctctattg cagatatggc ctcagcatcc tcgcaaccc    2580 ttgcaggtgg tgagaccgcc gctgtcgctg tgggatcaga tgacgacgag cccttgcaca    2640
acaaggccct gcgtagcaaa tccctgcccc cactggagac tggccggacc gacgaccaca    2700
gtcagagcca tgtcgctgta cctgcgcttt cggagaaagc agcggacggt gtcccagatc    2760
agaagcgcta tgccaagacg ctgcggctca cctcggaaca gcttcaatcc ttgggtttga    2820
aaaagggcgc caacacggtc tcgttctcag tgacatcgtc ctaccaggga actgcaactt    2880
gtgtagccaa gatcttttg tgggattacg actcccaggt ggtgatctcg gatattgatg    2940
gtacaatcac aaagtcagat gccctcggcc acatttttgc catggccggt cgcgactgga    3000
cgcatctcgg tgtcgccaag ctgttcacag atattcgcag caacggatat cacatcctgt    3060
acctgacctc ccgagccatt ggccaggcag actacacacg caagtatctt cagaaggtcg    3120
agcaaaacag ttaccagctc ccggatggcc ctgtcatcat gagtccagac cgtctgttct    3180
ctgccttcca tcgtgaggtg attatccgga aaccagaggt gttcaagatg gcgtgtctgc    3240
gtgatgtgaa gaagctgttt ggggacagga acccgttcta tgctggattt ggaaaccgga    3300
tcacggacgc cctctcctac cgcagtgtca acgttccacc ctcccgaatc ttcaccattg    3360
```

```
actcttatgg tgaggtgaag ttggagctgc tcagtgcttt caagtcttcg taagtgtctc    3420
tgctttccac ggcaatcaga agtgtgaaag aaggaatcaa agtggcgttt ttattatctc    3480
tccttcatta cttatcctcg ttacaacttt gtacggtaga tacttggctt tgaatgacct    3540
cgtcaatgag atcttcccag acaacgagt tgcacccgag ttcaacgact ggaacttttg     3600
gaaatcggat ttaccacgga ttgatctccc tgatctcccc atccccaaca ataattatac    3660
atcaggatct tcgacatcgc tcctctcatc caccactagc gtggcaagaa ggtggcgtc    3720 tttgaccagc tcttcatcga gctcgaacct tctccagcca acgtcgccca ctagccctac    3780
gggagatttc aagaacaagc gcctgtctaa tgacagaaac acgtatgcgg gcgtcctttc    3840
aggacgtcag gacacatgga ccagcgatga tgaatatcag gatcaacagc agcgactgat    3900
cgcgggtgac tctgcgccgt caacgccagg atcagagttg aaggcaggac aggagctgaa    3960
ggaggatgca aggaaggcac gatctggctc gccatcgatg ctctctgctc ttgttccatc    4020
gcggttaatc cgcgcagtga ggagtggcag catcagcagt cagaccaacc ctgtgccctc    4080
gtcgatgcgg agttcggtta caccgcattc gcccgagatg aaagggatca tcgggtcgct    4140
gccgtcacca gtgtcttcgt ttgagagcgg tgcggatgtg gtgcgtcgga tgtccattcc    4200
ctcgcctcca ccgttggagg ggctgctcca gacggatgag gaggtggctc aggcatcgag    4260
caaggcgctg gcgcttcagg gatcggacac agcagatttg agcagagaga gcagtgttca    4320
ggccaagagt gatgtgatgg acgaccttgt ggcggtcaag gaggaagagg aggacgagac    4380
cgatcagcag cggttgctgg atgcagcgta tgtggatgag tatgtggatg aggaggatga    4440
ggagggatat gatggatatg acgagcaggg tgaggatgag atggacgagg aggatgagga    4500
ggacgagtat ctggatgaga ttgaggagac tctggaggag ccgttcctgt ag            4552
```

<210> SEQ ID NO 11
<211> LENGTH: 23
<212> TYPE: DNA
<213> ORGANISM: Artificial sequence
<220> FEATURE:
<223> OTHER INFORMATION: primer MAPAH1-1-3F

<400> SEQUENCE: 11
cgccaataca ttgacgtttt cag                                              23

<210> SEQ ID NO 12
<211> LENGTH: 25
<212> TYPE: DNA
<213> ORGANISM: Artificial sequence
<220> FEATURE:
<223> OTHER INFORMATION: primer MaPAH1-1-5R

<400> SEQUENCE: 12
agttccagtc attgaactcg ggtgc                                            25

<210> SEQ ID NO 13
<211> LENGTH: 26
<212> TYPE: DNA
<213> ORGANISM: Artificial sequence
<220> FEATURE:
<223> OTHER INFORMATION: primer MaPAH1-2-3F

<400> SEQUENCE: 13
gagcccagtt gacctttgag gcattc                                           26

<210> SEQ ID NO 14

```
<211> LENGTH: 25
<212> TYPE: DNA
<213> ORGANISM: Artificial sequence
<220> FEATURE:
<223> OTHER INFORMATION: primer MaPAH1-2-5R

<400> SEQUENCE: 14
cactgagaac gagaccgtgt tggcg                                              25

<210> SEQ ID NO 15
<211> LENGTH: 25
<212> TYPE: DNA
<213> ORGANISM: Artificial sequence
<220> FEATURE:
<223> OTHER INFORMATION: primer NotI-PAH1-1-F

<400> SEQUENCE: 15
gcggccgcat gcagtccgtg ggaag                                              25

<210> SEQ ID NO 16
<211> LENGTH: 24
<212> TYPE: DNA
<213> ORGANISM: Artificial sequence
<220> FEATURE:
<223> OTHER INFORMATION: primer MaPAH1-1-10R

<400> SEQUENCE: 16
ttcttgagta gctgctgttg ttcg                                               24

<210> SEQ ID NO 17
<211> LENGTH: 28
<212> TYPE: DNA
<213> ORGANISM: Artificial sequence
<220> FEATURE:
<223> OTHER INFORMATION: primer KpnI-PAH1-F

<400> SEQUENCE: 17
ggtaccatgc agtacgtagg cagagctc                                           28

<210> SEQ ID NO 18
<211> LENGTH: 28
<212> TYPE: DNA
<213> ORGANISM: Artificial sequence
<220> FEATURE:
<223> OTHER INFORMATION: primer XhoI-PAH1-R

<400> SEQUENCE: 18
ctcgagttaa tcttcgaatt catcttcg                                           28

<210> SEQ ID NO 19
<211> LENGTH: 862
<212> TYPE: PRT
<213> ORGANISM: Saccharomyces cerevisiae

<400> SEQUENCE: 19

Met Gln Tyr Val Gly Arg Ala Leu Gly Ser Val Ser Lys Thr Trp Ser
1               5                   10                  15

Ser Ile Asn Pro Ala Thr Leu Ser Gly Ala Ile Asp Val Ile Val Val
                20                  25                  30

Glu His Pro Asp Gly Arg Leu Ser Cys Ser Pro Phe His Val Arg Phe
            35                  40                  45

Gly Lys Phe Gln Ile Leu Lys Pro Ser Gln Leu Lys Val Gln Val Phe
        50                  55                  60

Ile Asn Glu Lys Leu Ser Asn Met Pro Met Lys Leu Ser Asp Ser Gly
```

```
            65                  70                  75                  80
Glu Ala Tyr Phe Val Phe Glu Met Gly Asp Gln Val Thr Asp Val Pro
                85                  90                  95

Asp Glu Leu Leu Val Ser Pro Val Met Ser Ala Thr Ser Ser Pro Pro
               100                 105                 110

Gln Ser Pro Glu Thr Ser Ile Leu Glu Gly Gly Thr Glu Gly Glu Gly
               115                 120                 125

Glu Gly Glu Asn Glu Asn Lys Lys Glu Lys Lys Val Leu Glu Glu
           130                 135                 140

Pro Asp Phe Leu Asp Ile Asn Asp Thr Gly Asp Ser Gly Ser Lys Asn
145                 150                 155                 160

Ser Glu Thr Thr Gly Ser Leu Ser Pro Thr Glu Ser Ser Thr Thr Thr
                   165                 170                 175

Pro Pro Asp Ser Val Glu Glu Arg Lys Leu Val Glu Gln Arg Thr Lys
               180                 185                 190

Asn Phe Gln Gln Lys Leu Asn Lys Leu Thr Glu Ile His Ile Pro
           195                 200                 205

Ser Lys Leu Asp Asn Asn Gly Asp Leu Leu Leu Asp Thr Glu Gly Tyr
210                 215                 220

Lys Pro Asn Lys Asn Met Met His Asp Thr Asp Ile Gln Leu Lys Gln
225                 230                 235                 240

Leu Leu Lys Asp Glu Phe Gly Asn Asp Ser Asp Ile Ser Ser Phe Ile
               245                 250                 255

Lys Glu Asp Lys Asn Gly Asn Ile Lys Ile Val Asn Pro Tyr Glu His
               260                 265                 270

Leu Thr Asp Leu Ser Pro Pro Gly Thr Pro Thr Met Ala Thr Ser
       275                 280                 285

Gly Ser Val Leu Gly Leu Asp Ala Met Glu Ser Gly Ser Thr Leu Asn
           290                 295                 300

Ser Leu Ser Ser Ser Pro Ser Gly Ser Asp Thr Glu Asp Glu Thr Ser
305                 310                 315                 320

Phe Ser Lys Glu Gln Ser Ser Lys Ser Glu Lys Thr Ser Lys Lys Gly
                   325                 330                 335

Thr Ala Gly Ser Gly Glu Thr Glu Lys Arg Tyr Ile Arg Thr Ile Arg
               340                 345                 350

Leu Thr Asn Asp Gln Leu Lys Cys Leu Asn Leu Thr Tyr Gly Glu Asn
               355                 360                 365

Asp Leu Lys Phe Ser Val Asp His Gly Lys Ala Ile Val Thr Ser Lys
       370                 375                 380

Leu Phe Val Trp Arg Trp Asp Val Pro Ile Val Ile Ser Asp Ile Asp
385                 390                 395                 400

Gly Thr Ile Thr Lys Ser Asp Ala Leu Gly His Val Leu Ala Met Ile
                   405                 410                 415

Gly Lys Asp Trp Thr His Leu Gly Val Ala Lys Leu Phe Ser Glu Ile
               420                 425                 430

Ser Arg Asn Gly Tyr Asn Ile Leu Tyr Leu Thr Ala Arg Ser Ala Gly
           435                 440                 445

Gln Ala Asp Ser Thr Arg Ser Tyr Leu Arg Ser Ile Glu Gln Asn Gly
           450                 455                 460

Ser Lys Leu Pro Asn Gly Pro Val Ile Leu Ser Pro Asp Arg Thr Met
465                 470                 475                 480

Ala Ala Leu Arg Arg Glu Val Ile Leu Lys Lys Pro Glu Val Phe Lys
                   485                 490                 495
```

```
Ile Ala Cys Leu Asn Asp Ile Arg Ser Leu Tyr Phe Glu Asp Ser Asp
            500                 505                 510

Asn Glu Val Asp Thr Glu Lys Ser Thr Pro Phe Ala Gly Phe
            515                 520                 525

Gly Asn Arg Ile Thr Asp Ala Leu Ser Tyr Arg Thr Val Gly Ile Pro
        530                 535                 540

Ser Ser Arg Ile Phe Thr Ile Asn Thr Glu Gly Val His Met Glu
545                 550                 555                 560

Leu Leu Glu Leu Ala Gly Tyr Arg Ser Ser Tyr Ile His Ile Asn Glu
                565                 570                 575

Leu Val Asp His Phe Phe Pro Pro Val Ser Leu Asp Ser Val Asp Leu
            580                 585                 590

Arg Thr Asn Thr Ser Met Val Pro Gly Ser Pro Pro Asn Arg Thr Leu
        595                 600                 605

Asp Asn Phe Asp Ser Glu Ile Thr Ser Gly Arg Lys Thr Leu Phe Arg
    610                 615                 620

Gly Asn Gln Glu Glu Lys Phe Thr Asp Val Asn Phe Trp Arg Asp Pro
625                 630                 635                 640

Leu Val Asp Ile Asp Asn Leu Ser Asp Ile Ser Asn Asp Ser Asp
                645                 650                 655

Asn Ile Asp Glu Asp Thr Asp Val Ser Gln Gln Ser Asn Ile Ser Arg
                660                 665                 670

Asn Arg Ala Asn Ser Val Lys Thr Ala Lys Val Thr Lys Ala Pro Gln
        675                 680                 685

Arg Asn Val Ser Gly Ser Thr Asn Asn Asn Glu Val Leu Ala Ala Ser
    690                 695                 700

Ser Asp Val Glu Asn Ala Ser Asp Leu Val Ser Ser His Ser Ser Ser
705                 710                 715                 720

Gly Ser Thr Pro Asn Lys Ser Thr Met Ser Lys Gly Asp Ile Gly Lys
                725                 730                 735

Gln Ile Tyr Leu Glu Leu Gly Ser Pro Leu Ala Ser Pro Lys Leu Arg
            740                 745                 750

Tyr Leu Asp Asp Met Asp Asp Glu Asp Ser Asn Tyr Asn Arg Thr Lys
            755                 760                 765

Ser Arg Arg Ala Ser Ser Ala Ala Thr Ser Ile Asp Lys Glu Phe
770                 775                 780

Lys Lys Leu Ser Val Ser Lys Ala Gly Ala Pro Thr Arg Ile Val Ser
785                 790                 795                 800

Lys Ile Asn Val Ser Asn Asp Val His Ser Leu Gly Asn Ser Asp Thr
                805                 810                 815

Glu Ser Arg Arg Glu Gln Ser Val Asn Glu Thr Gly Arg Asn Gln Leu
            820                 825                 830

Pro His Asn Ser Met Asp Asp Lys Asp Leu Asp Ser Arg Val Ser Asp
            835                 840                 845

Glu Phe Asp Asp Asp Glu Phe Asp Glu Asp Glu Phe Glu Asp
    850                 855                 860

<210> SEQ ID NO 20
<211> LENGTH: 891
<212> TYPE: PRT
<213> ORGANISM: Mus musculus

<400> SEQUENCE: 20

Met Asn Tyr Val Gly Gln Leu Ala Gly Gln Val Phe Val Thr Val Lys
```

-continued

```
1               5                   10                  15
Glu Leu Tyr Lys Gly Leu Asn Pro Ala Thr Leu Ser Gly Cys Ile Asp
                20                  25                  30
Ile Ile Val Ile Arg Gln Pro Asn Gly Ser Leu Gln Cys Ser Pro Phe
                35                  40                  45
His Val Arg Phe Gly Lys Met Gly Val Leu Arg Ser Arg Glu Lys Val
                50                  55                  60
Val Asp Ile Glu Ile Asn Gly Glu Ser Val Asp Leu His Met Lys Leu
65                  70                  75                  80
Gly Asp Asn Gly Glu Ala Phe Phe Val Gln Glu Thr Asp Asn Asp Gln
                85                  90                  95
Glu Ile Ile Pro Met Tyr Leu Ala Thr Ser Pro Ile Leu Ser Glu Gly
                100                 105                 110
Ala Ala Arg Met Glu Ser Gln Leu Lys Arg Asn Ser Val Asp Arg Ile
                115                 120                 125
Arg Cys Leu Asp Pro Thr Thr Ala Ala Gln Gly Leu Pro Pro Ser Asp
                130                 135                 140
Thr Pro Ser Thr Gly Ser Leu Gly Lys Lys Arg Arg Lys Arg Arg Arg
145                 150                 155                 160
Lys Ala Gln Leu Asp Asn Leu Lys Arg Asp Asp Asn Val Asn Ser Ser
                165                 170                 175
Glu Asp Glu Asp Met Phe Pro Ile Glu Met Ser Ser Asp Glu Asp Thr
                180                 185                 190
Ala Pro Met Asp Gly Ser Arg Thr Leu Pro Asn Asp Val Pro Pro Phe
                195                 200                 205
Gln Asp Asp Ile Pro Lys Glu Asn Phe Pro Ser Ile Ser Thr His Pro
                210                 215                 220
Gln Ser Ala Ser Tyr Pro Ser Ser Asp Arg Glu Trp Ser Pro Ser Pro
225                 230                 235                 240
Ser Pro Ser Gly Ser Arg Pro Ser Thr Pro Lys Ser Asp Ser Glu Leu
                245                 250                 255
Val Ser Lys Ser Ala Asp Arg Leu Thr Pro Lys Asn Asn Leu Glu Met
                260                 265                 270
Leu Trp Leu Trp Gly Glu Leu Pro Gln Ala Ala Lys Ser Ser Ser Pro
                275                 280                 285
His Lys Met Lys Glu Ser Ser Pro Leu Gly Ser Arg Lys Thr Pro Asp
                290                 295                 300
Lys Met Asn Phe Gln Ala Ile His Ser Glu Ser Ser Asp Thr Phe Ser
305                 310                 315                 320
Asp Gln Ser Pro Thr Met Ala Arg Gly Leu Leu Ile His Gln Ser Lys
                325                 330                 335
Ala Gln Thr Glu Met Gln Phe Val Asn Glu Glu Asp Leu Glu Ser Leu
                340                 345                 350
Gly Ala Ala Ala Pro Pro Ser Pro Val Ala Glu Glu Leu Lys Ala Pro
                355                 360                 365
Tyr Pro Asn Thr Ala Gln Ser Ser Lys Thr Asp Ser Pro Ser Arg
                370                 375                 380
Lys Lys Asp Lys Arg Ser Arg His Leu Gly Ala Asp Gly Val Tyr Leu
385                 390                 395                 400
Asp Asp Leu Thr Asp Met Asp Pro Glu Val Ala Ala Leu Tyr Phe Pro
                405                 410                 415
Lys Asn Gly Asp Pro Gly Gly Leu Pro Lys Gln Ala Ser Asp Asn Val
                420                 425                 430
```

```
Ala Arg Ser Ala Asn Gln Ser Pro Gln Ser Val Gly Gly Ser Gly Ile
        435                 440                 445

Asp Ser Gly Val Glu Ser Thr Ser Asp Ser Leu Arg Asp Leu Pro Ser
450                 455                 460

Ile Ala Ile Ser Leu Cys Gly Leu Ser Asp His Arg Glu Ile Thr
465                 470                 475                 480

Lys Asp Ala Phe Leu Glu Gln Ala Val Ser Tyr Gln Gln Phe Ala Asp
                485                 490                 495

Asn Pro Ala Ile Ile Asp Asp Pro Asn Leu Val Val Lys Val Gly Asn
                500                 505                 510

Lys Tyr Tyr Asn Trp Thr Thr Ala Ala Pro Leu Leu Leu Ala Met Gln
        515                 520                 525

Ala Phe Gln Lys Pro Leu Pro Lys Ala Thr Val Glu Ser Ile Met Arg
        530                 535                 540

Asp Lys Met Pro Lys Lys Gly Arg Trp Trp Phe Ser Trp Arg Gly
545                 550                 555                 560

Arg Asn Ala Thr Ile Lys Glu Glu Ser Lys Pro Glu Gln Cys Leu Thr
                565                 570                 575

Gly Lys Gly His Asn Thr Gly Gln Pro Ala Gln Leu Gly Leu Ala
                580                 585                 590

Thr Arg Ile Lys His Glu Ser Ser Ser Asp Glu Glu His Ala Ala
        595                 600                 605

Ala Lys Pro Ser Gly Ser Ser His Leu Ser Leu Leu Ser Asn Val Ser
        610                 615                 620

Tyr Lys Lys Thr Leu Arg Leu Thr Ser Glu Gln Leu Lys Ser Leu Lys
625                 630                 635                 640

Leu Lys Asn Gly Pro Asn Asp Val Val Phe Ser Val Thr Thr Gln Tyr
                645                 650                 655

Gln Gly Thr Cys Arg Cys Glu Gly Thr Ile Tyr Leu Trp Asn Trp Asp
                660                 665                 670

Asp Lys Val Ile Ile Ser Asp Ile Asp Gly Thr Ile Thr Arg Ser Asp
        675                 680                 685

Thr Leu Gly His Ile Leu Pro Thr Leu Gly Lys Asp Trp Thr His Gln
        690                 695                 700

Gly Ile Ala Lys Leu Tyr His Lys Val Ser Gln Asn Gly Tyr Lys Phe
705                 710                 715                 720

Leu Tyr Cys Ser Ala Arg Ala Ile Gly Met Ala Asp Met Thr Arg Gly
                725                 730                 735

Tyr Leu His Trp Val Asn Glu Arg Gly Thr Val Leu Pro Gln Gly Pro
                740                 745                 750

Leu Leu Leu Ser Pro Ser Ser Leu Phe Ser Ala Leu His Arg Glu Val
                755                 760                 765

Ile Glu Lys Lys Pro Glu Lys Phe Lys Val Gln Cys Leu Thr Asp Ile
        770                 775                 780

Lys Asn Leu Phe Phe Pro Asn Thr Glu Pro Phe Tyr Ala Ala Phe Gly
785                 790                 795                 800

Asn Arg Pro Ala Asp Val Tyr Ser Tyr Lys Gln Val Gly Val Ser Leu
                805                 810                 815

Asn Arg Ile Phe Thr Val Asn Pro Lys Gly Glu Leu Val Gln Glu His
                820                 825                 830

Ala Lys Thr Asn Ile Ser Ser Tyr Val Arg Leu Cys Glu Val Val Asp
        835                 840                 845
```

-continued

```
His Val Phe Pro Leu Leu Lys Arg Ser His Ser Cys Asp Phe Pro Cys
    850                 855             860

Ser Asp Thr Phe Ser Asn Phe Thr Phe Trp Arg Glu Pro Leu Pro Pro
865             870             875                     880

Phe Glu Asn Gln Asp Met His Ser Ala Ser Ala
                885             890
```